United States Patent
Chalasani et al.

(10) Patent No.: US 10,806,951 B2
(45) Date of Patent: Oct. 20, 2020

(54) SONOGENIC STIMULATION OF CELLS

(71) Applicant: Salk Institute for Biological Studies, La Jolla, CA (US)

(72) Inventors: Sreekanth H. Chalasani, La Jolla, CA (US); Stuart Ibsen, La Jolla, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 1184 days.

(21) Appl. No.: 14/843,108

(22) Filed: Sep. 2, 2015

(65) Prior Publication Data

US 2016/0220672 A1 Aug. 4, 2016

Related U.S. Application Data

(60) Provisional application No. 62/054,600, filed on Sep. 24, 2014.

(51) Int. Cl.
| | | |
|---|---|---|
| A61N 7/00 | (2006.01) | |
| C12N 13/00 | (2006.01) | |
| C07K 14/705 | (2006.01) | |
| A61K 41/00 | (2020.01) | |
| A61B 8/00 | (2006.01) | |
| G01N 29/00 | (2006.01) | |
| A61K 38/00 | (2006.01) | |

(52) U.S. Cl.
CPC ............ *A61N 7/00* (2013.01); *A61K 41/0033* (2013.01); *C07K 14/705* (2013.01); *C12N 13/00* (2013.01); *A61B 8/00* (2013.01); *A61K 38/00* (2013.01); *A61N 2007/0026* (2013.01); *G01N 29/00* (2013.01)

(58) Field of Classification Search
CPC .............. A61N 7/00; A61N 2007/0026; C07K 14/705; A61K 41/0033; A61K 38/00; C12N 13/00; A61B 8/00; G01N 29/00
See application file for complete search history.

(56) References Cited

U.S. PATENT DOCUMENTS

| | | | | |
|---|---|---|---|---|
| 2002/0177782 | A1* | 11/2002 | Penner ..................... | A61B 5/00 600/485 |
| 2003/0144191 | A1* | 7/2003 | Lee ....................... | C07K 14/705 435/69.1 |
| 2003/0225331 | A1* | 12/2003 | Diederich ................ | A61N 7/02 600/437 |
| 2008/0033297 | A1* | 2/2008 | Sliwa ..................... | A61B 5/055 600/439 |
| 2011/0092880 | A1* | 4/2011 | Gertner .................. | A61B 5/412 604/20 |

(Continued)

OTHER PUBLICATIONS

Yin et al., "Mechanotransduction by TRP Channels: General Concepts and Specific Role in the Vasculature", (2010), Cell Biochem Biophys, vol. 56, pp. 1-18. (Year: 2010).*

(Continued)

*Primary Examiner* — Peter Luong
(74) *Attorney, Agent, or Firm* — Greenberg Traurig, LLP; Melissa Hunter-Ensor; Leslie Serunian

(57) ABSTRACT

The invention provides compositions featuring TRP-4 polypeptides and polynucleotides, methods for expressing such polypeptides and polynucleotides in a cell type of interest, and methods for inducing the activation of the TRP-4 polypeptide in neurons and other cell types using ultrasound.

35 Claims, 42 Drawing Sheets

Specification includes a Sequence Listing.

(56) References Cited

U.S. PATENT DOCUMENTS

2012/0289757 A1* 11/2012 Boyden ................. A61N 5/025
600/1

OTHER PUBLICATIONS

Dong et al., "TRP Channels of Intracellular Membranes," Journal of Neurochemistry, Apr. 2010; vol. 113, Issue 2: pp. 313-328, doi:10.1111/j.1471-4159.2010.06626.x.

Gray et al., "A circuit for navigation in Caenorhabditis elegans," Proceedings of the National Academy of Sciences USA, Mar. 2005; vol. 102, No. 9: pp. 3184-3191.

Kang et al., "C. elegans TRP family protein TRP-4 is a pore-forming subunit of a native mechanotransduction channel," Neuron, Aug. 2010, vol. 67, Issue 3: pp. 381-391, doi:10.1016/j.neuron.2010.06.032.

Liedtke et al., "Mammalian TRPV4 (VR-OAC) directs behavioral responses to osmotic and mechanical stimuli in Caenorhabditis elegans," Proceedings of the National Academy of Sciences USA, Nov. 2003, vol. 100, Supplement 2: pp. 14531-14536.

Venkatachalam et al., "TRP Channels," Annual Review of Biochemistry, 2007; vol. 76: pp. 387-417, doi:10.1146/annurev.biochem.75.103004.142819.

Zheng et al., "Molecular Mechanism of TRP Channels," Comprehensive Physiology, Jan. 2013; vol. 3, Issue 1: pp. 221-242, doi:10.1002/cphy.c120001.

* cited by examiner

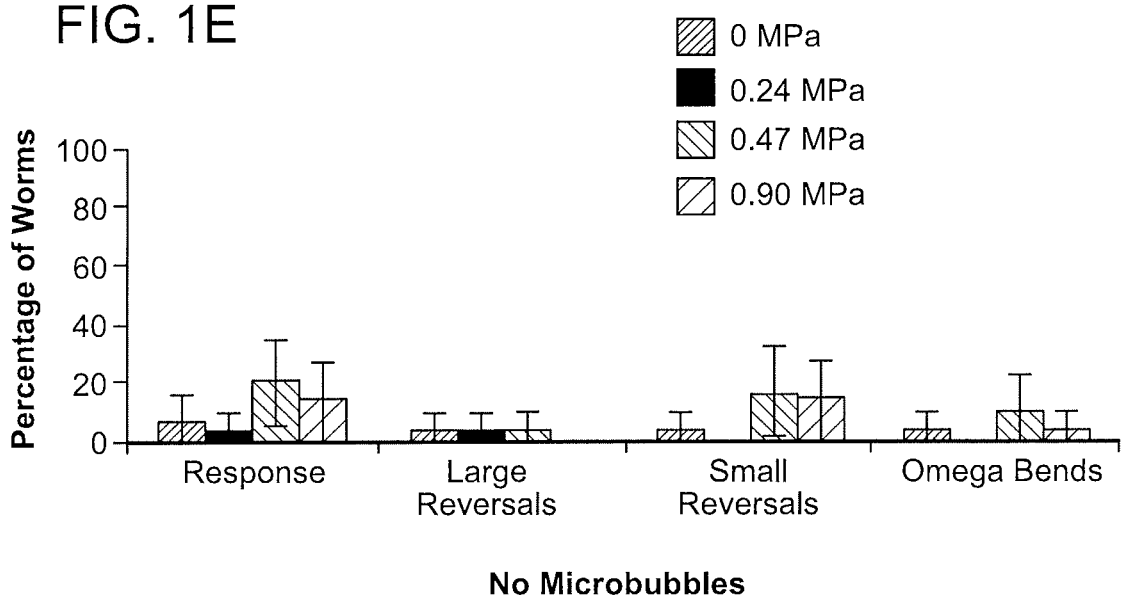
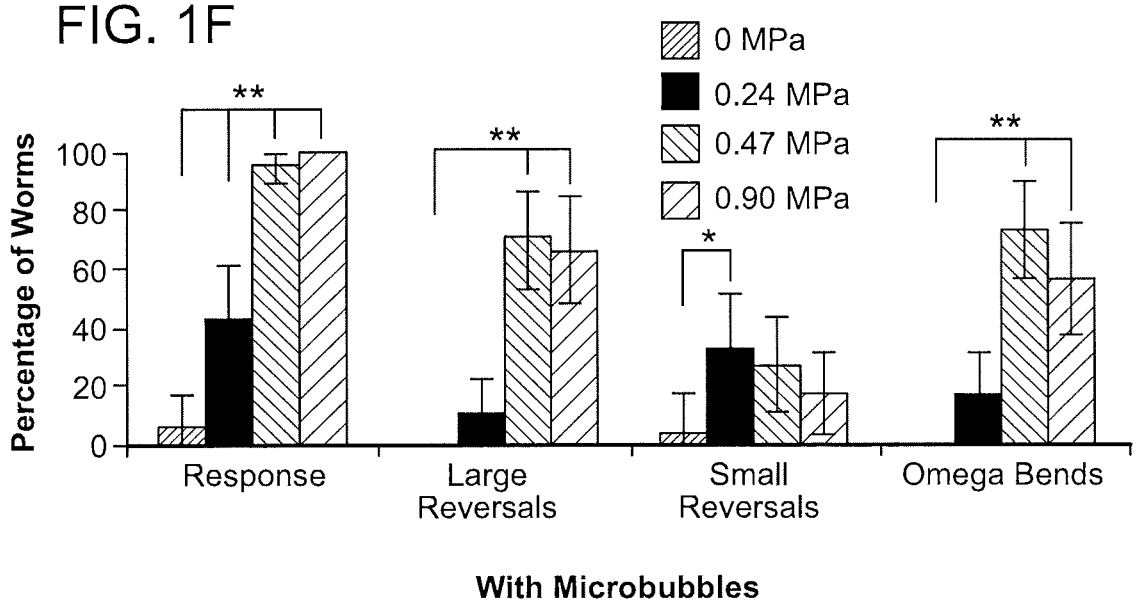

PVD Cell Body

Ultrasound Exposure

Reversal Initiation

Small Reversal Limit

Large Reversal Limit

Last Head Bend

Omega Bend Initiation

Forward Motion In Opposite Direction

AIY::*GCaMP*; AIY::*trp4* Responders without Ultrasound (n = 2)

AIY::*GCaMP*; AIY::*trp4* Non-Responders without Ultrasound (n = 17)

Before Ultrasound

After Ultrasound

FIG. 15A

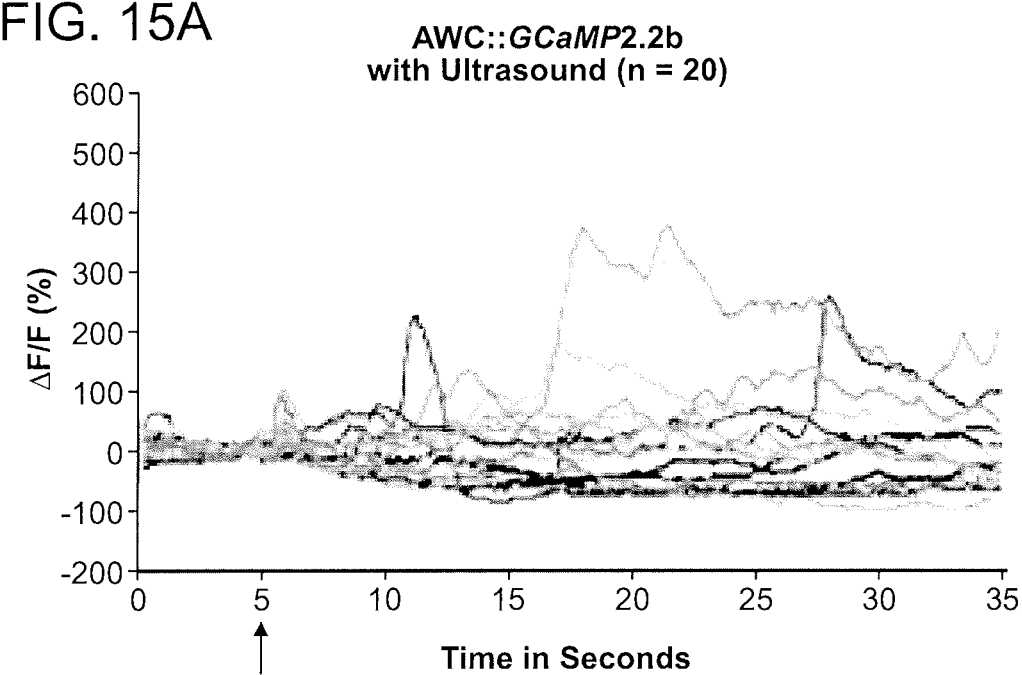

AWC calcium responses to ultrasound stimulus. Ratio of change in fluoresence to baseline fluorescence in AWC neurons expressing the calcium sensor, GCaMP2.2b (n=20) and *trp-4* specifically in AWC neurons (n=23)

FIG. 15B

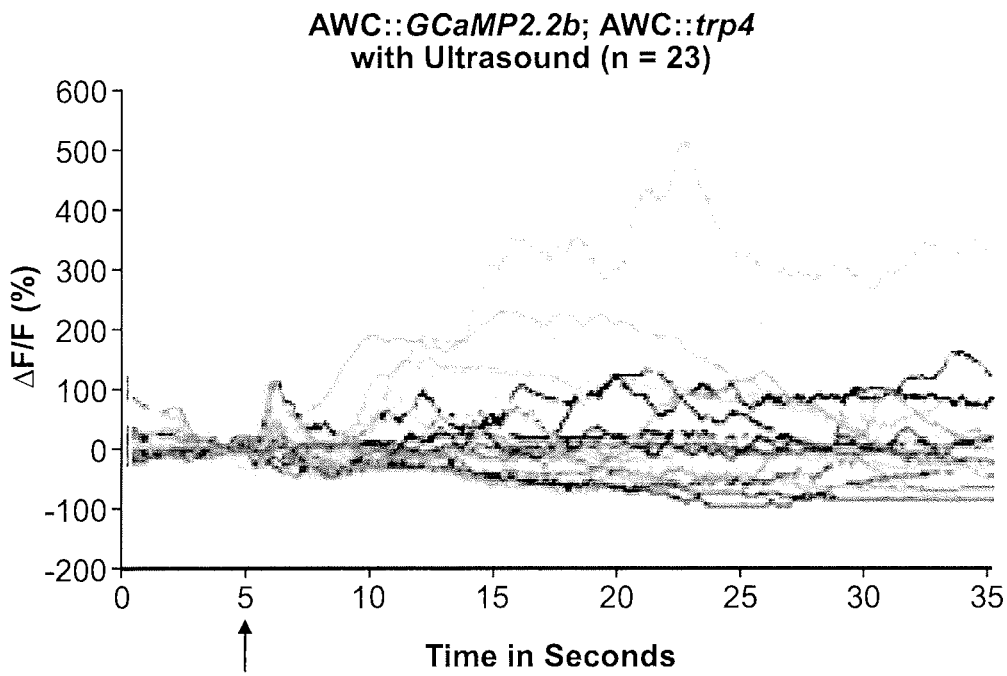

AWC calcium responses to ultrasound stimulus. Ratio of change in fluoresence to baseline fluorescence in AWC neurons expressing the calcium sensor, GCaMP2.2b (n=20). Of these 23 animals tested, 3 reached the baseline

FIG. 15C

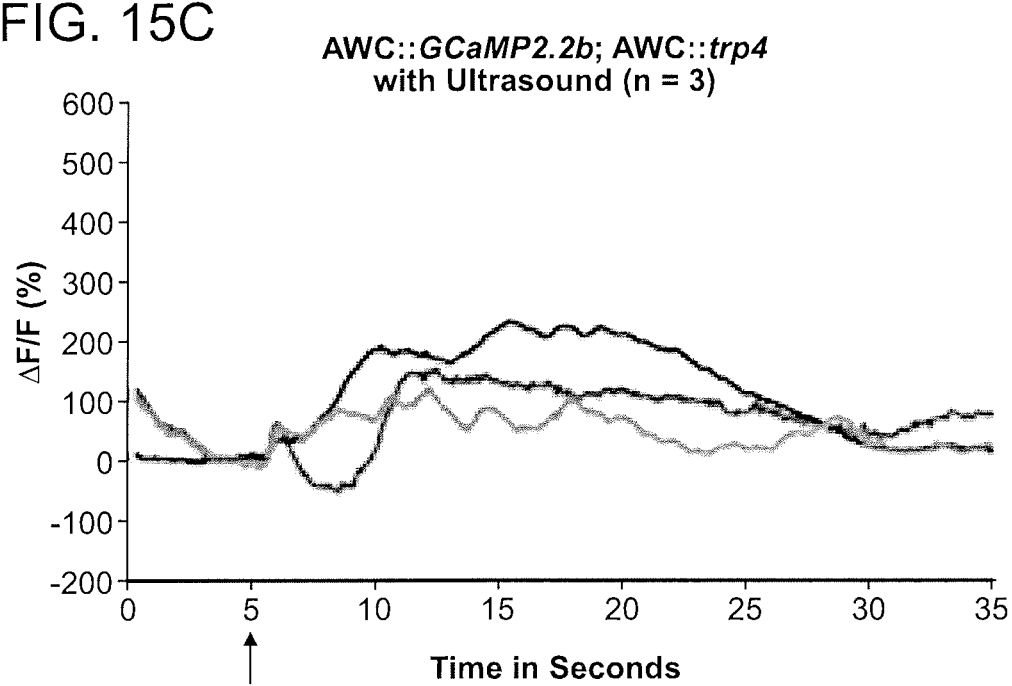

AWC calcium responses to ultrasound stimulus. Ratio of change in fluoresence to baseline fluorescence in AWC neurons expressing the calcium sensor, GCaMP2.2b (n=20). AWC calcuim responses without ultrasound stimulus in wild-type (n=10)

FIG. 15D

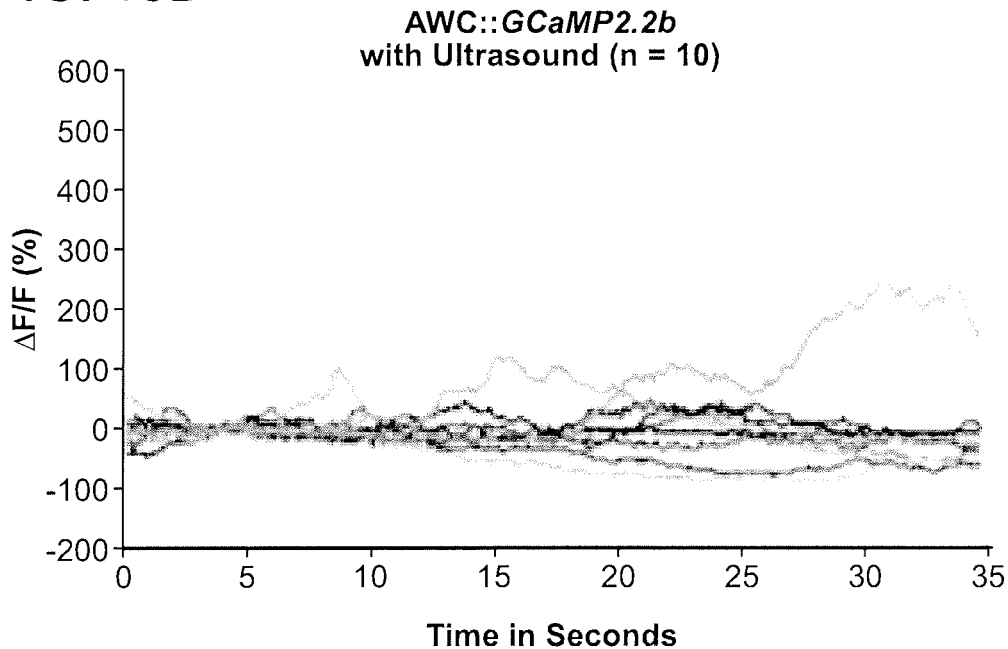

AWC calcium responses to ultrasound stimulus. Ratio of change in fluoresence to baseline fluorescence in AWC neurons expressing the calcium sensor, GCaMP2.2b (n=20) and *AWC::trp-4* transgenics (n=6)

FIG. 15E

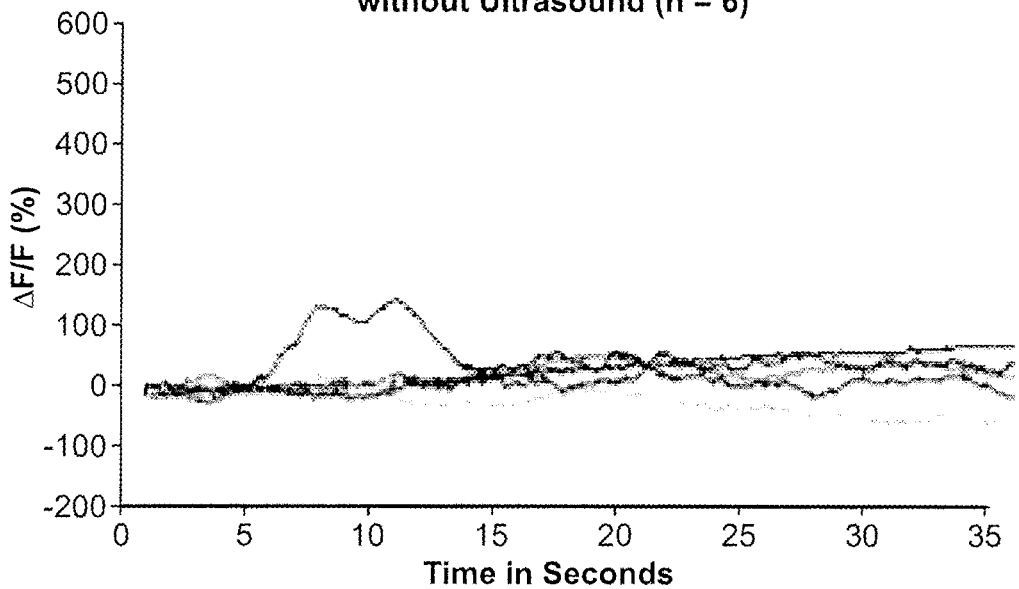

AWC calcium responses to ultrasound stimulus. Ratio of change in fluoresence to baseline fluorescence in AWC neurons expressing the calcium sensor, GCaMP2.2b (n=20). Each color represents the response of an individual neuron to ultrasound stimulus presented at t=5 seconds.

FIG. 15F

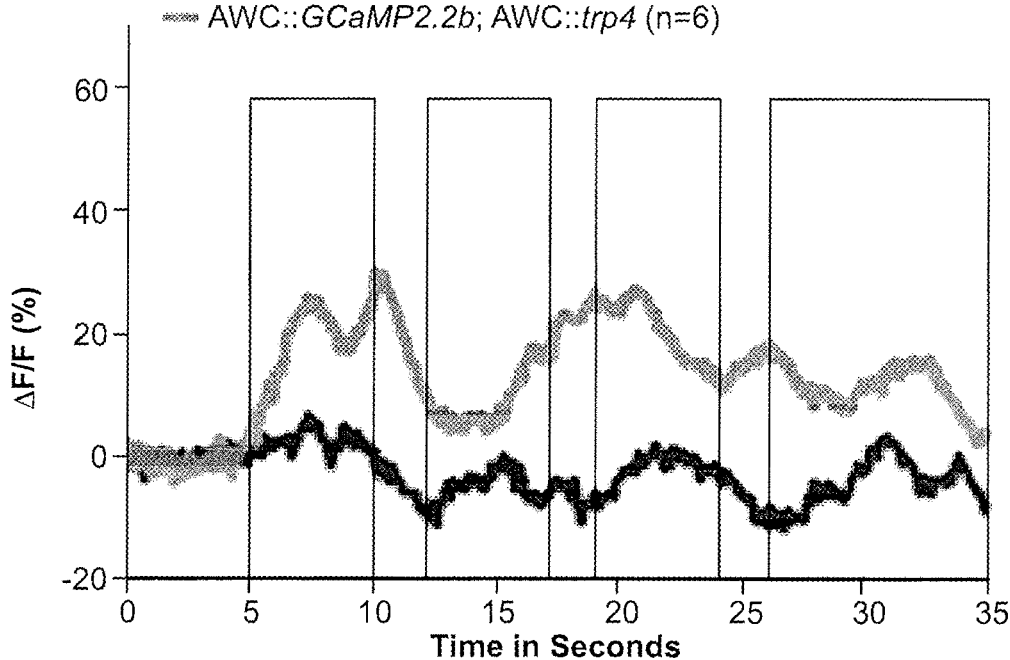

AWC calcium responses to ultrasound stimulus. Ratio of change in fluoresence to baseline fluorescence in AWC neurons expressing the calcium sensor, GCaMP2.2b (n=20). Average AWC calcium responses without ultrasound stimulus in wild-type and AWC::trp-4 transgenics.

AWC calcium responses to ultrasound stimulus. Ratio of change in fluoresence to baseline fluorescence in AWC neurons expressing the calcium sensor, GCaMP2.2b (n=20). Average AWC calcium data binned similarly to the data shown in Fig. 5F. Microbubbles are included in all AWC calcium recordings.

SEQUENCE LISTING

<160> NUMBER OF SEQ ID NOS: 3

<210> SEQ ID NO 1
<211> LENGTH: 1924
<212> TYPE: PRT
<213> ORGANISM: Caenorhabditis elegans

<400> SEQUENCE: 1

Met Asp Ser Pro Arg Gly Gly Ile Leu Gly Arg Ala Leu Arg Glu Ala
1               5                   10                  15

Ser Gln Ser Thr Arg Gln Glu Asn Asp Val Asp Met Asp Gln Val Pro
            20                  25                  30

Val Arg Gln Met Asn Arg Asp Tyr Gly Gly Ser Arg Arg Thr Gln Met
        35                  40                  45

Asn Pro His Thr Ser Gln Pro Gly Pro Ser His Val Ser Ile Val Asn
    50                  55                  60

Val Pro Glu Arg Gly Gly Pro Thr Ser Ser Thr Ser Thr Thr His Glu
65                  70                  75                  80

Thr Glu His Thr Ala His Arg Thr Glu Ser Gly Arg Phe Ile Arg Arg
                85                  90                  95

Arg Arg Gln Ser Arg Glu Val Thr Thr Thr Thr Thr Arg Pro Tyr Asp
            100                 105                 110

Pro Ala Pro Pro Thr Gln Thr Arg Thr Ser Ser Gly Ser Thr Val Asn
        115                 120                 125

Gly Trp Gly Glu Asn Arg Pro Lys Ser Ala Asp Glu Glu Ile Lys Arg
    130                 135                 140

Arg Arg Arg Ser Gly Gly Gly Ile Leu Ser Arg Gly Leu Arg Glu Met

-continued

```
            145                 150                 155                 160
Asn Lys Met Val Glu Glu Leu Glu Gln Ala Ser Glu Pro Ser Thr
                    165                 170                 175
Arg Lys Gly Ile Leu Gly Thr Ala Leu Lys Asp Met Glu Gly Thr Thr
                180                 185                 190
Tyr Gln Lys Ile Tyr Arg Lys Glu Glu Thr Pro Lys Arg Ser Arg
                195                 200                 205
Ser Phe Asp Asp Gln Glu Met Ser Asn Arg Val Gly Met Ile Glu His
            210                 215                 220
Leu Leu Arg Asp Lys Asp Pro Leu Glu Leu Gln Gln Leu Gly Leu Thr
225                 230                 235                 240
Asp Leu Leu Thr Thr Asp Thr Ile Pro Thr Asp Arg Pro Pro Leu Arg
                    245                 250                 255
Arg Ser Ser Thr His Leu Gln Ile Gly Lys Asn Ser Arg Ile Ile Phe
                260                 265                 270
Val Pro Lys Gln Pro Ser Arg Asp Ser Val Thr Pro Pro Asp Arg Leu
            275                 280                 285
Leu Gly Lys Pro Leu Phe Arg Glu Ser Leu Thr Ser His Ala Ser Ser
            290                 295                 300
His Glu Glu Met Ser Ser Glu Asp Leu Ala Met Ala Asp Pro Gln Thr
305                 310                 315                 320
Lys Ile Leu Tyr Phe Ala Lys Arg Asp Glu Trp Ala Asn Val Glu Ser
                    325                 330                 335
Glu Ile Glu Thr Ile Lys Arg Ser Asp Phe Ser Met Ala Asp Asn His
                340                 345                 350
Gly Phe Thr Ala Phe Leu Leu Ala Val Lys Ala Gly Lys Asp Gln Ile
            355                 360                 365
Val Asp Lys Met Ile Arg Lys Gly Ala Arg Val Asp Tyr Ser Thr Lys
            370                 375                 380
Asp Gly Arg Asn Ala Thr His Ile Ala Ala Met Tyr Ser Gly Val Glu
385                 390                 395                 400
Thr Leu Glu Leu Ile Leu Lys Arg Tyr Ser Glu Leu Leu Arg Lys Gly
                    405                 410                 415
Ala Gly Pro Lys Lys Gln Leu Ala Ile His Val Ala Cys Glu Arg Lys
                420                 425                 430
Ser Lys Lys Ala Phe Pro Ile Val Lys Arg Ile Leu Glu Asp Thr Asp
            435                 440                 445
Gln Arg Met Ala Glu Asp Gly Asp Gly Ser Leu Pro Ile His Leu Ala
            450                 455                 460
Phe Lys Phe Gly Asn Val Asn Ile Val Glu Leu Leu Leu Ser Gly Pro
465                 470                 475                 480
Ser Asp Glu Gln Thr Arg Lys Ala Asp Gly Asn Gly Asp Thr Leu Leu
                    485                 490                 495
His Leu Ala Ala Arg Ser Gly Asn Ile Glu Ala Val Arg Thr Ala Ile
                500                 505                 510
Ala Ala Gly Cys Asp Asn Ala Asn Val Gln Asn Arg Val Gly Arg Thr
            515                 520                 525
Pro Leu His Glu Val Ala Glu Val Gly Asp Gln Asn Met Leu Lys Ile
            530                 535                 540
Met Phe Lys Leu Arg Ala Asp Ala Asn Ile His Asp Lys Glu Asp Lys
545                 550                 555                 560
Thr Pro Val His Val Ala Ala Glu Arg Gly Asp Thr Ser Met Val Glu
                    565                 570                 575
```

```
Ser Leu Ile Asp Lys Phe Gly Ser Ile Arg Ala Arg Thr Arg Asp
        580                 585                 590

Gly Ser Thr Leu Leu His Ile Ala Ala Cys Ser Gly His Thr Ser Thr
            595                 600                 605

Ala Leu Ala Phe Leu Lys Arg Gly Val Pro Leu Phe Met Pro Asn Lys
        610                 615                 620

Lys Gly Ala Leu Gly Leu His Ser Ala Ala Ala Gly Phe Asn Asp
625                 630                 635                 640

Val Val Lys Met Leu Ile Ala Arg Gly Thr Asn Val Asp Val Arg Thr
                645                 650                 655

Arg Asp Asn Tyr Thr Ala Leu His Val Ala Val Gln Ser Gly Lys Ala
            660                 665                 670

Ser Val Val Glu Thr Leu Leu Gly Ser Gly Ala Asp Ile His Val Lys
        675                 680                 685

Gly Gly Glu Leu Gly Gln Thr Ala Leu His Ile Ala Ala Ser Leu Asn
    690                 695                 700

Gly Ala Glu Ser Arg Asp Cys Ala Met Met Leu Leu Lys Ser Gly Gly
705                 710                 715                 720

Gln Pro Asp Val Ala Gln Met Asp Gly Glu Thr Cys Leu His Ile Ala
                725                 730                 735

Ala Arg Ser Gly Asn Lys Asp Ile Met Arg Leu Leu Leu Asp Glu Asn
            740                 745                 750

Ala Asp Ser Lys Ile Ser Ser Lys Ile Gly Glu Thr Pro Leu Gln Val
        755                 760                 765

Ala Ala Lys Ser Cys Asn Phe Glu Ala Ala Ser Met Ile Leu Lys His
    770                 775                 780

Leu Ser Glu Val Leu Thr Gln Glu Gln Leu Lys Glu His Val Asn His
785                 790                 795                 800

Arg Thr Asn Asp Gly Phe Thr Ala Leu His Tyr Ala Ala Glu Ile Glu
                805                 810                 815

Gln Arg Gln Leu His Phe Pro Gly Glu Asp Ala Lys Leu Val Asn Leu
            820                 825                 830

Leu Ile Asp Tyr Gly Gly Met Val Glu Met Pro Ser Leu Asn Ala Asn
        835                 840                 845

Glu Thr Ala Met His Met Ala Ala Arg Ser Gly Asn Gln Ala Val Leu
    850                 855                 860

Leu Ala Met Val Asn Lys Ile Gly Ala Gly Ala Val Gln Ile Val Gln
865                 870                 875                 880

Asn Lys Gln Ser Lys Asn Gly Trp Ser Pro Leu Leu Glu Ala Cys Ala
                885                 890                 895

Arg Gly His Ser Gly Val Ala Asn Ile Leu Leu Lys His His Ala Arg
            900                 905                 910

Ile Asp Val Phe Asp Glu Met Gly Arg Thr Ala Leu His Leu Ala Ala
        915                 920                 925

Phe Asn Gly His Leu Ser Leu Val His Leu Leu Leu Gln His Lys Ala
    930                 935                 940

Phe Val Asn Ser Lys Ser Lys Thr Gly Glu Ala Pro Leu His Leu Ala
945                 950                 955                 960

Ala Gln His Gly His Val Lys Val Val Asn Val Leu Val Gln Asp His
                965                 970                 975

Gly Ala Ala Leu Glu Ala Ile Thr Leu Asp Asn Gln Thr Ala Leu His
        980                 985                 990
```

```
Phe Ala Ala Lys Phe Gly Gln Leu Ala Val Ser Gln Thr Leu Leu Ala
        995                 1000                1005

Leu Gly Ala Asn Pro Asn Ala Arg Asp Asp Lys Gly Gln Thr Pro
    1010                1015                1020

Leu His Leu Ala Ala Glu Asn Asp Phe Pro Asp Val Val Lys Leu
    1025                1030                1035

Phe Leu Lys Met Arg Asn Asn Asn Arg Ser Val Leu Thr Ala Ile
    1040                1045                1050

Asp His Asn Gly Phe Thr Cys Ala His Ile Ala Ala Met Lys Gly
    1055                1060                1065

Ser Leu Ala Val Val Arg Glu Leu Met Met Ile Asp Lys Pro Met
    1070                1075                1080

Val Ile Gln Ala Lys Thr Lys Thr Leu Glu Ala Thr Thr Leu His
    1085                1090                1095

Met Ala Ala Ala Gly Gly His Ala Asn Ile Val Lys Ile Leu Leu
    1100                1105                1110

Glu Asn Gly Ala Asn Ala Glu Asp Glu Asn Ser His Gly Met Thr
    1115                1120                1125

Ala Leu His Leu Gly Ala Lys Asn Gly Phe Ile Ser Ile Leu Glu
    1130                1135                1140

Ala Phe Asp Lys Ile Leu Trp Lys Arg Cys Ser Arg Lys Thr Gly
    1145                1150                1155

Leu Asn Ala Leu His Ile Ala Ala Phe Tyr Gly Asn Ser Asp Phe
    1160                1165                1170

Val Asn Glu Met Leu Lys His Val Gln Ala Thr Val Arg Ser Glu
    1175                1180                1185

Pro Pro Ile Tyr Asn His His Val Asn Lys Glu Phe Ser Thr Glu
    1190                1195                1200

Tyr Gly Phe Thr Pro Leu His Leu Ala Ala Gln Ser Gly His Asp
    1205                1210                1215

Ser Leu Val Arg Met Leu Leu Asn Gln Gly Val Gln Val Asp Ala
    1220                1225                1230

Thr Ser Thr Thr Met Asn Val Ile Pro Leu His Leu Ala Ala Gln
    1235                1240                1245

Gln Gly His Ile Ala Val Val Gly Met Leu Leu Ser Arg Ser Thr
    1250                1255                1260

Gln Gln Gln His Ala Lys Asp Trp Arg Gly Arg Thr Pro Leu His
    1265                1270                1275

Leu Ala Ala Gln Asn Gly His Tyr Glu Met Val Ser Leu Leu Ile
    1280                1285                1290

Ala Gln Gly Ser Asn Ile Asn Val Met Asp Gln Asn Gly Trp Thr
    1295                1300                1305

Gly Leu His Phe Ala Thr Arg Ala Gly His Leu Ser Val Val Lys
    1310                1315                1320

Leu Phe Ile Asp Ser Ser Ala Asp Pro Leu Ala Glu Thr Lys Glu
    1325                1330                1335

Gly Lys Val Pro Leu Cys Phe Ala Ala Ala His Asn His Ile Glu
    1340                1345                1350

Cys Leu Arg Phe Leu Leu Lys Gln Lys His Asp Thr His Gln Leu
    1355                1360                1365

Met Glu Asp Arg Lys Phe Ile Phe Asp Leu Met Val Cys Gly Lys
    1370                1375                1380

Thr Asn Asp Asn Glu Pro Leu Gln Glu Phe Ile Leu Gln Ser Pro
```

-continued

```
            1385                1390                1395
Ala Pro Ile Glu Thr Ala Val Lys Leu Ser Ala Leu Tyr Arg Asp
            1400                1405                1410
Met Ser Glu Lys Glu Lys Glu Arg Ala Lys Asp Leu Leu Asn Val
            1415                1420                1425
Ala Val Phe Ser Glu Asn Met Ala Val Glu Leu Leu Gly Ile Thr
            1430                1435                1440
Ala Thr Glu Tyr Asn Ala Ala Leu Leu Leu Lys Ala Lys Asp Asn
            1445                1450                1455
Arg Gly Arg Pro Leu Leu Asp Val Leu Ile Glu Asn Glu Gln Lys
            1460                1465                1470
Glu Val Val Ser Tyr Ala Ser Val Gln Arg Tyr Leu Thr Glu Val
            1475                1480                1485
Trp Thr Ala Arg Val Asp Trp Ser Phe Gly Lys Phe Val Ala Phe
            1490                1495                1500
Ser Leu Phe Val Leu Ile Cys Pro Pro Ala Trp Phe Tyr Phe Ser
            1505                1510                1515
Leu Pro Leu Asp Ser Arg Ile Gly Arg Ala Pro Ile Ile Lys Phe
            1520                1525                1530
Val Cys His Ile Val Ser His Val Tyr Phe Thr Ile Leu Leu Thr
            1535                1540                1545
Ile Val Val Leu Asn Ile Thr His Lys Met Tyr Glu Val Thr Ser
            1550                1555                1560
Val Val Pro Asn Pro Val Glu Trp Leu Leu Leu Trp Leu Ser
            1565                1570                1575
Gly Asn Leu Val Ser Glu Leu Ser Thr Val Gly Gly Gly Ser Gly
            1580                1585                1590
Leu Gly Ile Val Lys Val Leu Ile Leu Val Leu Ser Ala Met Ala
            1595                1600                1605
Ile Ala Val His Val Leu Ala Phe Leu Leu Pro Ala Val Phe Leu
            1610                1615                1620
Thr His Leu Asp Asn Asp Glu Lys Leu His Phe Ala Arg Thr Met
            1625                1630                1635
Leu Tyr Leu Lys Asn Gln Leu Phe Ala Phe Ala Leu Leu Phe Ala
            1640                1645                1650
Phe Val Glu Tyr Leu Asp Phe Leu Thr Val His His Leu Phe Gly
            1655                1660                1665
Pro Trp Ala Ile Ile Ile Arg Asp Leu Met Tyr Asp Leu Ala Arg
            1670                1675                1680
Phe Leu Val Ile Leu Met Leu Phe Val Ala Gly Phe Thr Leu His
            1685                1690                1695
Val Thr Ser Ile Phe Gln Pro Ala Tyr Gln Pro Val Asp Glu Asp
            1700                1705                1710
Ser Ala Glu Leu Met Arg Leu Ala Ser Pro Ser Gln Thr Leu Glu
            1715                1720                1725
Met Leu Phe Phe Ser Leu Phe Gly Leu Val Glu Pro Asp Ser Met
            1730                1735                1740
Pro Pro Leu His Leu Val Pro Asp Phe Ala Lys Ile Ile Leu Lys
            1745                1750                1755
Leu Leu Phe Gly Ile Tyr Met Met Val Thr Leu Ile Val Leu Ile
            1760                1765                1770
Asn Leu Leu Ile Ala Met Met Ser Asp Thr Tyr Gln Arg Ile Gln
            1775                1780                1785
```

```
Ala Gln Ser Asp Lys Glu Trp Lys Phe Gly Arg Ala Ile Leu Ile
    1790            1795                1800

Arg Gln Met Asn Lys Lys Ser Ala Thr Pro Ser Pro Ile Asn Met
1805            1810                1815

Leu Thr Lys Leu Ile Ile Val Leu Arg Val Ala Trp Arg Asn Arg
1820            1825                1830

Leu Arg Cys Met Thr Arg Lys Ala Gln Asp Asp Leu Arg Phe Glu
1835            1840                1845

Glu Asn Ile Asp Ala Phe Ser Met Gly Gly Gln Gln Gly Arg
1850            1855                1860

Gln Ser Pro Thr Asn Glu Gly Arg Glu Gly Gln Gln Glu Leu Gly
1865            1870                1875

Asn Ser Ala Asp Trp Asn Ile Glu Thr Val Ile Asp Trp Arg Lys
1880            1885                1890

Ile Val Ser Met Tyr Tyr Gln Ala Asn Gly Lys Leu Thr Asp Gly
1895            1900                1905

Arg Thr Lys Glu Asp Val Asp Leu Ala Met Ala Val Pro Thr Ser
1910            1915                1920

Phe

<210> SEQ ID NO 2
<211> LENGTH: 5775
<212> TYPE: DNA
<213> ORGANISM: Caenorhabditis elegans

<400> SEQUENCE: 2
atggattcgc cacgtggcgg aatcctggga gagctttac gagaagcatc acaatcgact      60
aggcaagaaa atgatgttga tatggatcag gtacccgtac ggcagatgaa cagggattac     120
ggtggatcca ggaggactca gatgaatccc cacacctccc aacctggtcc atctcatgta     180
tcaattgtaa atgtcccaga acgcggagga cccacatctt ccacatcaac cacacatgag     240
acagagcaca cggcacatag gacagagtcc gggaggttta tcagacgccg tcgccaatct     300
cgagaggtta ccaccacaac cacaagaccc tatgaccccg ctcctccaac ccagacccga     360
acaagctccg gctcaacagt aaatggatgg ggggagaatc gaccgaaatc tgctgatgag     420
gagatcaaac ggcggcgaag aagtggcggg ggaatcctgt ctcgcgggct tcgagaaatg     480
aacaaaatgg tggaagagtt ggagcaagca agtgaagagc aagtaccag aagggaatt     540 ctgggtactg cgttaaagga tatggaaggg accacttatc aaaagattta caggaaaagg     600
gaggaaactc ccaagcgctc ccgttcattt gacgatcagg agatgtcgaa tcgagtagga     660
atgatcgagc acttgctccg agacaaggat ccttttggagc ttcagcagtt gggattaacc     720
gacctcctca ccaccgacac catcccaact gaccgaccac ccctccgccg atcctcgacc     780
catctccaaa tcggaaagaa ctcacggatc atcttcgttc gaaacaacc atcccgtgat     840 tcagtcaccc cgccggatcg tcttctcggg aaacctctgt ttcgagagag tctcacctcc     900
cacgcatcgt ctcatgagga aatgtcgagt gaggacttgg caatggcgga tcctcagacg     960
aagattttgt atttcgcgaa gagagatgag tgggcgaatg tggagtctga gatagagact   1020
atcaagcgga gtgattttag tatggctgat aatcacggct tcaccgcctt cctcctagcc   1080
gtcaaagctg gcaaggatca aatcgtagac aagatgatcc gaaaaggtgc tcgagtggac   1140
tatagcacta aagatggccg taacgcgact catattgccg ccatgtactc cggagttgaa   1200
actcttgagc ttatcctcaa gcgatactct gagctgctcc gaaaaggtgc ggggcctaaa   1260
```

```
aagcagctgg caatccatgt ggcttgcgag agaaaatcca agaaagcatt tccaattgtg    1320
aagcggattt tggaagatac tgatcaaaga atggcagagg atggggatgg atccttgccg    1380
atacacttgg cattcaagtt tgggaatgtt aatattgtgg agcttctgct aagtgggcct    1440
tcggatgaac aaaccaggaa agctgatgga aacggggata ccttgcttca tttggccgct    1500
cggagtggga atatcgaagc ggttcggaca gcgattgcgg ctggatgtga taatgcgaat    1560
gtgcagaata gggtgggaag gacgccgcta catgaggtag ccgaagtcgg agatcaaaat    1620
atgctaaaaa tcatgttcaa actccgcgcc gacgccaaca tccatgataa ggaggacaag    1680
actccggtac acgttgcagc ggagcgaggt gacacttcga tggtcgagtc actaattgac    1740
aagtttggtg gctcaattcg cgctaggacc cgtgatgggt cgacgcttct gcatattgcc    1800
gcatgttcag acatactag caccgcattg gcgttttga agagaggagt cccctcttc    1860 atgcccaaca aaaaggagc cctgggtctt cactccgcag cagctgctgg cttcaacgac    1920
gtcgtcaaaa tgctcattgc tcggggtact aatgtagatg tccgtacacg agacaactac    1980
accgctctcc acgtagcggt tcaatctggc aaggcttcgg ttgtagagac cctgctggga    2040
agtggtgcag acattcatgt gaagggcggg gaactaggac aaactgcact gcacattgcg    2100
gcaagcttga atggagccga gagtcgggat tgtgcgatga tgttgctgaa aagtggaggg    2160
cagccggatg ttgcacaaat ggatggggag acttgtctgc atattgctgc caggagtggg    2220
aataaggata tcatgaggct cctgcttgac gagaacgccg actcgaaaat aagctcaaag    2280
atcggagaga cacccctcca ggtggccgcc aagtcatgca attttgaagc agcatcaatg    2340
attttgaagc acctttcgga agttctgacc caagaacagc ttaaggaaca tgtcaatcat    2400
agaaccaatg acggcttcac agctcttcac tacgccgctg aaatcgagca gcgccagtta    2460
cactttccag agaagatgc caagctagta aatcttctga tcgactacgg tggaatggta    2520
gaaatgccat cactcaatgc aaatgagacg gcgatgcata tggcggcaag atccggaaat    2580
caagctgtac tcctggcgat ggtcaataag atcggagccg gtgcggtgca aatcgtgcag    2640
aacaagcaga gcaagaacgg atggtcaccg ctgttggaag catgtgccag agggcattct    2700
ggagtggcga atattttgtt gaagcaccac gcccgtattg atgtattcga tgaaatgggc    2760
cgtactgctc tgcacctggc agcttttcaat gggcatctct ccctggttca ccttcttctg    2820
cagcacaaag cattcgtgaa cagtaaatcg aaaaccggag aggcaccgct ccacttagca    2880
gctcagcatg tcatgtgaa ggtggtgaat gtcctggtgc aggatcatgg tgcagcgctg    2940
gaggcaatta cgctggataa tcagacagcc ctccactttg ccgcaaaatt cggtcagcta    3000
gctgtgagtc aaacccttct ggctctcgga gcaaacccca atgcacgtga cgacaagggt    3060
caaacccctc tccatctggc agctgagaat gacttcccg acgttgtgaa gctcttcctg    3120
aaaatgagaa ataacaaccg gagtgtgttg accgcaattg atcataatgg attcacctgc    3180
gcacatattg ctgcgatgaa gggttcccta gccgtggtcc gtgagcttat gatgatcgac    3240
aagcctatgg taatccaggc aaagaccaaa acactggaag ccactacact tcatatggca    3300
gctgcgggag tcacgcgaa cattgtgaag attctgctgg agaatggagc aaacgcggaa    3360
gatgagaatt cgcacggaat gactgctctc caccttggcg ccaaaaacgg attcatatcg    3420
attttggagg cattcgataa gatcctatgg aaacggtgtt cgagaaagac cggtctcaac    3480
gctctccaca tcgctgcgtt ctacggaaat tcggatttcg tcaatgaaat gctcaagcac    3540
gtacaagcaa cagtccgttc cgagccgccc atctacaatc accatgtcaa taaggaattc    3600
```

-continued

```
tcaactgaat acggcttcac acctctccat ttagccgctc aaagtggaca cgacagtctt      3660
gtgcggatgc ttctgaatca gggagtgcaa gttgacgcga ccagtactac aatgaacgtg      3720 atcccctcc atctggctgc ccagcaaggc cacatcgcag tggtaggaat gctcctgtcc       3780
agatctactc agcagcagca cgccaaggat tggagaggca ggaccccgct ccacctagcc      3840
gctcagaatg ccactacga gatggtctca cttctcattg ctcagggatc taacatcaat      3900
gtcatggatc agaatggctg gactggtctt cactttgcca ctcgtgccgg cacctgagt       3960 gtcgtcaagc tgttcatcga tagttcagcg gatccattgg cggagaccaa ggagggcaaa     4020
gttccattgt gctttgctgc agctcataat catatagaat gtcttcgatt cctcctgaaa      4080
cagaagcatg acacacatca attgatgaaa gatcggaagt tcatattcga cttgatggtt      4140
tgtggtaaaa ccaatgacaa tgagcctcta caagagttta ttcttcaatc acctgctcca     4200
attgagacgg cagtcaagtt gtccgcgttg tacagagata tgtcggagaa ggagaaggag      4260
agggcgaagg atctgttgaa tgtggcagtg ttcagtgaga atatggctgt ggagttgtta     4320
gggatcaccg ccaccgaata caatgccgct cttctcctga aggctaagga caatcgaggc     4380
cggcccctac tagatgttct cattgaaaat gagcagaaag aagtagtctc ctacgcgtct      4440
gtccaacgct acctgacaga gtatggact gcccgtgtcg actggtcatt cggaaagttt       4500
gtcgcattct ccctcttcgt gctaatatgc ccccggcat ggttctactt ctcacttcca      4560
ctggatagtc ggatcggaag agctccgatt attaaatttg tgtgccatat cgtgtctcat      4620
gtctatttta cgatactgct gacaattgtg gtgttgaata ttacacataa gatgtacgaa     4680
gtaacttcgg tggttccaaa ccctgtggaa tggctcctgt tgctctggct ctctggaaat      4740
ctggtctccg aactctccac tgtcggtgga ggatctggcc taggaatcgt aaaggtccta     4800
atcctagtcc tttccgcgat ggcgatagcc gtccatgtcc tagccttcct gctcccggca    4860
gtattcctaa cccacctgga taacgatgaa aagctacatt tcgcccggac aatgctttat     4920
ttgaaaaatc aacttttcgc cttttgccctg ctatttgctt ttgtagagta cctggatttc    4980
ctgacagtgc atcatttgtt cggtccctgg gcgatcatta ttcgagatct aatgtatgat    5040
ttggcccgtt tccttgtgat cctgatgttg ttcgtggcgg gcttcacact ccacgtgacg     5100
agtatcttcc agcctgccta ccagcctgtc gacgaggaca gcgccgagct gatgcgtctg     5160
gcctccccgt ctcaaaccct cgaaatgctc ttcttctcgc tcttcggact cgtcgagccc     5220
gattcaatgc ccccgctcca tctagttcca gattttgcaa aaatcatctt aaaacttcta     5280
ttcggaatct acatgatggt caccttgatt gtgctgatca acttgctgat tgctatgatg    5340
tctgacacct accaacgaat tcaggcacag tcggataagg aatggaagtt cggaagagct    5400
attctgatca gacagatgaa taagaaaagc gccacgccgt cgccgataaa tatgttaaca    5460
aagttgataa ttgtgctgag ggtagcctgg cggaatcggt tgagatgcat gacccgaaaa     5520
gcccaagacg atcttcgctt cgaggagaac atcgacgcgt tctccatggg tggcggccag    5580
cagggaaggc aaagtccgac caatgaagga agagaaggcc agcaagagct tggtaactcg     5640
gctgactgga acatcgagac agtcatcgac tggaggaaga ttgtttcaat gtactatcag    5700
gcgaatggga agcttacaga cgggcgaacc aaagaggatg tggatttggc aatggcagta    5760
cctactagtt tttag                                                      5775
```

<210> SEQ ID NO 3
<211> LENGTH: 5803
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gtttaaacgg cgcgccggta ccatgaatcc tcacacttct cagccagggc caagccatgt      60
ctccattgtc aacgtgccag agcgggggg accaacctcc tcaacctcca ccacacacga      120
gaccgaacac acagcccatc gcacagagag cggccgattc atccggagaa ggcgccagtc     180
cagagaagtg actaccacaa ctaccaggcc ctacgatcct gcaccaccta cccagacaag     240
aactagctcc ggctccaccg tgaatgggtg gggcgagaac aggcccaagt ctgccgacga     300
ggagatcaag cgacggagaa ggagtggcgg gggaatcctg tcaagagggc tgagggagat     360
gaacaagatg gtggaggaac tggaacaggc ctctgaggaa cccagtacac gcaagggcat     420
tctggggact gctctgaaag acatggaggg cacaacttac cagaagatct atcggaaaag     480
agaggaaacc cctaaaaggt ctcgcagttt cgacgatcag gagatgagca acagagtggg     540
gatgatcgaa catctgctga gggacaagga ccccctggag ctccagcagc tgggactgac     600
agacctgctg accacagata ctattccaac cgaccgacca ccactgcgcc gatctagtac     660
tcacctccag atcggcaaga acagccggat cattttcgtg ccaaaacagc ccagccgcga     720
ttccgtcact cctccagacc gactgctggg caagcctctg tttcgggagt ctctgaccag     780
tcacgcctca agccatgagg aaatgtcctc tgaagatctg gctatggccg accccagac     840
caagatcctg tacttcgcca acgcgacga gtgggctaat gtggagtccg aaattgagac     900
aatcaagcgg tcagcttca gcatggccga caaccacgga ttcactgctt ttctgctggc     960
agtgaaggcc ggcaaagacc agattgtcga taagatgatc cgaaaaggag cacgggtgga    1020
ttattctacc aaggacggca gaaacgccac acatattgcc gctatgtaca gtggcgtgga    1080
gacactggaa ctgatcctga gaggtattc agagctgctg cgcaaaggcg ccgggcctaa    1140
gaaacagctg gcaatccacg tggcctgcga aggaagtcc aagaaagcct tcccaattgt    1200
gaaaagaatc ctggaggaca ccgatcagag gatggctgaa gacggagatg gctctctgcc    1260
cattcacctg gcattcaaat tgggaatgt gaacatcgtc gagctgctgc tgtccggacc    1320
ttctgatgaa cagactagaa aggccgacgg gaatggagat accctgctgc atctggcagc    1380
acgctccgga acattgagg ctgtgcgaac cgcaatcgcc gccggatgcg acaatgccaa    1440
cgtgcagaac cgcgtcgggc gaacaccact gcacgaggtg gctgaagtcg agatcagaa    1500
tatgctgaag attatgttca aactgcgcgc agacgccaac atccatgaca aggaggataa    1560
aacaccagtg cacgtcgccg ctgagcgagg cgatacttca atggtggaaa gcctgattga    1620
caagtttggc gggtccatcc gagcccggac aagagatggc tctactctgc tgcatatcgc    1680
agcctgttcc gggcacacct ctacagctct ggcattcctg aagagaggcg tgcctctgtt    1740
tatgccaaat aagaaaggag ccctgggact gcatagcgcc gccgccgccg gcttcaacga    1800
cgtggtcaag atgctgatcg ccaggggaac aaatgtggat gtcaggaccc gcgacaacta    1860
cacagccctg cacgtggctg tccagagtgg caaggccagc gtggtcgaga ctctgctggg    1920
cagcggagca gatattcatg tgaagggagg agaactggga cagaccgccc tgcacatcgc    1980
agccagcctg aacggggcag agtccaggga ctgcgccatg atgctgctga aaagcggggg    2040
acagcctgat gtggcccaga tggacggaga aacctgtctg cacattgctg cacggtctgg    2100
caataaggat atcatgagac tgctgctgga cgagaacgcc gatagtaaga ttagttcaaa    2160
aatcggcgaa actccactcc aggtggccgc taagtcttgc aacttcgagg cagccagtat    2220
```

```
gatcctgaaa cacctgtcag aagtgctgac ccaggagcag ctgaaggaac acgtcaatca    2280
tagaactaac gacggcttca ccgccctgca ttacgccgcc gagattgagc agaggcagct    2340
gcactttcca ggggaggatg ccaagctggt gaatctgctg atcgactatg cgggatggt     2400 cgagatgccc tcactgaatg caaacgaaac cgccatgcac atggccgcta aagcggaaa     2460 tcaggctgtg ctgctggcaa tggtcaacaa gattggagcc ggcgctgtgc agatcgtcca    2520
gaataagcag tcaaaaaacg gctggagccc actgctggag gcatgtgcca gggggcatag    2580
cggagtggct aacattctgc tgaagcacca tgcacgcatc gacgtgttcg atgaaatggg    2640
gcgaacagcc ctgcacctgg cagcctttaa tggacacctg agcctggtgc atctgctgct    2700
ccagcacaaa gccttcgtca actcaaagag caaaaccgga gaggctccac tgcacctggc    2760
tgcacagcac gggcatgtga aggtggtcaa tgtgctggtc caggatcatg gggccgctct    2820
ggaggccatc acactggaca accagactgc tctgcacttc gcagccaaat tggacagct    2880 ggccgtgagc cagacactgc tggctctggg ggcaaatcct aacgctagag acgataaggg    2940
acagactcca ctgcacctgg ccgccgagaa cgacttcccc gatgtggtca agctgtttct    3000
gaaaatgaga aacaataaca ggagcgtgct gacagcaatt gatcataatg cttcacctg     3060 cgcccacatc gccgctatga aaggcagcct ggccgtggtc agggagctga tgatgattga    3120
caagcctatg gtcatccagg caaagactaa aaccctggaa gccactaccc tgcacatggc    3180
agccgctgga ggacacgcca acattgtgaa gatcctgctg gagaatggcg ctaacgcaga    3240
agatgagaac agccacggca tgaccgcact gcacctggga gccaaaaacg gattcatttc    3300
catcctggag gcctttgaca agattctgtg gaagcggtgc agccggaaga cagggctgaa    3360
tgctctgcat atcgcagcct tctacggaaa tagcgacttt gtgaacgaga tgctgaaaca    3420
cgtgcaggcc actgtccgca gtgaaccccc tatctacaat caccatgtga acaaggagtt    3480
ctcaaccgaa tatggcttta cacctctgca tctggctgca cagagcgggc acgattccct    3540
ggtgcggatg ctgctgaatc agggcgtgca ggtcgacgcc accagcacaa ctatgaacgt    3600
gattccactg catctggcag ctcagcaggg acacatcgca gtggtcggaa tgctgctgtc    3660
ccgctctacc cagcagcagc acgctaagga ttggcgagga cggacacccc tgcatctggc    3720
agcccagaac ggccactatg agatggtgag cctgctgatt gcccagggct ccaatatcaa    3780
cgtgatggac cagaatggct ggactggact gcatttcgca acccgggctg acacctgag     3840 cgtggtcaag ctgtttatcg acagctccgc cgatcctctg gctgagacca aggaaggcaa    3900
agtgccactg tgcttcgctg ccgcccacaa ccatattgag tgtctgagat ttctgctgaa    3960
gcagaaacac gatacacatc agctgatgga agataggaag ttcatctttg acctgatggt    4020
gtgcggcaaa actaatgaca acgagcctct ccaggagttc atcctccagt cccccgctcc    4080
tatcgagacc gcagtgaaac tgtctgccct gtacagagat atgagtgaaa aggagaaaga    4140
aagggctaag gacctgctga atgtggcagt ctttttctgag aacatggccg tggaactgct    4200
gggaattaca gcaactgagt ataatgctgc actgctgctg aaggccaaag ataacagagg    4260
caggccactg ctggacgtgc tgatcgagaa cgaacagaaa gaggtggtca gttacgcctc    4320
agtgcagaga tacctgacag aagtgtggac tgctcgggtc gattggtcat cgggaagtt    4380 tgtggcattc agcctgtttg tcctgatttg cccacccgcc tggttctact tttcccctgcc    4440 actggactct aggattggac gcgccccat catcaagttc gtgtgccaca tcgtgtccca    4500
tgtctacttt accattctgc tgacaatcgt ggtcctgaat atcactcaca agatgtatga    4560
```

```
                                                           -continued
ggtgaccagc gtggtcccaa atcccgtcga atggctgctg ctgctgtggc tgtccggcaa    4620
cctggtgagc gagctgtcca ccgtcggagg aggcagcgga ctgggaattg tgaaggtcct    4680
gatcctggtg ctgagcgcaa tggccatcgc agtgcacgtc ctggctttcc tgctgcccgc    4740
agtgtttctg actcatctgg acaatgatga gaagctgcac ttcgcccgca ccatgctgta    4800
cctgaaaaac cagctgttcg cctttgctct gctgttcgct tttgtggaat atctggactt    4860
cctgacagtc caccatctgt ttgggccttg ggctatcatt attagggacc tgatgtacga    4920
tctggcacgg ttcctggtca tcctgatgct gttcgtcgcc ggcttcaccc tgcatgtgac    4980
ctctatcttt cagcccgcct atcagcctgt cgacgaggat agtgctgaac tgatgcggct    5040
ggcaagtccc tcacagaccc tggagatgct gttctttagt ctgttcggcc tggtggaacc    5100
cgattcaatg cctccactgc acctggtgcc tgacttcgcc aagattatcc tgaaactgct    5160
gtttgggatc tacatgatgg tgaccctgat tgtcctgatc aacctgctga ttgctatgat    5220
gtctgataca tatcagcgca tccaggcaca gagtgacaag gagtgaaaat ttggccgggc    5280
cattctgatc agacagatga ataagaaatc tgctacccct agtccaatta acatgctgac    5340
aaaactgatt atcgtgctgc gggtcgcttg gcgcaatcga ctgcggtgta tgacccgaaa    5400
ggcccaggac gatctgcggt tcgaggaaaa catcgacgct ttttcaatgg ggggaggaca    5460
gcagggacga cagagcccta ccaatgaggg acgagaagga cagcaggagc tgggcaattc    5520
cgccgattgg aacattgaaa cagtgatcga ctggagaaag atcgtctcta tgtactatca    5580
ggccaatggc aaactgactg acgggcgaac caaggaggat gtcgatctgg ctatggctgt    5640
ccctacttct ttctgaattc cgataacttg tttattgcag cttataatgg ttacaaataa    5700
agcaatagca tcacaaattt cacaaataaa gcatttttt cactgcattc tagttgtggt    5760
ttgtccaaac tcatcaatgt atcttatcat gtctggcggc cgc                       5803
```

SONOGENIC STIMULATION OF CELLS

CROSS REFERENCE TO RELATED APPLICATIONS

This application claims benefit of U.S. Provisional Application Ser. No. 62/054,600, filed Sep. 24, 2015, the contents of which are incorporated herein by reference.

STATEMENT OF RIGHTS TO INVENTIONS MADE UNDER FEDERALLY SPONSORED RESEARCH

This work was supported by the following grants from the National Institutes of Health, Grant Nos: NIH R01MH096881-03. The government has certain rights in the invention.

BACKGROUND OF THE INVENTION

Understanding how neural circuits generate specific behaviors requires an ability to identify the participating neurons, record and perturb their activity patterns. The best-understood motor circuit, the crab stomatogastric ganglion (STG) has benefited from electrophysiological access to well-defined cell types as well as an ability to manipulate them. A number of approaches have been developed for manipulating neuronal activity using light (optogenetics) or small molecules. While these methods have revealed insights into circuit computations in a number of model systems including mice, they suffer from one drawback: difficulty in delivering stimulus to the target neurons that are present in deeper brain regions. Methods for the non-invasive stimulation of target neurons and other cell types are required.

BRIEF SUMMARY OF THE INVENTION

The invention provides compositions featuring TRP-4 polypeptides and polynucleotides, methods for expressing such polypeptides and polynucleotides in a cell type of interest, and methods for inducing the activation of the TRP-4 polypeptide in neurons and other cell types using ultrasound.

In one aspect, the invention provides a method of stimulating a cell, the method involving contacting a TRP-4 polypeptide expressing cell with ultrasound, thereby stimulating the cell. In one embodiment, the TRP-4 polypeptide comprises the amino acid sequence of SEQ ID NO:1.

In another aspect, the invention provides a method of inducing cation influx in a cell, the method involving expressing a heterologous TRP-4 polypeptide in a cell, and applying ultrasound to the cell, thereby inducing cation influx in the cell. In one embodiment, the cell is a mammalian cell or bacterial cell (e.g, bacterial biofilm). In another embodiment, the TRP-4 polypeptide is encoded by a polynucleotide codon-optimized for expression in the cell. In another embodiment, the cell is muscle cell, cardiac muscle cell, neuron, motor neuron, sensory neuron, interneuron, or insulin secreting cell. In another embodiment, the ultrasound has a frequency of about 0.8 MHz to about 4 MHz. In another embodiment, the ultrasound has a focal zone of about 1 cubic millimeter to about 1 cubic centimeter. In another embodiment, the method further involves contacting the cell with a microbubble prior to applying ultrasound. In another embodiment, the cell is in vitro or in vivo.

In yet another aspect, the invention provides a method of treating a disease or disorder in a subject in need thereof, the method involving expressing in a cell (e.g., muscle cell, cardiac muscle cell, neuron, motor neuron, sensory neuron, interneuron, or insulin secreting cell) of a subject a heterologous nucleic acid molecule encoding a TRP-4 polypeptide; and applying ultrasound to the cell, thereby treating a disease or disorder in the subject. In one embodiment, the disease is a neurological disease selected from Parkinson Disease, depression, obsessive-compulsive disorder, chronic pain, epilepsy and cervical spinal cord injury. In another embodiment, the disorder is muscle weakness.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

By TRP-4 polypeptide is meant a transient receptor potential cation channel capable of conferring ultrasound sensitivity on a neuron and having at least about 85% amino acid identity to SEQ ID NO: 1 or a human ortholog thereof.

SEQ ID NO. 1:
MDSPRGGILGRALREASQSTRQENDVDMDQVPVRQMNRDYGGSRRTQMNP

HTSQPGPSHVSIVNVPERGGPTSSTSTTHETEHTAHRTESGRFIRRRRQS

REVTTTTTRPYDPAPPTQTRTSSGSTVNGWGENRPKSADEEIKRRRRSGG

GILSRGLREMNKMVEELEQASEEPSTRKGILGTALKDMEGTTYQKIYRKR

EETPKRSRSFDDQEMSNRVGMIEHLLRDKDPLELQQLGLTDLLTTDTIPT

DRPPLRRSSTHLQIGKNSRIIFVPKQPSRDSVTPPDRLLGKPLFRESLTS

HASSHEEMSSEDLAMADPQTKILYFAKRDEWANVESEIETIKRSDFSMAD

NHGFTAFLLAVKAGKDQIVDKMIRKGARVDYSTKDGRNATHIAAMYSGVE

TLELILKRYSELLRKGAGPKKQLAIHVACERKSKKAFPIVKRILEDTDQR

MAEDGDGSLPIHLAFKFGNVNIVELLLSGPSDEQTRKADGNGDILLHLAA

RSGNIEAVRTAIAAGCDNANVQNRVGRTPLHEVAEVGDQNMLKIMFKLRA

DANIHDKEDKTPVHVAAERGDTSMVESLIDKFGGSIRARTRDGSTLLHIA

ACSGHTSTALAFLKRGVPLFMPNKKGALGLHSAAAAGFNDVVKMLIARGI

NVDVRTRDNYTALHVAVQSGKASVVETLLGSGADIHVKGGELGQTALHIA

ASLNGAESRDCAMMLLKSGGQPDVAQMDGETCLHIAARSGNKDIMRLLLD

ENADSKISSKIGETPLQVAAKSCNFEAASMILKHLSEVLTQEQLKEHVNH

RTNDGFTALHYAAEIEQRQLHFPGEDAKLVNLLIDYGGMVEMPSLNANET

AMHMAARSGNQAVLLAMVNKIGAGAVQIVQNKQSKNGWSPLLEACARGHS

GVANILLKHHARIDVFDEMGRTALHLAAFNGHLSLVHLLLQHKAFVNSKS

KTGEAPLHLAAQHGHVKVVNVLVQDHGAALEAITLDNQTALHFAAKFGQL

-continued

AVSQTLLALGANPNARDDKGQTPLHLAAENDFPDVVKLFLKMRNNNRSVL

TAIDHNGFTCAHIAAMKGSLAVVRELMMIDKPMVIQAKTKTLEATTLHMA

AAGGHANIVKILLENGANAEDENSHGMTALHLGAKNGFISILEAFDKILW

KRCSRKTGLNALHIAAFYGNSDFVNEMLKHVQATVRSEPPIYNHHVNKEF

STEYGFTPLHLAAQSGHDSLVRMLLNQGVQVDATSTTMNVIPLHLAAQQG

HIAVVGMLLSRSTQQQHAKDWRGRTPLHLAAQNGHYEMVSLLIAQGSNIN

VMDQNGWTGLHFATRAGHLSVVKLFIDSSADPLAETKEGKVPLCFAAAHN

HIECLRFLLKQKHDTHQLMEDRKFIFDLMVCGKINDNEPLQEFILQSPAP

IETAVKLSALYRDMSEKEKERAKDLLNVAVFSENMAVELLGITATEYNAA

LLLKAKDNRGRPLLDVLIENEQKEVVSYASVQRYLTEVWTARVDWSFGKF

VAFSLFVLICPPAWFYFSLPLDSRIGRAPIIKFVCHIVSHVYFTILLTIV

VLNITHKMYEVTSVVPNPVEWLLLLWLSGNLVSELSTVGGGSGLGIVKVL

ILVLSAMAIAVHVLAFLLPAVFLTHLDNDEKLHFARTMLYLKNQLFAFAL

LFAFVEYLDFLTVHHLFGPWAIIIRDLMYDLARFLVILMLFVAGFTLHVT

SIFQPAYQPVDEDSAELMRLASPSQTLEMLFFSLFGLVEPDSMPPLHLVP

DFAKIILKLLFGIYMMVTLIVLINLLIAMMSDTYQRIQAQSDKEWKFGRA

ILIRQMNKKSATPSPINMLTKLIIVLRVAWRNRLRCMTRKAQDDLRFEEN

IDAFSMGGGQQGRQSPTNEGREGQQELGNSADWNIETVIDWRKIVSMYYQ

ANGKLTDGRTKEDVDLAMAVPTSF

For specific proteins described herein (e.g., TRP-4), the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof. In embodiments, the TRP-4 polypeptide is substantially identical to the protein identified by the NCBI reference number Gene ID: GI: 193247904 or a variant or homolog having substantial identity thereto. In embodiments, the TRP-4 polypeptide is the protein as identified by the NCBI sequence reference GI: 193247904. In embodiments, the TRP-4 polypeptide is the protein as identified by the NCBI sequence reference GI:193247904, homolog or functional fragment thereof. In embodiments, the TRP-4 polypeptide includes the amino acid sequence of SEQ ID NO:1. In embodiments, the TRP-4 polypeptide is the amino acid sequence of SEQ ID NO:1.

By "TRP-4 polynucleotide" is meant a nucleic acid molecule encoding a TRP-4 polypeptide. In particular embodiments, the codons of the TRP-4 polynucleotide are optimized for expression in an organism of interest (e.g., optimized for human expression, bacterial expression, murine expression). The sequence of an exemplary TRP-4 polynucleotide is provided herein below

SEQ ID NO: 2:
ATGGATTCGCCACGTGGCGGAATCCTGGGAAGAGCTTTACGAGAAGCATC

ACAATCGACTAGGCAAGAAAATGATGTTGATATGGATCAGGTACCCGTAC

GGCAGATGAACAGGGATTACGGTGGATCCAGGAGGACTCAGATGAATCCC

CACACCTCCCAACCTGGTCCATCTCATGTATCAATTGTAAATGTCCCAGA

ACGCGGAGGACCCACATCTTCCACATCAACCACACATGAGACAGAGCACA

CGGCACATAGGACAGAGTCCGGGAGGTTTATCAGACGCCGTCGCCAATCT

CGAGAGGTTACCACCACAACCACAAGACCCTATGACCCCGCTCCTCCAAC

CCAGACCCGAACAAGCTCCGGCTCAACAGTAAATGGATGGGGGGAGAATC

GACCGAAATCTGCTGATGAGGAGATCAAACGGCGGCGAAGAAGTGGCGGG

GGAATCCTGTCTCGCGGGCTTCGAGAAATGAACAAAATGGTGGAAGAGTT

GGAGCAAGCAAGTGAAGAGCCAAGTACCAGGAAGGGAATTCTGGGTACTG

CGTTAAAGGATATGGAAGGGACCACTTATCAAAAGATTTACAGGAAAAGG

GAGGAAACTCCCAAGCGCTCCCGTTCATTTGACGATCAGGAGATGTCGAA

TCGAGTAGGAATGATCGAGCACTTGCTCCGAGACAAGGATCCTTTGGAGC

TTCAGCAGTTGGGATTAACCGACCTCCTCACCACCGACACCATCCCAACT

GACCGACCACCCCTCCGCCGATCCTCGACCCATCTCCAAATCGGAAAGAA

CTCACGGATCATCTTCGTTCCGAAACAACCATCCCGTGATTCAGTCACCC

CGCCGGATCGTCTTCTCGGGAAACCTCTGTTTCGAGAGAGTCTCACCTCC

CACGCATCGTCTCATGAGGAAATGTCGAGTGAGGACTTGGCAATGGCGGA

TCCTCAGACGAAGATTTTGTATTTCGCGAAGAGAGATGAGTGGGCGAATG

TGGAGTCTGAGATAGAGACTATCAAGCGGAGTGATTTTAGTATGGCTGAT

AATCACGGCTTCACCGCCTTCCTCCTAGCCGTCAAAGCTGGCAAGGATCA

AATCGTAGACAAGATGATCCGAAAAGGTGCTCGAGTGGACTATAGCACTA

AAGATGGCCGTAACGCGACTCATATTGCCGCCATGTACTCCGGAGTTGAA

ACTCTTGAGCTTATCCTCAAGCGATACTCTGAGCTGCTCCGAAAAGGTGC

GGGGCCTAAAAAGCAGCTGGCAATCCATGTGGCTTGCGAGAGAAAATCCA

AGAAAGCATTTCCAATTGTGAAGCGGATTTTGGAAGATACTGATCAAAGA

ATGGCAGAGGATGGGGATGGATCCTTGCCGATACACTTGGCATTCAAGTT

TGGGAATGTTAATATTGTGGAGCTTCTGCTAAGTGGGCCTTCGGATGAAC

AAACCAGGAAAGCTGATGGAAACGGGGATACCTTGCTTCATTTGGCCGCT

CGGAGTGGGAATATCGAAGCGGTTCGGACAGCGATTGCGGCTGGATGTGA

TAATGCGAATGTGCAGAATAGGGTGGGAAGGACGCCGCTACATGAGGTAG

CCGAAGTCGGAGATCAAAATATGCTAAAAATCATGTTCAAACTCCGCGCC

GACGCCAACATCCATGATAAGGAGGACAAGACTCCGGTACACGTTGCAGC

GGAGCGAGGTGACACTTCGATGGTCGAGTCACTAATTGACAAGTTTGGTG

GCTCAATTCGCGCTAGGACCCGTGATGGGTCGACGCTTCTGCATATTGCC

GCATGTTCAGGACATACTAGCACCGCATTGGCGTTTTTGAAGAGGAGT

CCCCCTCTTCATGCCCAACAAAAAAGGAGCCCTGGGTCTTCACTCCGCAG

CAGCTGCTGGCTTCAACGACGTCGTCAAAATGCTCATTGCTCGGGGTACT

AATGTAGATGTCCGTACACGAGACAACTACACCGCTCTCCACGTAGCGGT

TCAATCTGGCAAGGCTTCGGTTGTAGAGACCCTGCTGGGAAGTGGTGCAG
ACATTCATGTGAAGGGCGGGGAACTAGGACAAACTGCACTGCACATTGCG
GCAAGCTTGAATGGAGCCGAGAGTCGGGATTGTGCGATGATGTTGCTGAA
AAGTGGAGGGCAGCCGGATGTTGCACAAATGGATGGGGAGACTTGTCTGC
ATATTGCTGCCAGGAGTGGGAATAAGGATATCATGAGGCTCCTGCTTGAC
GAGAACGCCGACTCGAAATAAGCTCAAAGATCGGAGAGACACCCCTCCA
GGTGGCCGCCAAGTCATGCAATTTTGAAGCAGCATCAATGATTTTGAAGC
ACCTTTCGGAAGTTCTGACCCAAGAACAGCTTAAGGAACATGTCAATCAT
AGAACCAATGACGGCTTCACAGCTCTTCACTACGCCGCTGAAATCGAGCA
GCGCCAGTTACACTTTCCAGGAGAAGATGCCAAGCTAGTAAATCTTCTGA
TCGACTACGGTGGAATGGTAGAAATGCCATCACTCAATGCAAATGAGACG
GCGATGCATATGGCGGCAAGATCCGGAAATCAAGCTGTACTCCTGGCGAT
GGTCAATAAGATCGGAGCCGGTGCGGTGCAAATCGTGCAGAACAAGCAGA
GCAAGAACGGATGGTCACCGCTGTTGGAAGCATGTGCCAGAGGGCATTCT
GGAGTGGCGAATATTTTGTTGAAGCACCACGCCCGTATTGATGTATTCGA
TGAAATGGGCCGTACTGCTCTGCACCTGGCAGCTTTCAATGGGCATCTCT
CCCTGGTTCACCTTCTTCTGCAGCACAAAGCATTCGTGAACAGTAAATCG
AAAACCGGAGAGGCACCGCTCCACTTAGCAGCTCAGCATGGTCATGTGAA
GGTGGTGAATGTCCTGGTGCAGGATCATGGTGCAGCGCTGGAGGCAATTA
CGCTGGATAATCAGACAGCCCTCCACTTTGCCGCAAAATTCGGTCAGCTA
GCTGTGAGTCAAACCCTTCTGGCTCTCGGAGCAAACCCCAATGCACGTGA
CGACAAGGGTCAAACCCCTCTCCATCTGGCAGCTGAGAATGACTTCCCCG
ACGTTGTGAAGCTCTTCCTGAAAATGAGAAATAACAACCGGAGTGTGTTG
ACCGCAATTGATCATAATGGATTCACCTGCGCACATATTGCTGCGATGAA
GGGTTCCCTAGCCGTGGTCCGTGAGCTTATGATGATCGACAAGCCTATGG
TAATCCAGGCAAAGACCAAAACACTGGAAGCCACTACACTTCATATGGCA
GCTGCGGGAGGTCACGCGAACATTGTGAAGATTCTGCTGGAGAATGGAGC
AAACGCGGAAGATGAGAATTCGCACGGAATGACTGCTCTCCACCTTGGCG
CCAAAAACGGATTCATATCGATTTTGGAGGCATTCGATAAGATCCTATGG
AAACGGTGTTCGAGAAAGACCGGTCTCAACGCTCTCCACATCGCTGCGTT
CTACGGAAATTCGGATTTCGTCAATGAAATGCTCAAGCACGTACAAGCAA
CAGTCCGTTCCGAGCCGCCCATCTACAATCACCATGTCAATAAGGAATTC
TCAACTGAATACGGCTTCACACCTCTCCATTTAGCCGCTCAAAGTGGACA
CGACAGTCTTGTGCGGATGCTTCTGAATCAGGGAGTGCAAGTTGACGCGA
CCAGTACTACAATGAACGTGATCCCCCTCCATCTGGCTGCCCAGCAAGGC
CACATCGCAGTGGTAGGAATGCTCCTGTCCAGATCTACTCAGCAGCAGCA
CGCCAAGGATTGGAGAGGCAGGACCCCGCTCCACCTAGCCGCTCAGAATG
GCCACTACGAGATGGTCTCACTTCTCATTGCTCAGGGATCTAACATCAAT
GTCATGGATCAGAATGGCTGGACTGGTCTTCACTTTGCCACTCGTGCCGG
GCACCTGAGTGTCGTCAAGCTGTTCATCGATAGTTCAGCGGATCCATTGG
CGGAGACCAAGGAGGGCAAAGTTCCATTGTGCTTTGCTGCAGCTCATAAT
CATATAGAATGTCTTCGATTCCTCCTGAAACAGAAGCATGACACACATCA
ATTGATGGAAGATCGGAAGTTCATATTCGACTTGATGGTTTGTGGTAAAA
CCAATGACAATGAGCCTCTACAAGAGTTTATTCTTCAATCACCTGCTCCA
ATTGAGACGGCAGTCAAGTTGTCCGCGTTGTACAGAGATATGTCGGAGAA
GGAGAAGGAGAGGGCGAAGGATCTGTTGAATGTGGCAGTGTTCAGTGAGA
ATATGGCTGTGGAGTTGTTAGGGATCACCGCCACCGAATACAATGCCGCT
CTTCTCCTGAAGGCTAAGGACAATCGAGGCCGGCCCCTACTAGATGTTCT
CATTGAAAATGAGCAGAAAGAAGTAGTCTCCTACGCGTCTGTCCAACGCT
ACCTGACAGAAGTATGGACTGCCCGTGTCGACTGGTCATTCGGAAAGTTT
GTCGCATTCTCCCTCTTCGTGCTAATATGCCCCCGGCATGGTTCTACTT
CTCACTTCCACTGGATAGTCGGATCGGAAGAGCTCCGATTATTAAATTTG
TGTGCCATATCGTGTCTCATGTCTATTTTACGATACTGCTGACAATTGTG
GTGTTGAATATTACACATAAGATGTACGAAGTAACTTCGGTGGTTCCAAA
CCCTGTGGAATGGCTCCTGTTGCTCTGGCTCTCTGGAAATCTGGTCTCCG
AACTCTCCACTGTCGGTGGAGGATCTGGCCTAGGAATCGTAAAGGTCCTA
ATCCTAGTCCTTTCCGCGATGGCGATAGCCGTCCATGTCCTAGCCTTCCT
GCTCCCGGCAGTATTCCTAACCCACCTGGATAACGATGAAAAGCTACATT
TCGCCCGGACAATGCTTTATTTGAAAAATCAACTTTTCGCCTTTGCCCTG
CTATTTGCTTTTGTAGAGTACCTGGATTTCCTGACAGTGCATCATTTGTT
CGGTCCCTGGGCGATCATTATTCGAGATCTAATGTATGATTTGGCCCGTT
TCCTTGTGATCCTGATGTTGTTCGTGGCGGGCTTCACACTCCACGTGACG
AGTATCTTCCAGCCTGCCTACCAGCCTGTCGACGAGGACAGCGCCGAGCT
GATGCGTCTGGCCTCCCCGTCTCAAACCCTCGAAATGCTCTTCTTCTCGC
TCTTCGGACTCGTCGAGCCCGATTCAATGCCCCCGCTCCATCTAGTTCCA
GATTTTGCAAAAATCATCTTAAAACTTCTATTCGGAATCTACATGATGGT
CACCTTGATTGTGCTGATCAACTTGCTGATTGCTATGATGTCTGACACCT
ACCAACGAATTCAGGCACAGTCGGATAAGGAATGGAAGTTCGGAAGAGCT
ATTCTGATCAGACAGATGAATAAGAAAAGCGCCACGCCGTCGCCGATAAA
TATGTTAACAAAGTTGATAATTGTGCTGAGGGTAGCCTGGCGGAATCGGT
TGAGATGCATGACCCGAAAAGCCCAAGACGATCTTCGCTTCGAGGAGAAC
ATCGACGCGTTCTCCATGGGTGGCGGCCAGCAGGGAAGGCAAAGTCCGAC
CAATGAAGGAAGAGAAGGCCAGCAAGAGCTTGGTAACTCGGCTGACTGGA
ACATCGAGACAGTCATCGACTGGAGGAAGATTGTTTCAATGTACTATCAG
GCGAATGGGAAGCTTACAGACGGGCGAACCAAAGAGGATGTGGATTTGGC
AATGGCAGTACCTACTAGTTTTTAG

For expression in a human cell, the following codon optimized sequence is used:

GTTTAAACGGCGCGCCGGTACCATGAATCCTCACACTTCTCAGCCAGGGC
CAAGCCATGTCTCCATTGTCAACGTGCCAGAGCGGGGGGGACCAACCTCC
TCAACCTCCACCACACACGAGACCGAACACACAGCCCATCGCACAGAGAG

-continued

CGGCCGATTCATCCGGAGAAGGCGCCAGTCCAGAGAAGTGACTACCACAA

CTACCAGGCCCTACGATCCTGCACCACCTACCCAGACAAGAACTAGCTCC

GGCTCCACCGTGAATGGGTGGGGCGAGAACAGGCCCAAGTCTGCCGACGA

GGAGATCAAGCGACGGAGAAGGAGTGGCGGGGGAATCCTGTCAAGAGGGC

TGAGGGAGATGAACAAGATGGTGGAGGAACTGGAACAGGCCTCTGAGGAA

CCCAGTACACGCAAGGGCATTCTGGGGACTGCTCTGAAAGACATGGAGGG

CACAACTTACCAGAAGATCTATCGGAAAAGAGAGGAAACCCCTAAAAGGT

CTCGCAGTTTCGACGATCAGGAGATGAGCAACAGAGTGGGGATGATCGAA

CATCTGCTGAGGGACAAGGACCCCCTGGAGCTCCAGCAGCTGGGACTGAC

AGACCTGCTGACCACAGATACTATTCCAACCGACCGACCACCACTGCGCC

GATCTAGTACTCACCTCCAGATCGGCAAGAACAGCCGGATCATTTTCGTG

CCAAAACAGCCCAGCCGCGATTCCGTCACTCCTCAGACCGACTGCTGGG

CAAGCCTCTGTTTCGGGAGTCTCTGACCAGTCACGCCTCAAGCCATGAGG

AAATGTCCTCTGAAGATCTGGCTATGGCCGACCCCCAGACCAAGATCCTG

TACTTCGCCAAACGCGACGAGTGGGCTAATGTGGAGTCCGAAATTGAGAC

AATCAAGCGGTCAGACTTCAGCATGGCCGACAACCACGGATTCACTGCTT

TTCTGCTGGCAGTGAAGGCCGGCAAAGACCAGATTGTCGATAAGATGATC

CGAAAAGGAGCACGGGTGGATTATTCTACCAAGGACGGCAGAAACGCCAC

ACATATTGCCGCTATGTACAGTGGCGTGGAGACACTGGAACTGATCCTGA

AGAGGTATTCAGAGCTGCTGCGCAAAGGCGCCGGGCCTAAGAAACAGCTG

GCAATCCACGTGGCCTGCGAAAGGAAGTCCAAGAAAGCCTTCCCAATTGT

GAAAAGAATCCTGGAGGACACCGATCAGAGGATGGCTGAAGACGGAGATG

GCTCTCTGCCCATTCACCTGGCATTCAAATTTGGGAATGTGAACATCGTC

GAGCTGCTGCTGTCCGGACCTTCTGATGAACAGACTAGAAAGGCCGACGG

GAATGGAGATACCCTGCTGCATCTGGCAGCACGCTCCGGAAACATTGAGG

CTGTGCGAACCGCAATCGCCGCCGGATGCGACAATGCCAACGTGCAGAAC

CGCGTCGGGCGAACACCACTGCACGAGGTGGCTGAAGTCGGAGATCAGAA

TATGCTGAAGATTATGTTCAAACTGCGCGCAGACGCCAACATCCATGACA

AGGAGGATAAAACACCAGTGCACGTCGCCGCTGAGCGAGGCGATACTTCA

ATGGTGGAAAGCCTGATTGACAAGTTTGGCGGGTCCATCCGAGCCCGGAC

AAGAGATGGCTCTACTCTGCTGCATATCGCAGCCTGTTCCGGGCACACCT

CTACAGCTCTGGCATTCCTGAAGAGAGGCGTGCCTCTGTTTATGCCAAAT

AAGAAAGGAGCCCTGGGACTGCATAGCGCCGCCGCCGCCGGCTTCAACGA

CGTGGTCAAGATGCTGATCGCCAGGGGAACAAATGTGGATGTCAGGACCC

GCGACAACTACACAGCCCTGCACGTGGCTGTCCAGAGTGGCAAGGCCAGC

GTGGTCGAGACTCTGCTGGGCAGCGGAGCAGATATTCATGTGAAGGGAGG

AGAACTGGGACAGACCGCCCTGCACATCGCAGCCAGCCTGAACGGGCAG

AGTCCAGGGACTGCGCCATGATGCTGCTGAAAAGCGGGGGACAGCCTGAT

GTGGCCCAGATGGACGGAGAAACCTGTCTGCACATTGCTGCACGGTCTGG

CAATAAGGATATCATGAGACTGCTGCTGGACGAGAACGCCGATAGTAAGA

-continued

TTAGTTCAAAAATCGGCGAAACTCCACTCCAGGTGGCCGCTAAGTCTTGC

AACTTCGAGGCAGCCAGTATGATCCTGAAACACCTGTCAGAAGTGCTGAC

CCAGGAGCAGCTGAAGGAACACGTCAATCATAGAACTAACGACGGCTTCA

CCGCCCTGCATTACGCCGCCGAGATTGAGCAGAGGCAGCTGCACTTTCCA

GGGGAGGATGCCAAGCTGGTGAATCTGCTGATCGACTATGGCGGGATGGT

CGAGATGCCCTCACTGAATGCAAACGAAACCGCCATGCACATGGCCGCTA

GAAGCGGAAATCAGGCTGTGCTGCTGGCAATGGTCAACAAGATTGGAGCC

GGCGCTGTGCAGATCGTCCAGAATAAGCAGTCAAAAAACGGCTGGAGCCC

ACTGCTGGAGGCATGTGCCAGGGGGCATAGCGGAGTGGCTAACATTCTGC

TGAAGCACCATGCACGCATCGACGTGTTCGATGAAATGGGGCGAACAGCC

CTGCACCTGGCAGCCTTTAATGGACACCTGAGCCTGGTGCATCTGCTGCT

CCAGCACAAAGCCTTCGTCAACTCAAAGAGCAAAACCGGAGAGGCTCCAC

TGCACCTGGCTGCACAGCACGGGCATGTGAAGGTGGTCAATGTGCTGGTC

CAGGATCATGGGGCCGCTCTGGAGGCCATCACACTGGACAACCAGACTGC

TCTGCACTTCGCAGCCAAATTTGGACAGCTGGCCGTGAGCCAGACACTGC

TGGCTCTGGGGGCAAATCCTAACGCTAGAGACGATAAGGGACAGACTCCA

CTGCACCTGGCCGCCGAGAACGACTTCCCCGATGTGGTCAAGCTGTTTCT

GAAAATGAGAAACAATAACAGGAGCGTGCTGACAGCAATTGATCATAATG

GCTTCACCTGCGCCCACATCGCCGCTATGAAAGGCAGCCTGGCCGTGGTC

AGGGAGCTGATGATGATTGACAAGCCTATGGTCATCCAGGCAAAGACTAA

AACCCTGGAAGCCACTACCCTGCACATGGCAGCCGCTGGAGGACACGCCA

ACATTGTGAAGATCCTGCTGGAGAATGGCGCTAACGCAGAAGATGAGAAC

AGCCACGGCATGACCGCACTGCACCTGGGAGCCAAAAACGGATTC

ATTTCCATCCTGGAGGCCTTTGACAAGATTCTGTGGAAGCGGTGCAGCCG

GAAGACAGGGCTGAATGCTCTGCATATCGCAGCCTTCTACGGAAATAGCG

ACTTTGTGAACGAGATGCTGAAACACGTGCAGGCCACTGTCCGCAGTGAA

CCCCCTATCTACAATCACCATGTGAACAAGGAGTTCTCAACCGAATATGG

CTTTACACCTCTGCATCTGGCTGCACAGAGCGGGCACGATTCCCTGGTGC

GGATGCTGCTGAATCAGGGCGTGCAGGTCGACGCCACCAGCACAACTATG

AACGTGATTCCACTGCATCTGGCAGCTCAGCAGGGACACATCGCAGTGGT

CGGAATGCTGCTGTCCCGCTCTACCCAGCAGCAGCACGCTAAGGATTGGC

GAGGACGGACACCCCTGCATCTGGCAGCCCAGAACGGCCACTATGAGATG

GTGAGCCTGCTGATTGCCCAGGGCTCCAATATCAACGTGATGGACCAGAA

TGGCTGGACTGGACTGCATTTCGCAACCCGGGCTGGACACCTGAGCGTGG

TCAAGCTGTTTATCGACAGCTCCGCCGATCCTCTGGCTGAGACCAAGGAA

GGCAAAGTGCCACTGTGCTTCGCTGCCGCCCACAACCATATTGAGTGTCT

GAGATTTCTGCTGAAGCAGAAACACGATACACATCAGCTGATGGAAGATA

GGAAGTTCATCTTTGACCTGATGGTGTGCGGCAAAACTAATGACAACGAG

CCTCTCCAGGAGTTCATCCTCCAGTCCCCCGCTCCTATCGAGACCGCAGT

GAAACTGTCTGCCCTGTACAGAGATATGAGTGAAAAGGAGAAAGAAGGG

CTAAGGACCTGCTGAATGTGGCAGTCTTTTCTGAGAACATGGCCGTGGAA

-continued

```
CTGCTGGGAATTACAGCAACTGAGTATAATGCTGCACTGCTGCTGAAGGC
CAAAGATAACAGAGGCAGGCCACTGCTGGACGTGCTGATCGAGAACGAAC
AGAAAGAGGTGGTCAGTTACGCCTCAGTGCAGAGATACCTGACAGAAGTG
TGGACTGCTCGGGTCGATTGGTCATTCGGGAAGTTTGTGGCATTCAGCCT
GTTTGTCCTGATTTGCCCACCCGCCTGGTTCTACTTTTCCCTGCCACTGG
ACTCTAGGATTGGACGCGCCCCATCATCAAGTTCGTGTGCCACATCGTG
TCCCATGTCTACTTTACCATTCTGCTGACAATCGTGGTCCTGAATATCAC
TCACAAGATGTATGAGGTGACCAGCGTGGTCCCAAATCCCGTCGAATGGC
TGCTGCTGCTGTGGCTGTCCGGCAACCTGGTGAGCGAGCTGTCCACCGTC
GGAGGAGGCAGCGGACTGGGAATTGTGAAGGTCCTGATCCTGGTGCTGAG
CGCAATGGCCATCGCAGTGCACGTCCTGGCTTTCCTGCTGCCCGCAGTGT
TTCTGACTCATCTGGACAATGATGAGAAGCTGCACTTCGCCCGCACCATG
CTGTACCTGAAAAACCAGCTGTTCGCCTTTGCTCTGCTGTTCGCTTTTGT
GGAATATCTGGACTTCCTGACAGTCCACCATCTGTTTGGGCCTTGGGCTA
TCATTATTAGGGACCTGATGTACGATCTGGCACGGTTCCTGGTCATCCTG
ATGCTGTTCGTCGCCGGCTTCACCCTGCATGTGACCTCTATCTTTCAGCC
CGCCTATCAGCCTGTCGACGAGGATAGTGCTGAACTGATGCGGCTGGCAA
GTCCCTCACAGACCCTGGAGATGCTGTTCTTTAGTCTGTTCGGCCTGGTG
GAACCCGATTCAATGCCTCCACTGCACCTGGTGCCTGACTTCGCCAAGAT
TATCCTGAAACTGCTGTTTGGGATCTACATGATGGTGACCCTGATTGTCC
TGATCAACCTGCTGATTGCTATGATGTCTGATACATATCAGCGCATCCAG
GCACAGAGTGACAAGGAGTGGAAATTTGGCCGGGCCATTCTGATCAGACA
GATGAATAAGAAATCTGCTACCCCTAGTCCAATTAACATGCTGACAAAAC
TGATTATCGTGCTGCGGGTCGCTTGGCGCAATCGACTGCGGTGTATGACC
CGAAAGGCCCAGGACGATCTGCGGTTCGAGGAAAACATCGACGCTTTTTC
AATGGGGGAGGACAGCAGGGACGACAGAGCCCTACCAATGAGGGACGAG
AAGGACAGCAGGAGCTGGGCAATTCCGCCGATTGGAACATTGAAACAGTG
ATCGACTGGAGAAAGATCGTCTCTATGTACTATCAGGCCAATGGCAAACT
GACTGACGGGCGAACCAAGGAGGATGTCGATCTGGCTATGGCTGTCCCTA
CTTCTTTCTGAATTCCGATAACTTGTTTATTGCAGCTTATAATGGTTACA
AATAAAGCAATAGCATCACAAATTTCACAAATAAAGCATTTTTTTCACTG
CATTCTAGTTGTGGTTTGTCCAAACTCATCAATGTATCTTATCATGTCTG
GCGGCCGC
```

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics, which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid, which encodes a polypeptide is implicit in each described sequence with respect to the expression product, but not with respect to actual probe sequences.

By "altered" is meant an increase or decrease. An increase is any positive change, e.g., by at least about 5%, 10%, or 20%; preferably by about 25%, 50%, 75%, or even by 100%, 200%, 300% or more. A decrease is a negative change, e.g., a decrease by about 5%, 10%, or 20%; preferably by about 25%, 50%, 75%; or even an increase by 100%, 200%, 300% or more.

The terms "comprises", "comprising", and are intended to have the broad meaning ascribed to them in U.S. Patent Law and can mean "includes", "including" and the like.

"Contacting" is used in accordance with its plain ordinary meaning and refers to the process of allowing at least two distinct species (e.g. chemical compounds including biomolecules, or cells) to become sufficiently proximal to react, interact, affect or physically touch. It should be appreciated, however, that the resulting reaction product can be produced directly from a reaction between the added reagents or from an intermediate from one or more of the added reagents, which can be produced in the reaction mixture. Contacting may include allowing two species to react, interact, or physically touch, wherein the two species may be a recombinant viral particle as described herein and a cell. In embodiments, the two species are an ultrasound contrast agent that is exposed to ultrasound and a cell.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

By "mammal" is meant any warm-blooded animal including but not limited to a human, cow, horse, pig, sheep, goat, bird, mouse, rat, dog, cat, monkey, baboon, or the like. Preferably, the mammal is a human.

"Nucleic acid" refers to deoxyribonucleotides or ribonucleotides and polymers thereof in either single- or double-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

By "positioned for expression" is meant that a polynucleotide (e.g., a DNA molecule) is positioned adjacent to a DNA sequence, which directs transcription, and, for proteins, translation of the sequence (i.e., facilitates the production of, for example, a recombinant polypeptide of the invention, or an RNA molecule).

The term "plasmid" or "vector" refers to a nucleic acid molecule that encodes for genes and/or regulatory elements necessary for the expression of genes. Expression of a gene from a plasmid or vector can occur in cis or in trans. If a gene is expressed in cis, the gene and the regulatory elements are encoded by the same plasmid and vector. Expression in trans refers to the instance where the gene and the regulatory elements are encoded by separate plasmids or vectors.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" or "control" is meant a standard condition. For example, an untreated cell, tissue, or organ that is used as a reference.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "subject" as used herein refers to a vertebrate, preferably a mammal (e.g., dog, cat, rodent, horse, bovine, rabbit, goat, or human).

By "transformed cell" is meant a cell into which (or into an ancestor of which) has been introduced, by means of recombinant DNA techniques, a polynucleotide molecule encoding (as used herein) a polypeptide of the invention.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "transformed cell" is meant a cell into which (or into an ancestor of which) has been introduced, by means of recombinant DNA techniques, a polynucleotide molecule encoding (as used herein) a polypeptide of the invention.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein (e.g. Tat, Rev) relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

BRIEF DESCRIPTION OF THE DRAWINGS

FIG. 1A, FIG. 1B, FIG. 1C, FIG. 1D, FIG. 1E, and FIG. 1F: Amplifying ultrasound signals using microbubbles modifies animal behavior. FIG. 1A is a schematic of the computer-controlled imaging and ultrasound exposure system, FIG. 1B shows the agar plate with animals and FIG. 1C shows a stabilized microbubble. FIG. 1D provides images showing that animals exhibit reversal and omega bends upon ultrasound stimulus (10 ms, 2.25 MHz with peak negative pressure of 0.9 MPa) only in the presence of microbubbles. Quantification of animal responses to ultrasound stimuli (10 ms, 2.25 MHz) with varying peak negative pressures without as shown in FIG. 1E and with microbubbles as shown in FIG. 1F. n=30 for each of the conditions. Averages and s.e.m. are shown. ** indicates p<0.01 and * indicates p<0.05 by Fisher's exact t-test.

FIG. 2A shows behavioral responses to low intensity ultrasound require the pore-forming TRP-4 channel. n=30 for each condition. Transgenic animals expressing TRP-4 in ASH neurons as shown in FIG. 2B and in AWC neurons as shown in FIG. 2C execute more reversals upon low intensity ultrasound stimulation (2.25 MHz, 10 ms). n>30 for each genotype and condition. Averages and s.e.m are shown in all data panels. ** indicates p<0.05, while * indicates p<0.01 by Fisher's exact t-test. FIG. 2D provides a schematic identifying chemosensory neurons ASH and AWC in C. elegans. False-colored images showing changes in GCaMP fluorescence in AWC neurons upon ultrasound stimulation. Warmer colors indicate increased calcium and neural activity. FIG. 2E provides average AWC calcium responses upon ultrasound stimulation (WT n=20, AWC::TRP-4 n=23). FIG. 2F provides average responses binned by distinct times for Control and AWC::TRP-4 animals. Averages and s.e.m are shown. * indicates p<0.05 by t-test.

FIG. 3A provides a schematic showing PVD and FLP neurons in C. elegans. FIG. 3B shows two independent transgenics expressing TRP-4 in PVD neurons show reduced reversals when stimulated with a 2.25 MHz 0.47 MPa peak negative pressure ultrasound wave for 10 ms. n>46 for each genotype. Averages and s.e.m. are shown. ** indicates p<0.05, while * indicates p<0.01 by Fisher's exact t-test. FIG. 3C provides false-colored images showing changes in GCaMP fluorescence in PVD neurons upon ultrasound stimulation. Warmer colors indicate increased calcium and neural activity. FIG. 3D shows average PVD calcium responses (n=16) along with distance moved by the animal shown as a function of time. Peak PVD response occurs when the animal has stopped moving. FIG. 3E provides a schematic showing the neural circuit that responds to ultrasound stimuli and microbubbles. ASH and AWC neurons promote reversals, while PVD neurons inhibit them. FIG. 3F shows AIY calcium responses to ultrasound stimuli. A representative trace showing the ratio of change in fluorescence to the baseline is shown. Ultrasound stimulus was given at t=5 s and neurons that responded within a 5.5 second window after the stimulus were counted as responders. Bar graphs show % responders with and without ultrasound stimuli for AIY::GCaMP and AIY::GCaMP;AIY::trp-4. Numbers on the bars indicate the number of animals analyzed in each condition. * indicates p<0.05 by fisher exact t-test.

FIG. 4A shows microbubbles that were labeled such that DiI was stably incorporated into the lipid monolayer. FIG. 4B provides a whole animal view showing brightfield fluorescence before and after ultrasound stimulus and finally, the difference in red. FIG. 4C shows a magnified view of the animal's head showing the same frames as above. The white arrow points to a large microbubble that is destroyed upon ultrasound stimulation. The red images highlight those microbubbles that have been activated and destroyed by ultrasound stimulus.

FIG. 8A shows microbubbles that are uniformly distributed on an agar surface and appear white. FIG. 8B shows that ultrasound stimulus (10 pulses of 10 ms, 2.25 MHz with peak negative pressure of 0.9 MHz) activates the microbubbles specifically in an area of 1 mm diameter (white arrow). Microbubbles outside this focal zone appear undisturbed. FIG. 8C shows that the microbubble (i) expands and (ii) contracts in size with the rarefaction (low-pressure) and compression (high-pressure) portions of the ultrasound pressure wave. This oscillation behavior occurs at the frequency of the driving ultrasound resulting in a variety of behaviors including (iii) microbubble collapse, (iv) fluid microstreaming and (v) merging of microbubbles. These microbubble behaviors create mechanical distortions that can propagate through the agar and the body of the animal.

FIG. 9 panels show an animal reversing and generating a high-angled omega bend upon ultrasound stimulus. Reversals with greater than two head bends were scored as large, while those with fewer than two head bends were counted as small. Reversals and omega bends are shown with a red line overlaid on the animal tracks on the agar surface.

FIG. 10A provides a bar and whisker plot showing the distribution of microbubbles fractionated based on their size. A one-way ANOVA test shows significance in the distribution ( indicates p<0.001). Mixed size population was used for all experiments shown to maintain consistency. FIG. 10B provides images showing animals incubated with small (top) and large (bottom) population of microbubbles. FIG. 10C shows behavioral responses of wildtype animals incubated with small and large microbubbles upon ultrasound stimulation of 10 ms pulse with 2.25 MHz with peak negative pressure of 0.9 MPa. Averages and 95% confidence limits are shown.  indicates p<0.001 fisher's exact t-test. FIG. 10D provides a graph showing the effect of external humidity levels on animal reversal behavior. It was observed that at different times of the year the animals had different reversal behavior in response to the same 0.47 MPa ultrasound exposure. Under low humidity levels the animals would undergo more large reversals than under high humidity conditions. Applicants accounted for this variable behavior by running a wild-type control for each of the genetically modified strains that was tested. These controls were run on the same day and under the same conditions as the tested strain. Error bars show standard error of the proportion.

FIGS. 11E-11H show the ratio of change in fluorescence to baseline fluorescence in the AIY neurite expressing trp-4 in AIY interneurons specifically without as shown in FIGS. 11E and 11F and with ultrasound as shown in FIGS. 11G and 11H. Neurons that responded in the same 5.5 second window around t=5 seconds are shown in FIGS. 11E and 11G and those that did not are shown in FIGS. 11F and 11H. Each trace represents data from a single neuron recorded once.

FIG. 15A-15G: AWC calcium responses to ultrasound stimulus. Ratio of change in fluorescence to baseline fluorescence in AWC neurons expressing the calcium sensor, GCaMP2.2b (n=20) as shown in FIG. 15A and trp-4 specifically in AWC neurons (n=23) as shown in FIG. 15B. Of these 23 animals tested, 3 reached the baseline as shown in FIG. 13C. AWC calcium responses without ultrasound stimulus in wild-type (n=10) are shown in FIG. 15D and AWC::trp-4 transgenics (n=6) are shown in FIG. 15E. Each color represents the response of an individual neuron to ultrasound stimulus presented at t=5 seconds. FIG. 15F provides average AWC calcium responses without ultrasound stimulus in wild-type and AWC::trp-4 transgenics. FIG. 15G provides average AWC calcium data binned similarly to the data shown in FIG. 5F. Microbubbles are included in all AWC calcium recordings.

FIG. 16A provides an average of 6 different FLP GCaMP responses to the ultrasound stimulus presented at t=5 s. No response was observed. FIG. 16B provides the 6 individual FLP GCaMP traces shown in FIG. 16A. Microbubbles are present in all FLP recordings.

FIG. 17A provides an expanded view of average PVD trace in response to ultrasound and microbubbles shown in FIG. 6D. The animal was stimulated with a single ultrasound pulse at t=5 s. There was an immediate decrease in fluorescence, which was then followed by a rapid increase. PVD activity is strongly correlated with movement (n=89) as shown in FIG. 17B, in the backward direction (Backward n=25, forward n=16) as shown in FIG. 17C and in animals that stopped (stop or slow down n=22, not stopping or slowing down n=19) as shown in FIG. 17D. Proportions and standard error of the proportion are shown with *** indicating p<0.001 by Fisher' exact t-test.

DETAILED DESCRIPTION OF THE INVENTION

Figure 1A:
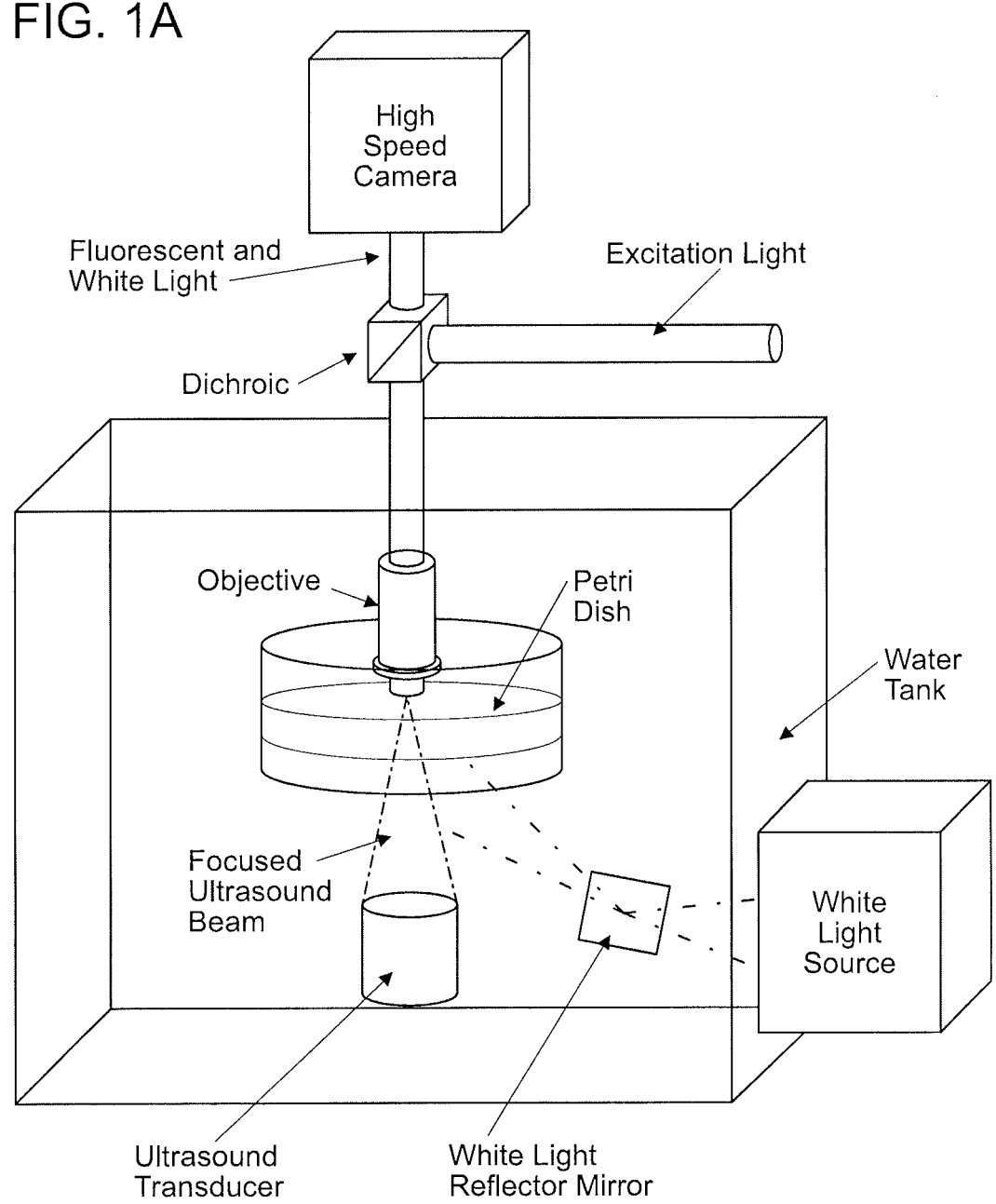

The invention provides compositions featuring TRP-4 polypeptides and polynucleotides, methods for expressing such polypeptides and polynucleotides in a cell type of interest, and methods for inducing the activation of the TRP-4 polypeptide in neurons and other cell types using ultrasound.

The invention is based, at least in part, on the discovery that misexpression of TRP-4, a pore-forming subunit of a mechanotransduction channel, sensitizes cells to an ultrasound stimulus resulting in calcium influx and motor outputs. Accordingly, this approach can be used to alter cellular functions in vivo.

Accordingly, the invention provides polynucleotides encoding a TRP4 polypeptide, expression vectors comprising such polynucleotides, cells expressing a recombinant TRP4 polypeptide, and methods for stimulating such cells with ultrasound.

Ultrasound

Ultrasound is well suited for stimulating neuron populations as it focuses easily through intact thin bone and deep tissue (K. Hynynen and F. A. Jolesz, *Ultrasound Med Biol* 24 (2), 275 (1998)) to volumes of just a few cubic millimeters (G. T. Clement and K. Hynynen, *Phys Med Biol* 47 (8), 1219 (2002)). The non-invasive nature of ultrasound stimulation is particularly significant for manipulating vertebrate neurons including those in humans, as it eliminates the need for surgery to insert light fibers (required for some current optogenetic methods). Also, the small focal volume of the ultrasound wave compares well with light that is scattered by multiple layers of brain tissue (S. I. Al-Juboori, A. Dondzillo, E. A. Stubblefield et al., *PLoS ONE* 8 (7), e67626 (2013)). Moreover, ultrasound has been previously used to manipulate deep nerve structures in human hands and reduce chronic pain (W. D. O'Brien, Jr., *Prog Biophys Mol Biol* 93 (1-3), 212 (2007); L. R. Gavrilov, G. V. Gersuni, 0. B. Ilyinsky et al., *Prog Brain Res* 43, 279 (1976)). The invention provides for novel non-invasive compositions for the expression of TRP4 in cells, and methods to stimulate cells expressing TRP4 using low-intensity ultrasound stimulation.

Cellular Compositions Comprising Recombinant TRP-4

The invention provides cells comprising a recombinant nucleic acid molecule encoding a TRP-4 polypeptide. In one embodiment, the invention provides a cardiac muscle cell comprising a TRP-4 polynucleotide under the control of a promoter suitable for expression in a cardiac cell (e.g., NCX1 promoter). In another embodiment, the invention provides a muscle cell comprising a TRP-4 polynucleotide under the control of a promoter suitable for expression in a muscle cell (e.g., myoD promoter). In another embodiment, the invention provides an insulin secreting cell (e.g., beta islet cell) comprising a TRP-4 polynucleotide under the control of a promoter suitable for expression in an insulin-secreting cell (e.g., Pdx1 promoter). In another embodiment, the invention provides an adipocyte comprising a TRP-4 polynucleotide under the control of a promoter suitable for expression in an adipocyte (e.g., iaP2). In another embodiment, the invention provides a neuron comprising a TRP-4 polynucleotide under the control of a promoter suitable for expression in a neuron (e.g., nestin, Tuj1 promoter), in a motor neuron (e.g., H2b promoter), in an interneuron (e.g., Islet 1 promoter), in a sensory neuron (e.g., OMP promoter, T1R, T2R promoter, rhodopsin promoter, Trp channel promoter). Such cells may be cells in vitro or in vivo. In particular embodiments, the cells express a mechanotransduction polypeptide that is a transient receptor potential channel-N (TRPN) polypeptide that is sensitive to ultrasound. In particular embodiments, the mechanotransduction polypeptide is TRP-4 or a functional portion or homolog thereof. In embodiments, the mechanotransduction polypeptide comprises or consists of the amino acid sequence of SEQ ID NO:1.

Expression of Recombinant TRP-4

In one approach, a cell of interest (e.g., neuron, such as a motor neuron, sensory neuron, neuron of the central nervous system, or neuronal cell lines) is engineered to express a TRP-4 polynucleotide whose expression renders the cell responsive to ultrasound stimulation. Ultrasound stimulation of such cells induces cation influx.

TRP-4 may be constitutively expressed or its expression may be regulated by an inducible promoter or other control mechanism where conditions necessitate highly controlled regulation or timing of the expression of a TRP-4 protein. For example, heterologous DNA encoding a TRP4 gene to be expressed is inserted in one or more pre-selected DNA sequences. This can be accomplished by homologous recombination or by viral integration into the host cell genome. The desired gene sequence can also be incorporated into a cell, particularly into its nucleus, using a plasmid expression vector and a nuclear localization sequence. Methods for directing polynucleotides to the nucleus have been described in the art. The genetic material can be introduced using promoters that will allow for the gene of interest to be positively or negatively induced using certain chemicals/drugs, to be eliminated following administration of a given drug/chemical, or can be tagged to allow induction by chemicals, or expression in specific cell compartments.

Calcium phosphate transfection can be used to introduce plasmid DNA containing a target gene or polynucleotide into cells and is a standard method of DNA transfer to those of skill in the art. DEAE-dextran transfection, which is also known to those of skill in the art, may be preferred over calcium phosphate transfection where transient transfection is desired, as it is often more efficient. Since the cells of the present invention are isolated cells, microinjection can be particularly effective for transferring genetic material into the cells. This method is advantageous because it provides delivery of the desired genetic material directly to the nucleus, avoiding both cytoplasmic and lysosomal degradation of the injected polynucleotide. Cells can also be genetically modified using electroporation.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPQ) can be added. Commercially available reagents for liposomal transfer include Lipofectin (Life Technologies). Lipofectin, for example, is a mixture of the cationic lipid N-[1-(2, 3-dioleyloxy)propyl]-N—N—N-trimethyl ammonia chloride and DOPE. Liposomes can carry larger pieces of DNA, can generally protect the polynucleotide from degradation, and can be targeted to specific cells or tissues. Cationic lipid-mediated gene transfer efficiency can be enhanced by incorporating purified viral or cellular envelope components, such as the purified G glycoprotein of the vesicular stomatitis virus envelope (VSV-G). Gene transfer techniques which have been shown effective for delivery of DNA into primary and established mammalian cell lines using lipopolyamine-coated DNA can be used to introduce target DNA into the de-differentiated cells or reprogrammed cells described herein.

Naked plasmid DNA can be injected directly into a tissue comprising cells of interest. Microprojectile gene transfer can also be used to transfer genes into cells either in vitro or in vivo. The basic procedure for microprojectile gene transfer was described by J. Wolff in Gene Therapeutics (1994), page 195. Similarly, microparticle injection techniques have been described previously, and methods are known to those of skill in the art. Signal peptides can be also attached to plasmid DNA to direct the DNA to the nucleus for more efficient expression.

Viral vectors are used to genetically alter cells of the present invention and their progeny. Viral vectors are used, as are the physical methods previously described, to deliver one or more polynucleotide sequences encoding TRP4, for example, into the cells. Viral vectors and methods for using them to deliver DNA to cells are well known to those of skill in the art. Examples of viral vectors that can be used to genetically alter the cells of the present invention include, but are not limited to, adenoviral vectors, adeno-associated viral vectors, retroviral vectors (including lentiviral vectors), alphaviral vectors (e.g., Sindbis vectors), and herpes virus vectors.

Targeted Cell Types

TRP-4 can be expressed in virtually any eukaryotic or prokaryotic cell of interest. In one embodiment, the cell is a bacterial cell or other pathogenic cell type. In another embodiment, the cell is a mammalian cell, such as an adipocyte, muscle cell, cardiac muscle cell, insulin secreting cell (e.g., beta islet cell), and neuron (e.g., motor neuron, sensory neuron, neuron of the central nervous system, and neuronal cell line).

Methods of Stimulating a Neural Cell

The methods provided herein are, inter alia, useful for the stimulation (activation) of cells. In particular, ultrasound stimulation induces cation influx, thereby altering cell activity. Expression of TRP-4 in a pathogen cell (bacteria) and subsequent ultrasound stimulation induces cation influx and bacterial cell killing. Ultrasound stimulation of a muscle cell expressing TRP-4 results in muscle contraction. This can be used to enhance muscle contraction or functionality in subjects in need thereof, including subjects suffering from muscle weakness, paralysis, or muscle wasting. Altering the intensity of the ultrasound modulates the extent of muscle activity.

The term "neural cell" as provided herein refers to a cell of the brain or nervous system. Non-limiting examples of neural cells include neurons, glia cells, astrocytes, oligodendrocytes and microglia cells. Where a neural cell is stimulated, a function or activity (e.g., excitability) of the neural cell is modulated by modulating, for example, the expression or activity of a given gene or protein (e.g., TRP-4) within said neural cell. The change in expression or activity may be 10%, 20%, 30%, 40%, 50%, 60%, 70%, 80%, 90% or more in comparison to a control (e.g., unstimulated cell). In certain instances, expression or activity is 1.5-fold, 2-fold, 3-fold, 4-fold, 5-fold, 10-fold or higher than the expression or activity in the absence of stimulation. In certain instances, expression or activity is 1.5-fold, 2-fold, 3-fold, 4-fold, 5-fold, 10-fold or lower than the expression or activity in the absence of stimulation. The neural cell may be stimulated by applying an ultrasonic wave to the neural cell.

The term "applying" as provided herein is used in accordance with its plain ordinary meaning and includes the meaning of the terms contacting, introducing and exposing. An "ultrasonic wave" as provided herein is an oscillating sound pressure wave having a frequency greater than the upper limit of the human hearing range. Ultrasound (ultrasonic wave) is thus not separated from 'normal' (audible) sound by differences in physical properties, only by the fact that humans cannot hear it. Although this limit varies from person to person, it is approximately 20 kilohertz (20,000 hertz) in healthy, young adults. Ultrasound (ultrasonic wave) devices operate with frequencies from 20 kHz up to several gigahertz. The methods provided herein use the energy of an ultrasonic wave to stimulate a neural cell expressing an exogenous mechanotransduction protein. A mechanotransduction protein as provided herein refers to a cellular protein capable of converting a mechanical stimulus (e.g., sound, pressure, movement) into chemical activity. Cellular responses to mechanotransduction are variable and give rise to a variety of changes and sensations. In embodiments, the mechanotransduction protein is a mechanically gated ion channel, which makes it possible for sound, pressure, or movement to cause a change in the excitability of a cell (e.g., a sensory neuron). The stimulation of a mechanotransduction protein may cause mechanically sensitive ion channels to open and produce a transduction current that changes the membrane potential of a cell.

In one aspect, a method of stimulating a cell is provided. The method includes (i) transfecting a cell with a recombinant vector including a nucleic acid sequence encoding an exogenous mechanotransduction polypeptide, thereby forming a transfected cell. (ii) To the transfected cell an ultrasonic wave is applied, thereby stimulating a cell. In embodiments, the mechanotransduction polypeptide is a transient receptor potential channel-N (TRPN) polypeptide or homolog thereof. In embodiments, the mechanotransduction polypeptide is TRP-4 or a functional portion or homolog thereof. In embodiments, the mechanotransduction polypeptide includes the amino acid sequence of TRP4 SEQ ID NO:1. In embodiments, the mechanotransduction polypeptide is the sequence of SEQ ID NO:1. In embodiments, the ultrasonic wave has a frequency of about 0.8 MHz to about 4 MHz. In embodiments, the ultrasonic wave has a frequency of about 1 MHz to about 3 MHz. In embodiments, the ultrasonic wave has a focal zone of about 1 cubic millimeter to about 1 cubic centimeter.

In embodiments, the method further includes before the applying of step (ii) contacting the transfected neural cell with an ultrasound contrast agent. In embodiments, the ultrasound contrast agent is a microbubble. In embodiments, the microbubble has a diameter of about 1 µm to about 6 µm. In embodiments, the neural cell forms part of an organism. In embodiments, the organism is a bacterial cell or mammalian cell (e.g., human, murine, bovine, feline, canine).

Methods of Treatment

In another aspect, a method of treating a neurological disease in a subject in need thereof is provided. The method includes (i) administering to a subject a therapeutically effective amount of a recombinant nucleic acid encoding an exogenous mechanotransduction polypeptide (e.g., TRP-4). In step (ii) an ultrasonic wave is applied to the subject, resulting in a change in TRP-4 conductance, i.e., cation influx. In one embodiment, the methods treat a cardiac disease by enhancing cardiac muscle activity or neurological disease by altering neural activity in the subject. In embodiments, the neurological disease is Parkinson Disease, depression, obsessive-compulsive disorder, chronic pain, epilepsy or cervical spinal cord injury. In embodiments, the neurological disease is retinal degeneration or atrial fibrillation. In embodiments, the mechanotransduction polypeptide is a transient receptor potential channel-N (TRPN) polypeptide or homolog thereof. In embodiments, the mechanotransduction polypeptide is TRP-4 or a functional portion or homolog thereof. In embodiments, the method further includes before the applying of step (ii) administering to the subject an ultrasound contrast agent. In embodiments, the ultrasound contrast agent is a microbubble. In embodiments, the microbubble has a diameter of about 1 µm to about 6 µm, and is injected into the body (e.g., the brain) where it enhances ultrasound stimulation.

EXAMPLES

Reliable activation of identified neurons, particularly those in deeper brain regions remains a major challenge in neuroscience. Here, Applicants demonstrate low intensity ultrasound as a non-invasive trigger to activate neurons in the nematode, *Caenorhabditis elegans*. Applicants show that neuron-specific misexpression of TRP-4, the pore-forming subunit of a mechanotransduction channel, activates those cells in response to ultrasound stimuli and initiates behavior. Applicants suggest that this method can be broadly used to manipulate cellular functions in vivo.

To probe the effects of ultrasound on neuronal function, Applicants chose the nematode *C. elegans*, with its small nervous system consisting of just 302 neurons (J. G. White, E. Southgate, J. N. Thomson et al., *Phil. Transact. R. Soc. Lond. B* 314, 1 (1986)), and strong correlations between individual neurons and robust behaviors (M. de Bono and A. V. Maricq, *Annu Rev Neurosci* 28, 451 (2005); C. I. Bargmann, *WormBook,* 1 (2006); R. O'Hagan and M. Chalfie, *Int Rev Neurobiol* 69, 169 (2006)).

Example 1: Imaging Setup Delivers Ultrasound Waves to Animals

Figure 1C:
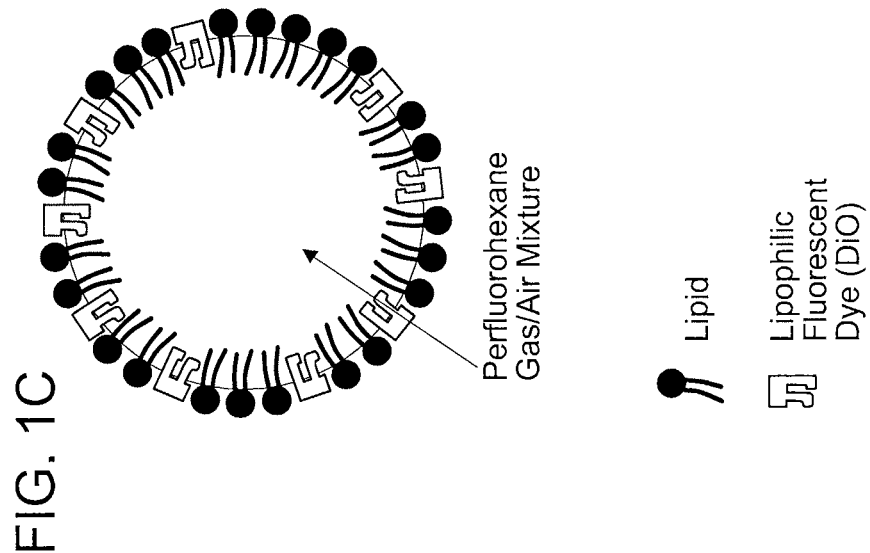
Figure 1B:
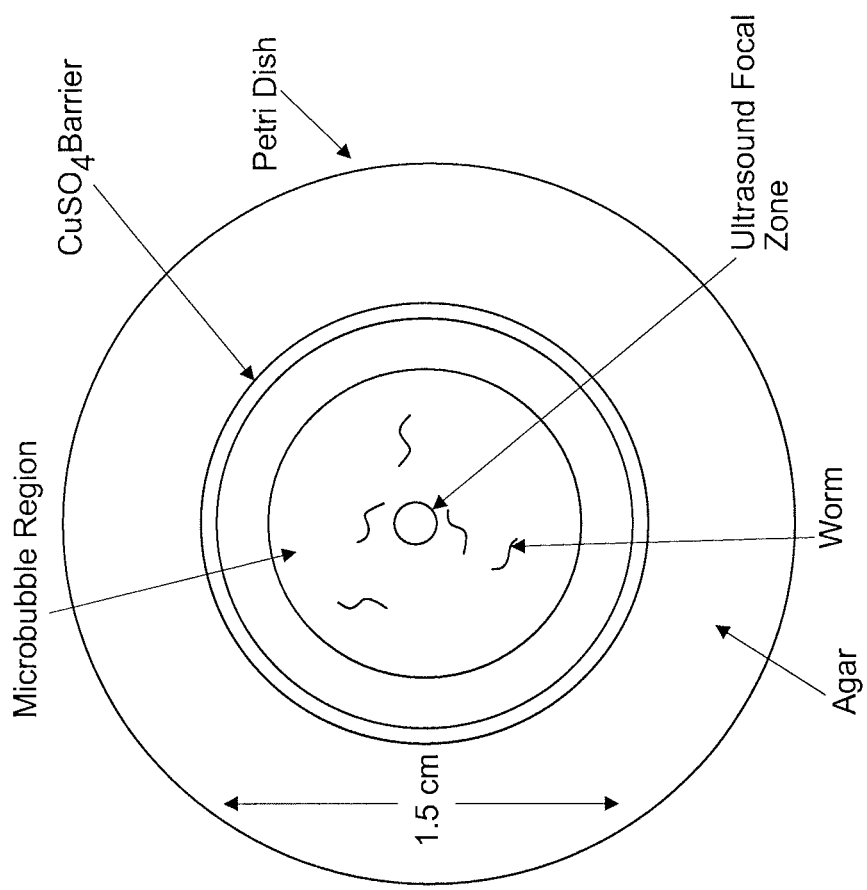
Figure 1D:
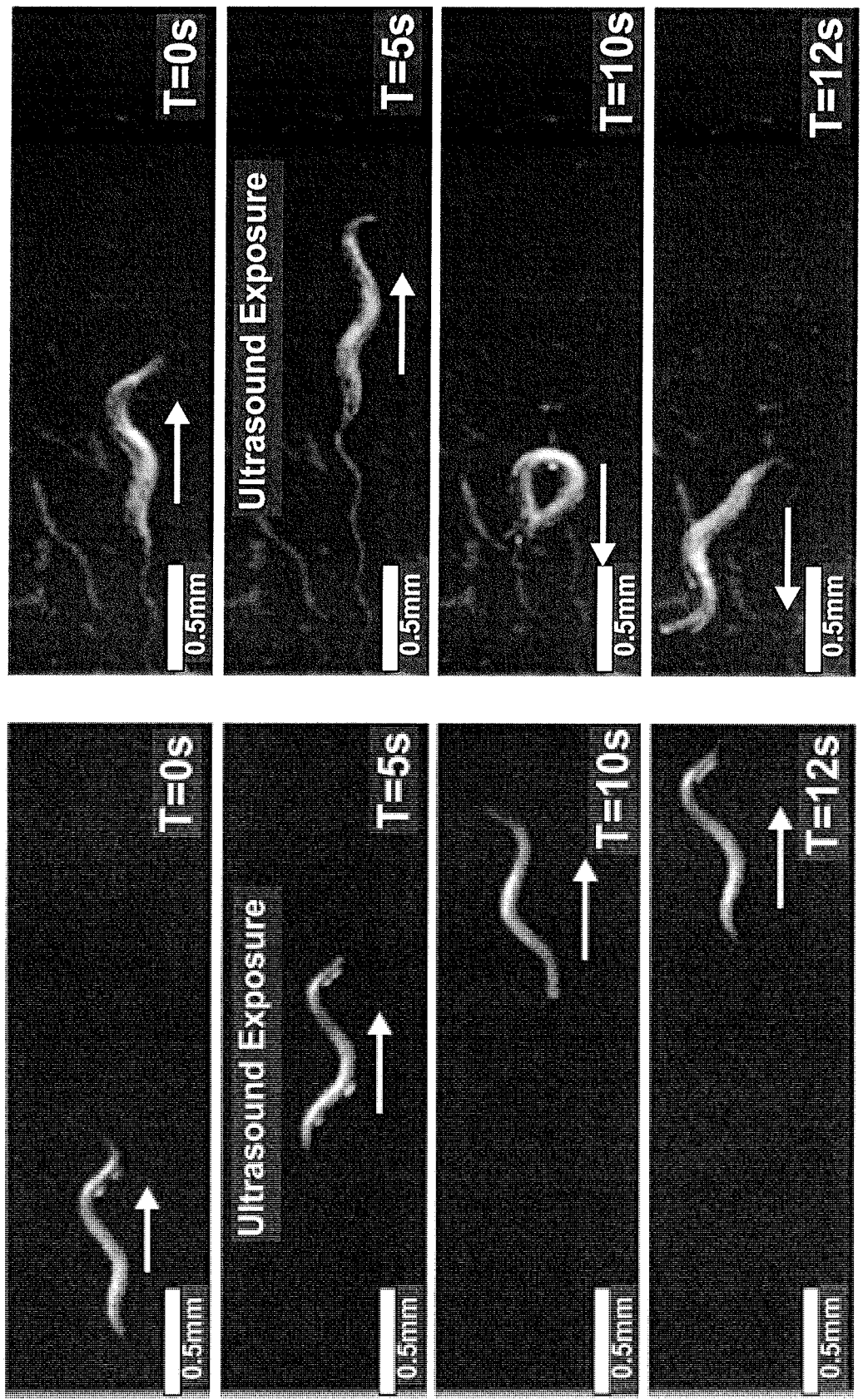
Figure 8B:
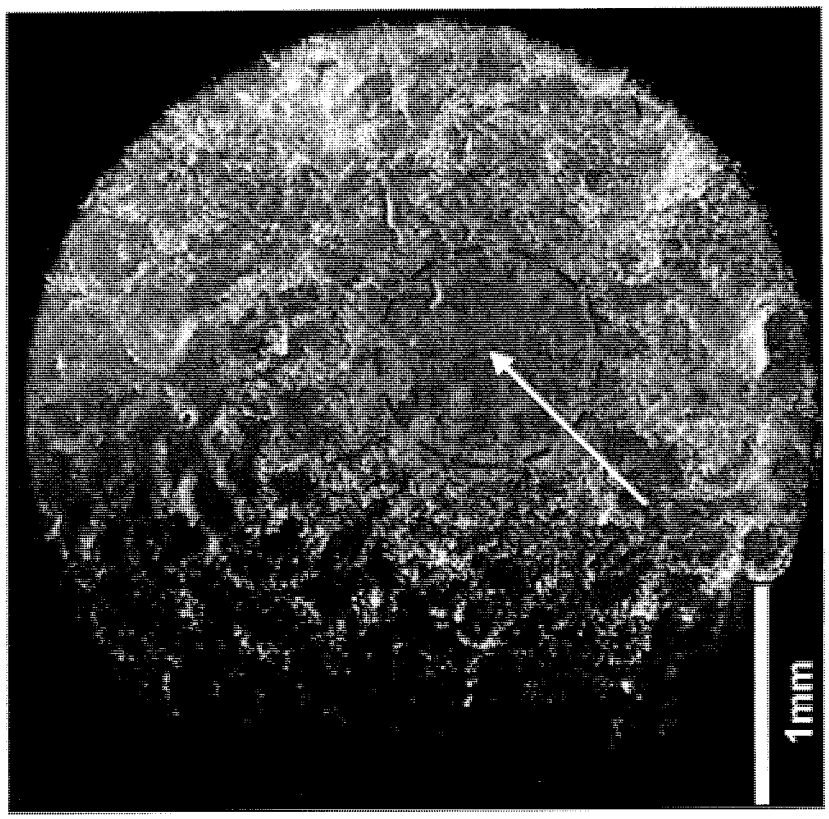
FIG. 8A, FIG. 8B, and FIG. 8C: Ultrasound stimulus modifies microbubble distribution.
Figure 8A:
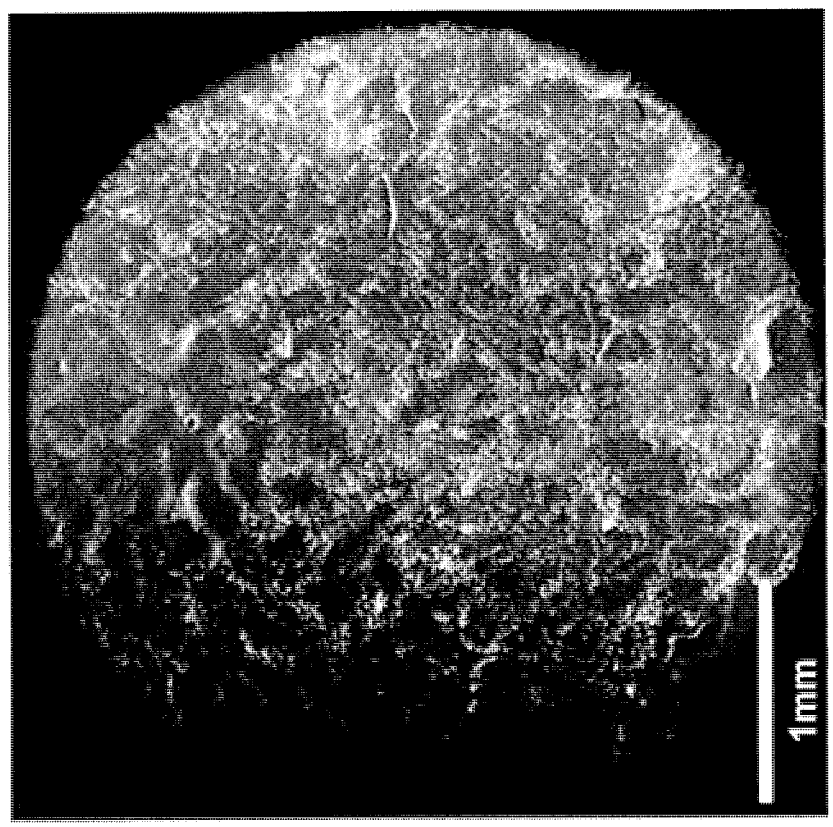
Figure 8C:
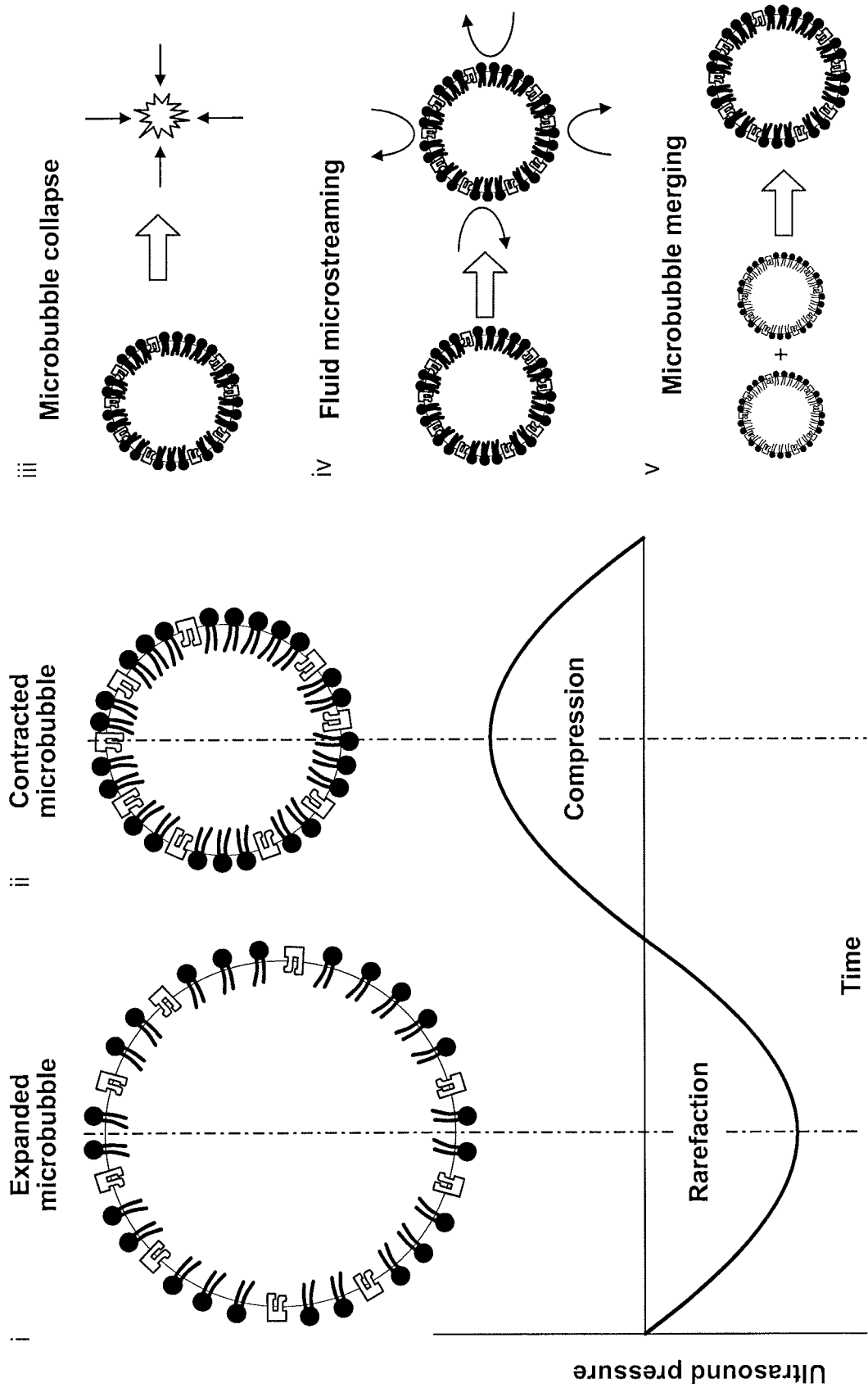
Figure 12:
FIG. 12 provides two panels showing damage to worms through multiple exposures to high peak negative pressure ultrasound in the presence of microbubbles. The worm displays a normal curved sinusoidal body position before exposure to the ultrasound (left). After exposure to 10 pulses of 0.9 MPa peak negative pressure ultrasound with a 1 Hz repetition rate the worm displays abnormalities in maintaining a normal body position and locomotion behavior is inhibited indicating damage has occurred (right).
Figure 12:
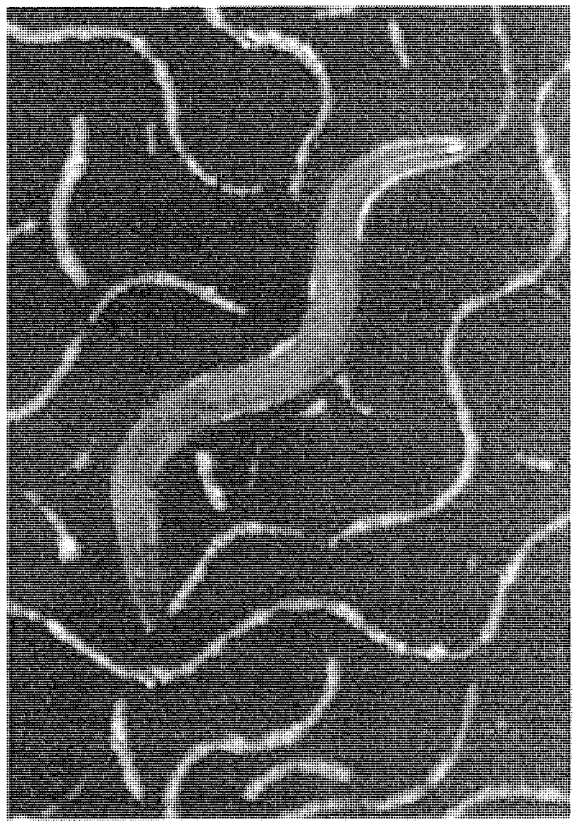

To investigate the role of ultrasound on *C. elegans* behavior, Applicants developed a novel imaging setup (FIG. 1A). Low intensity ultrasound was generated from a transducer and focused onto an agar plate where animals were corralled into a small area using a copper solution (FIG. 1B). Applicants' setup allowed for the ultrasound wave to be focused to a 1 mm diameter circular area at the agar surface (FIGS. 8A-8C). The whole setup was placed in a large tank filled with water to facilitate uniform transduction of the ultrasound wave. Previous studies have shown that at high ultrasound intensities (>2.5 MPa) water vapor bubbles would form spontaneously and collapse rapidly, initiating shockwaves that would compromise the integrity of cell membranes (termed "cavitation") (C. K. Holland and R. E. Apfel, *J Acoust Soc Am* 88 (5), 2059 (1990); S. Bao, B. D. Thrall, and D. L. Miller, *Ultrasound Med Biol* 23 (6), 953 (1997)). Applicants confirmed these results in Applicants' assay setup and also observed damage to animals at these high ultrasound intensities (data not shown). Applicants chose to focus on low intensity ultrasound to eliminate these damaging effects and found that at these intensities ultrasound had no effect on animal behavior (FIGS. 1D and 1E). The entire setup was placed in a large tank filled with water to facilitate uniform transduction of the ultrasound wave. Depending on solution or tissue gas concentrations, high ultrasound peak negative pressures (>2.5 MPa) can create inertial cavitation with the resulting shockwaves compromising the integrity of cell membranes. Consistently, Applicants observed that animals exposed to multiple pulses of high ultrasound pressures were unable to maintain their normal body posture (FIG. 12). Therefore, Applicants chose to use low-pressure ultrasound, which does not cause these damaging effects, to stimulate animal behavior.

Applicants used data from a previous study to estimate the mechanical deformation of the low intensity ultrasound wave (A. P. Brysev, A. F. Bunkin, R. V. Klopotov et al., *Opt. Spectrosc.* 93 (2), 282 (2002)). Applicants estimate that at this intensity, the ultrasound wave is likely to pass through *C. elegans* causing a mechanical deformation of 0.005 nm, and hypothesized that this small change is unlikely to influence cellular functions in vivo. This hypothesis is consistent with previous studies, which have shown that mechanical changes of this magnitude do not modify either neurons or non-neurons (S. Ito, H. Kume, K. Naruse et al., *Am J Respir Cell Mol Biol* 38 (4), 407 (2008); K. Shibasaki, N. Murayama, K. Ono et al., *J Neurosci* 30 (13), 4601 (2010)).

Moreover, Applicants found that a single 10 ms duration ultrasound pulse of 2.25 MHz and peak negative pressures below 0.9 MPa had no effect on animal behavior. The mechanical disturbances of the fluid and tissue in the ultrasound focal zone take the form of compression and expansion deformations as well as bulk tissue distortions caused by acoustic radiation forces, but at low-pressures they were not large enough to influence *C. elegans* locomotion. Previous studies have shown that ultrasound waves can cause temperature changes in the focal zone. Applicants first estimated the temperature increase as a result of ultrasound exposure. In a previous study, a continuous 1.1 MHz ultrasound pulse with a peak negative pressure of 2.6 MPa increased the temperature of the surrounding media at the rate of 35° C./sec. Using these data, Applicants estimated that the temperature increase around the worms on the agar surface to be 0.04° C. for single ultrasound pulse at 0.9 MPa. Moreover, Applicants directly measured the magnitude of temperature change on the agar surface using a miniature thermocouple and found that an ultrasound peak negative pressure of 0.7 MPa caused a temperature increase of less than 0.1° C. This is a temperature stimulus that animals including *C. elegans* are unlikely to detect. Together, these results show that *C. elegans* is unlikely to respond to the temperature and mechanical changes induced by the low-pressure ultrasound wave.

Figure 4A:
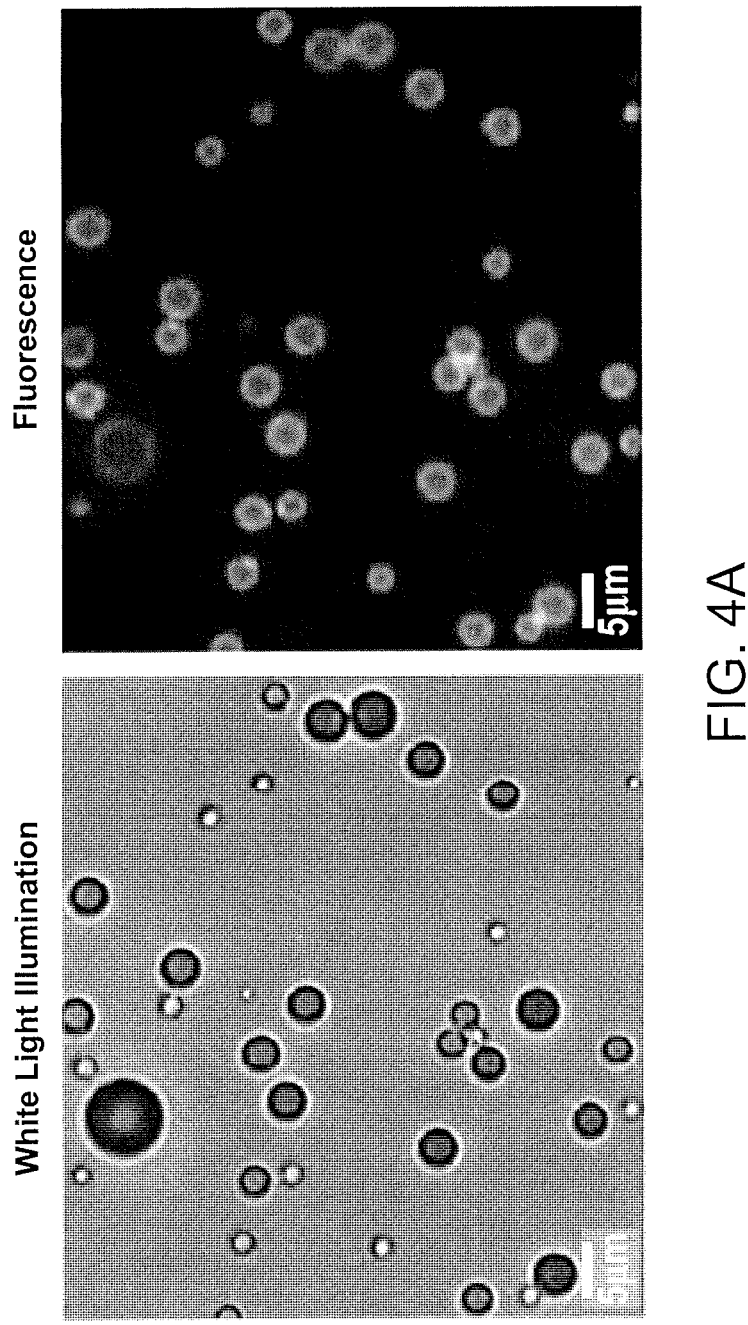
FIG. 4A, FIG. 4B, and FIG. 4C: Ultrasound stimulus modifies microbubble distribution around C. elegans.
Figure 4B:
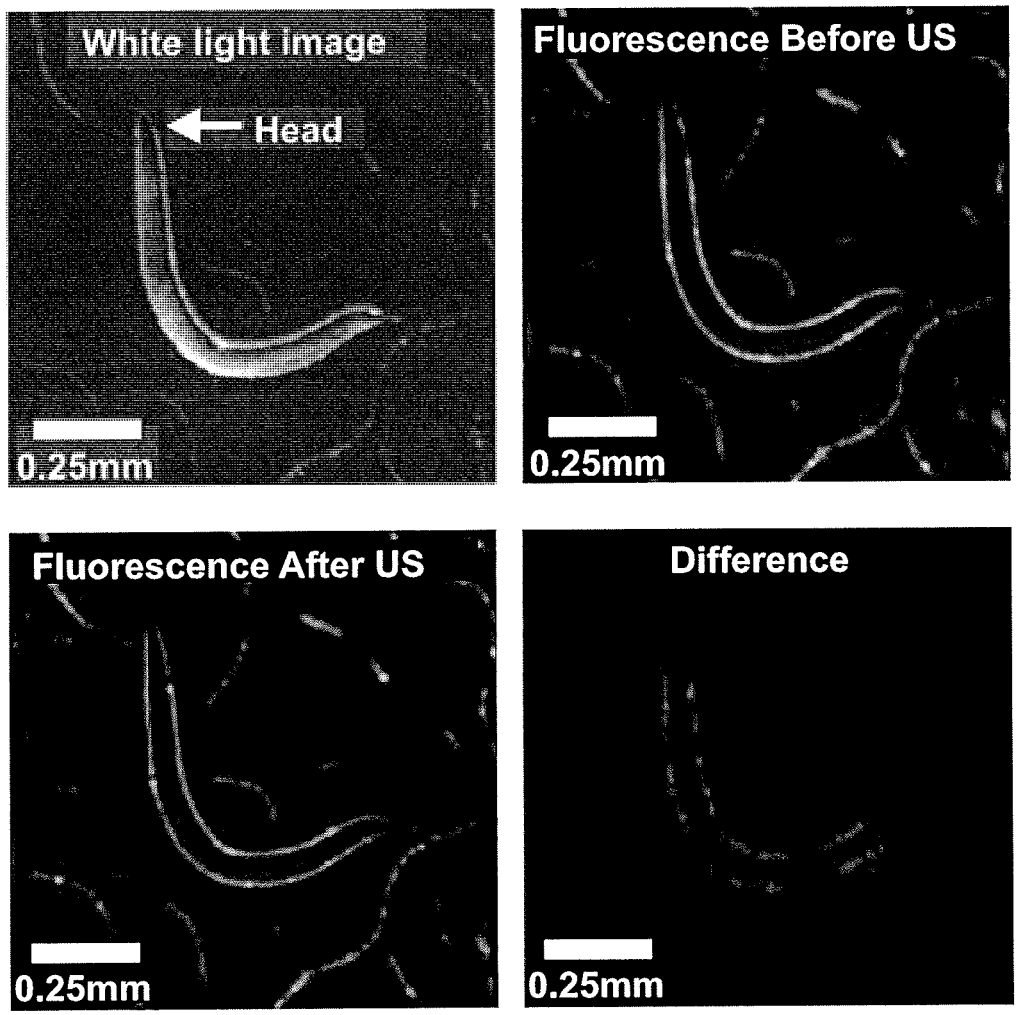
Figure 4C:
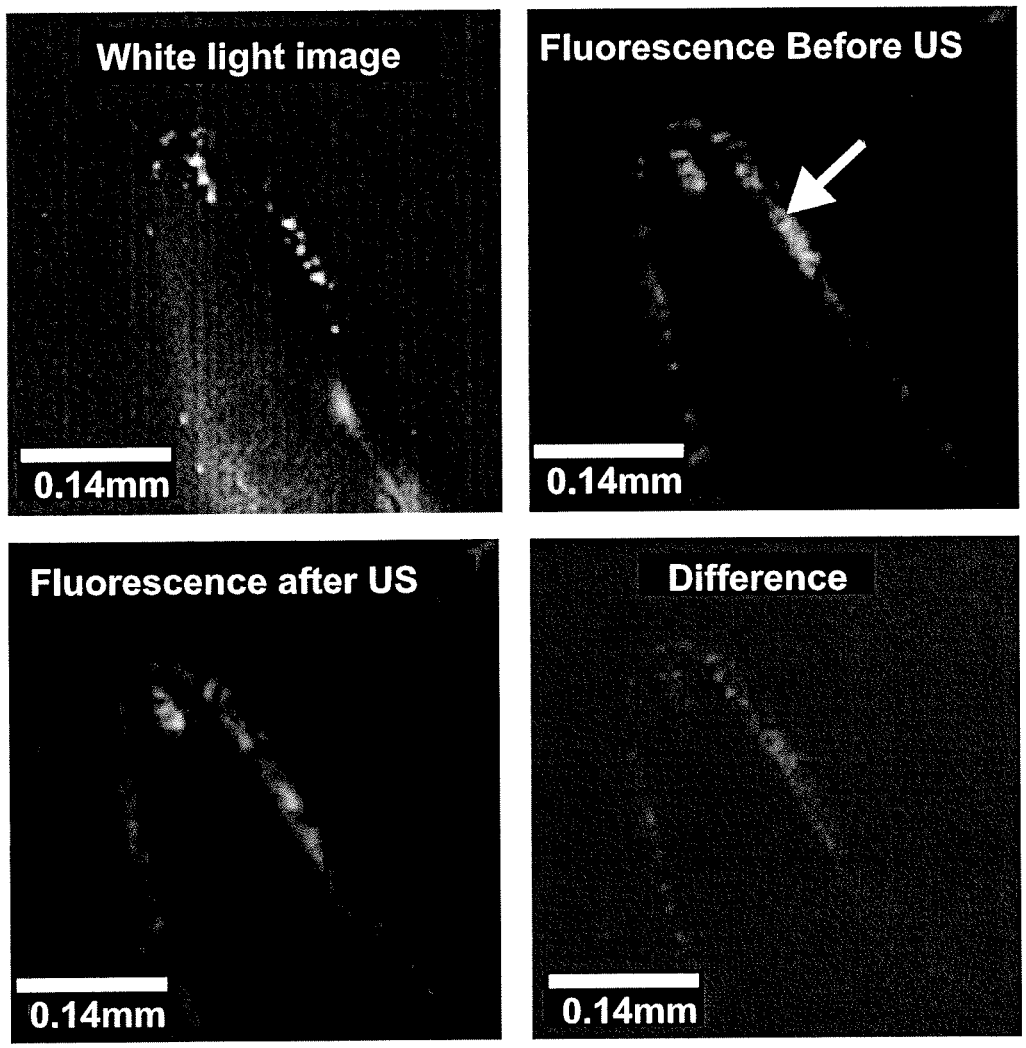
Figure 5A:
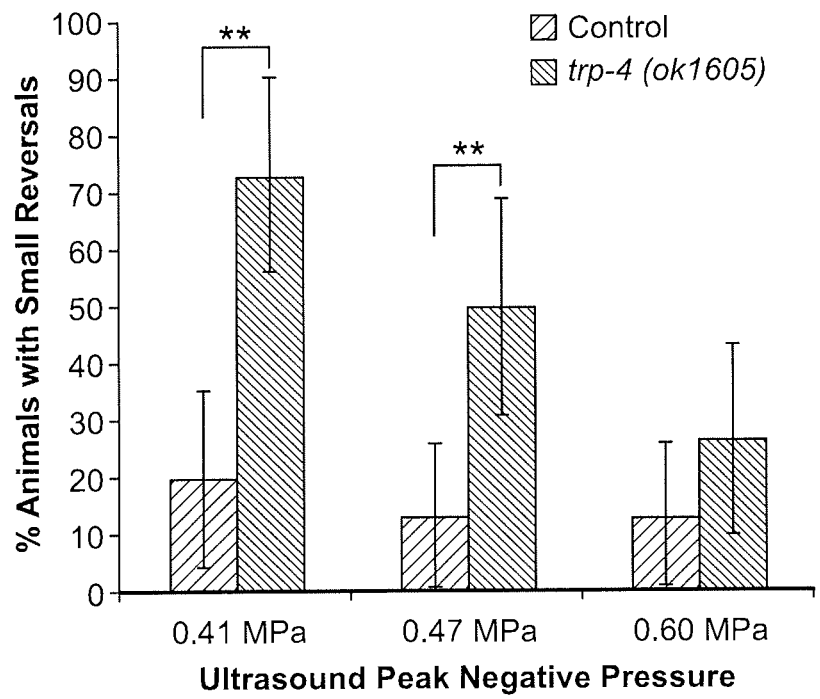
FIG. 5A, FIG. 5B, FIG. 5C, FIG. 5D, FIG. 5E, and FIG. 5F: Small reversal and omega bend responses to ultrasound stimuli. trp-4 mutants have altered number of small reversals as shown in FIG. 5A, but not omega bends as shown in FIG. 5B when compared to wild-type animals. Transgenics expressing trp-4 in ASH neurons also exhibit fewer numbers of small reversals as shown in FIG. 5C, but not omega bends as shown in FIG. 5D. AWC::trp-4 animals do not have any significant differences in their small reversal as shown in FIG. 5E or omega bend responses as shown in FIG. 5F upon ultrasound stimulation. Averages and 95% confidence intervals are shown. ** p<0.01 by Fisher's exact t-test.
Figure 5B:
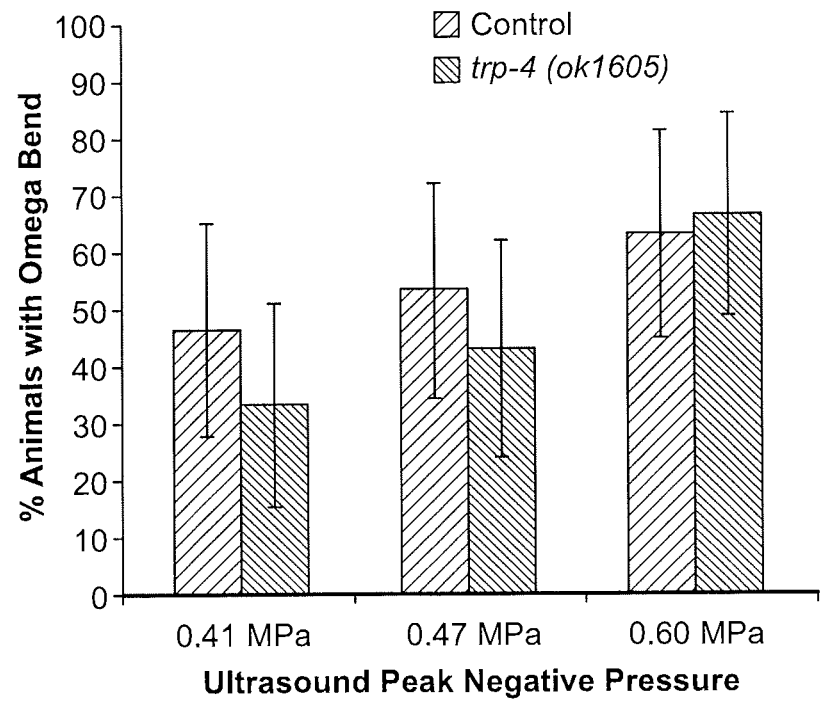
Figure 5C:
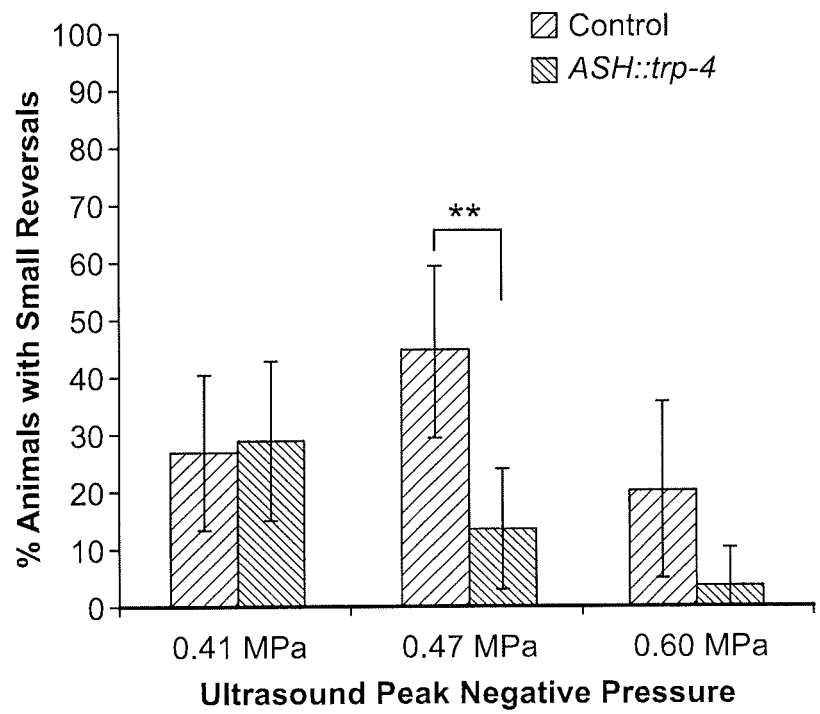
Figure 5D:
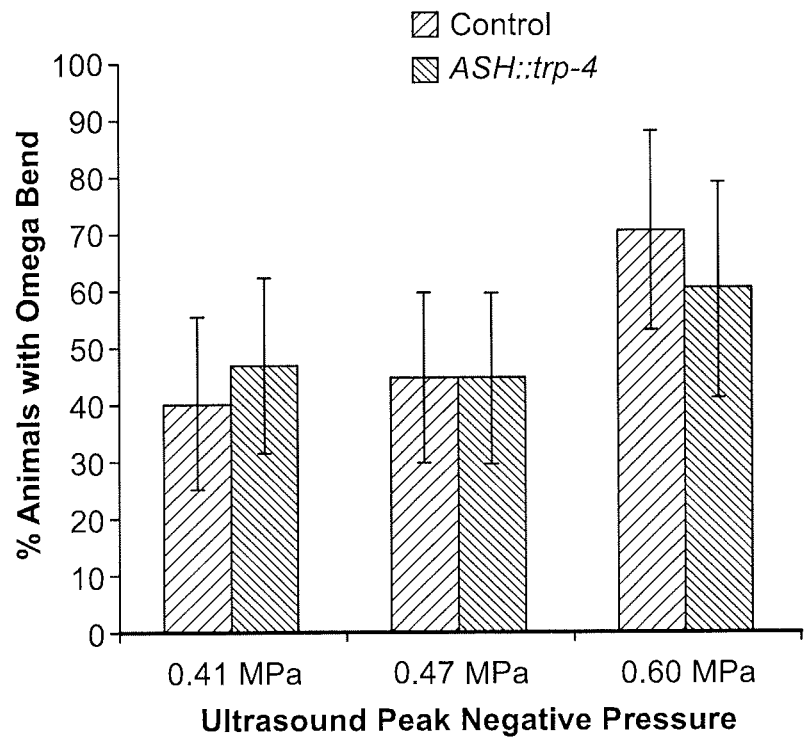
Figure 5E:
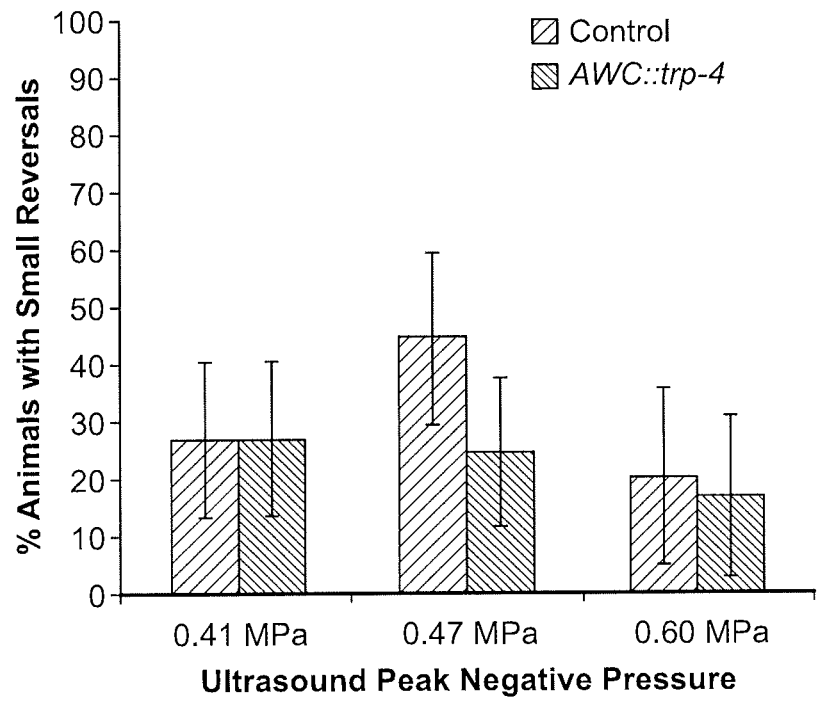
Figure 5F:
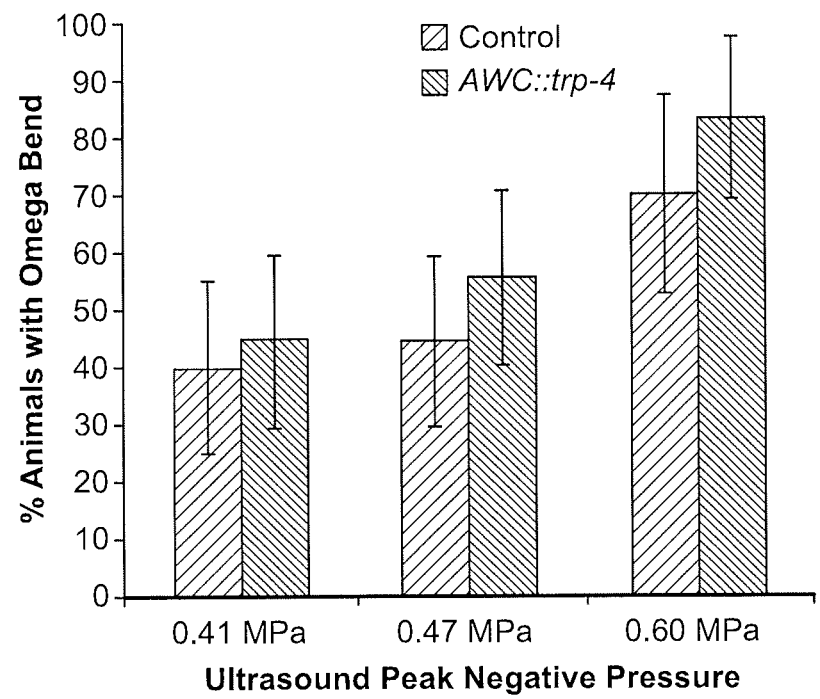
Figure 6A:
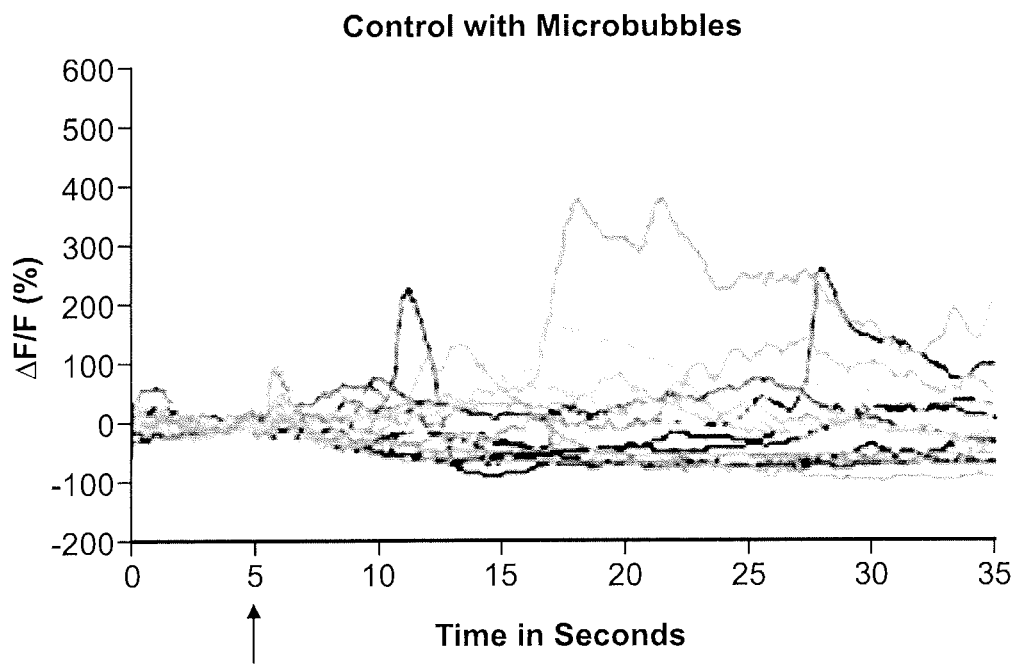
FIG. 6A, FIG. 6B, FIG. 6C, and FIG. 6D: AWC calcium responses to ultrasound stimulus. Ratio of change in fluorescence to baseline fluorescence in AWC neurons expressing the calcium sensor, GCaMP2.2b with as shown in FIG. 6A and without microbubbles as shown in FIG. 6B. AWC calcium responses in transgenic animals expressing trp-4 specifically in AWC neurons as shown with in FIG. 6C and without microbubbles as shown in FIG. 6D. Each color represents the response of an individual neuron to ultrasound stimulus presented at t=5 seconds.
Figure 6B:
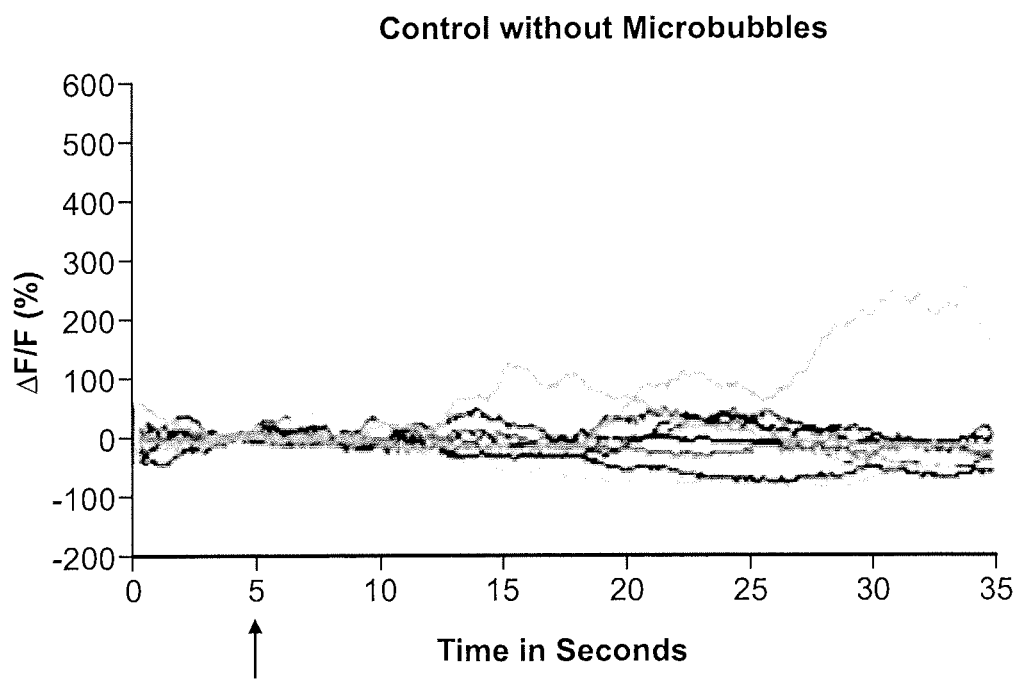
Figure 6C:
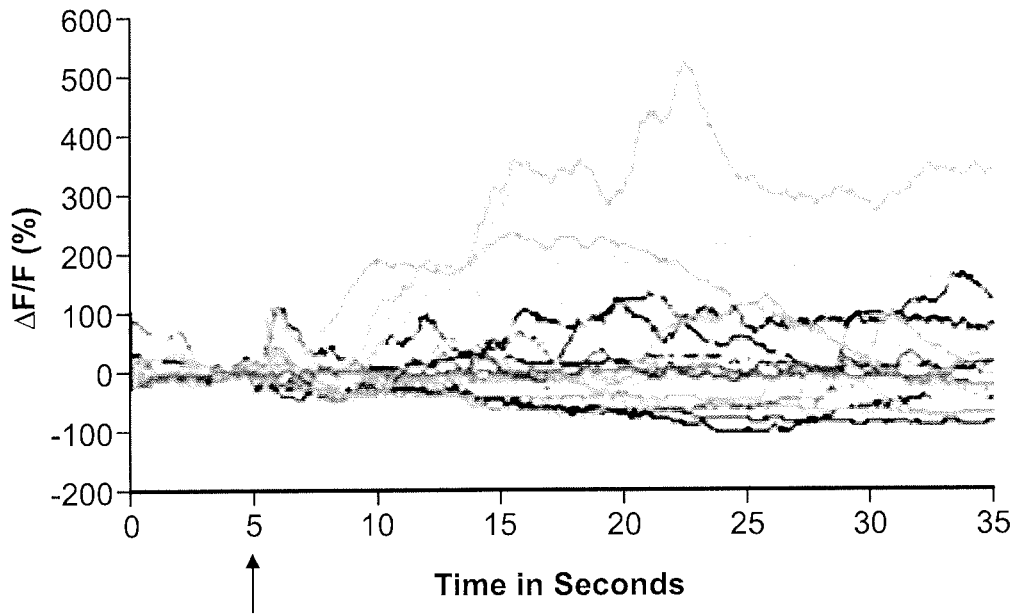
Figure 6D:
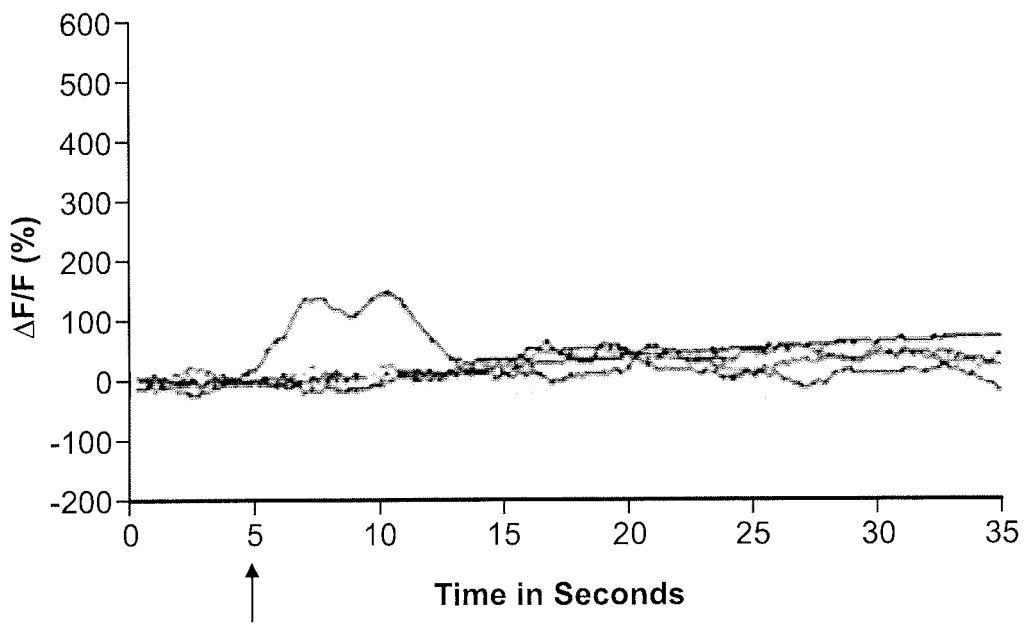
Figure 13B:
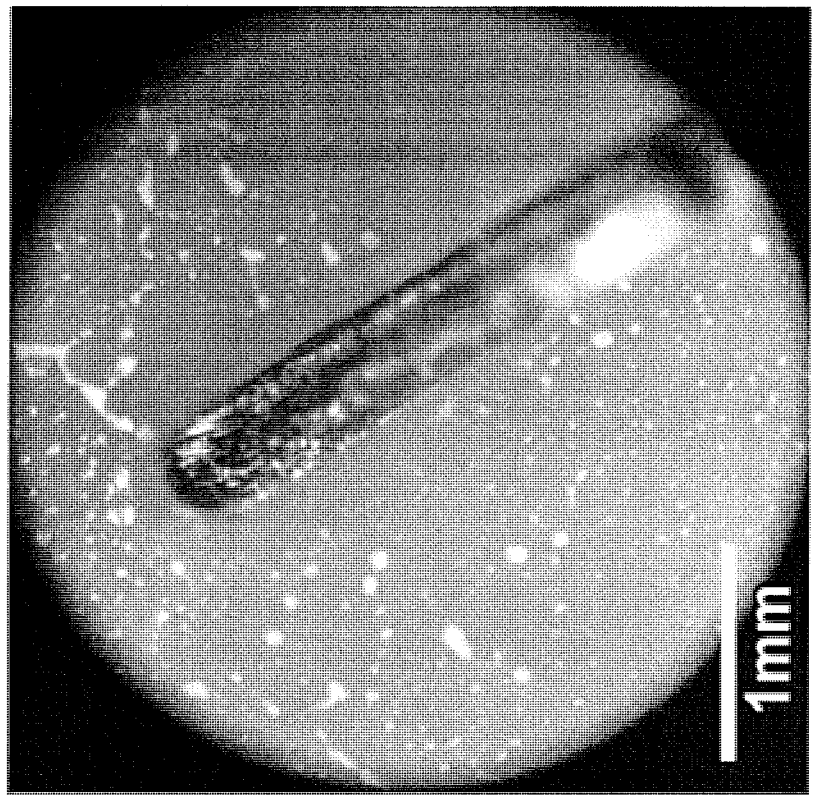
FIG. 13A and FIG. 13B provide two panels showing a thermocouple used for measuring temperature increases on agar surfaces. Images showing the probe touching the agar surface without as shown in FIG. 13A and with microbubbles as shown in FIG. 13B.
Figure 13A:
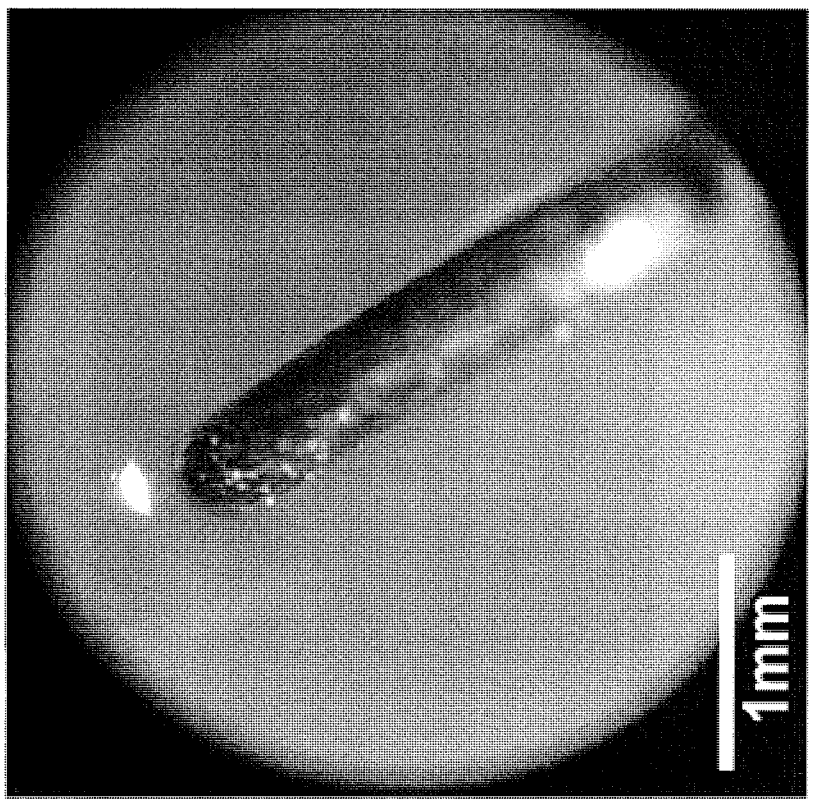
Figure 14A:
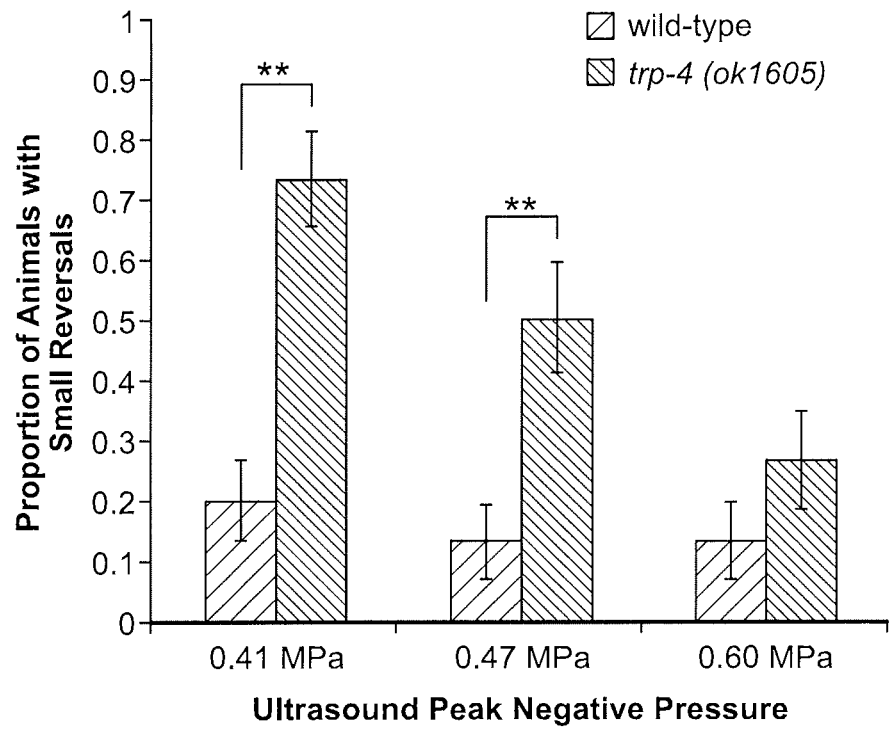
FIG. 14A, FIG. 14B, FIG. 14C, FIG. 14D, FIG. 14E, and FIG. 14F provide six graphs showing small reversal and omega bend responses to ultrasound stimuli in the presence of microbubbles. trp-4 mutants have altered number of small reversals as shown in FIG. 14A, but not omega bends as shown in FIG. 14B when compared to wild-type animals. Transgenics expressing trp-4 in ASH neurons also exhibit fewer numbers of small reversals as shown in FIG. 14C, but not omega bends as shown in FIG. 14D. AWC::trp-4 animals do not have any significant differences in their small reversal as shown in FIG. 14E or omega bend responses as shown in FIG. 14F upon ultrasound stimulation. Proportions and standard error of the proportion are shown. ** p<0.01 by Fisher's exact test.
Figure 14B:
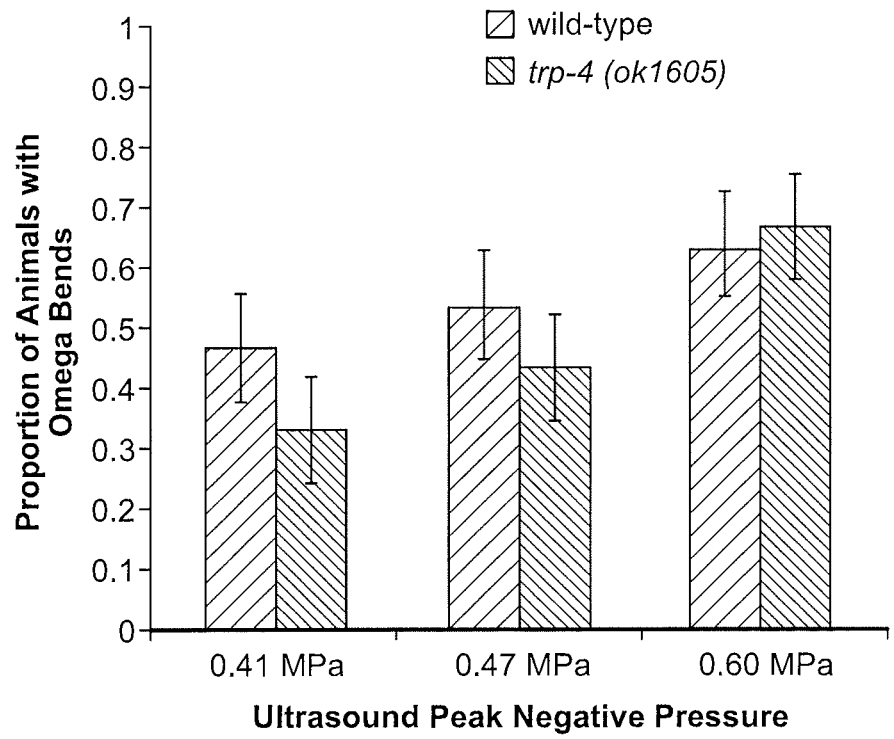
Figure 14C:
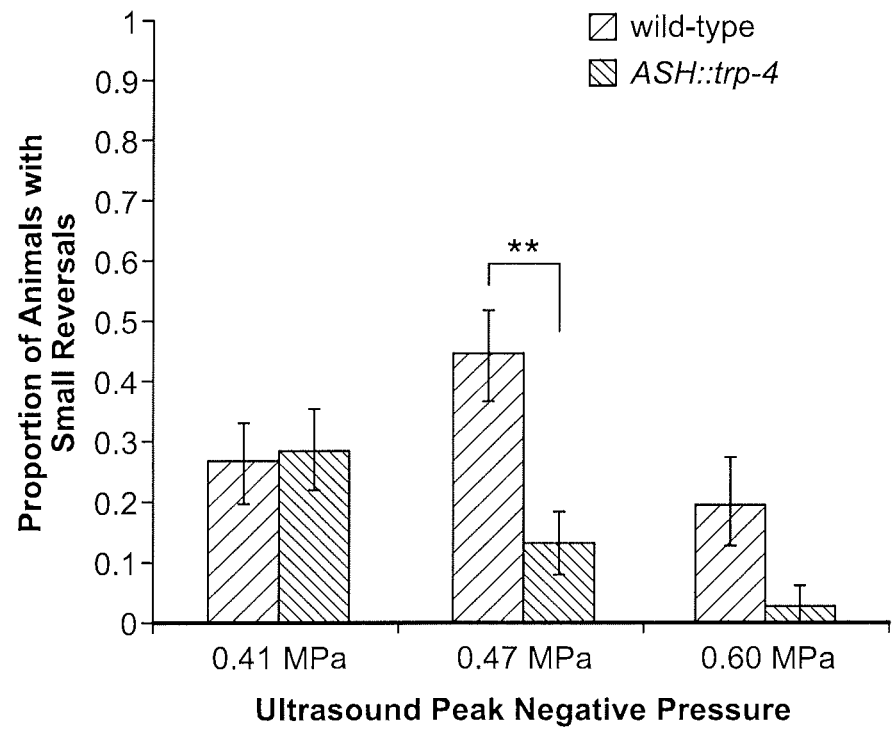
Figure 14D:
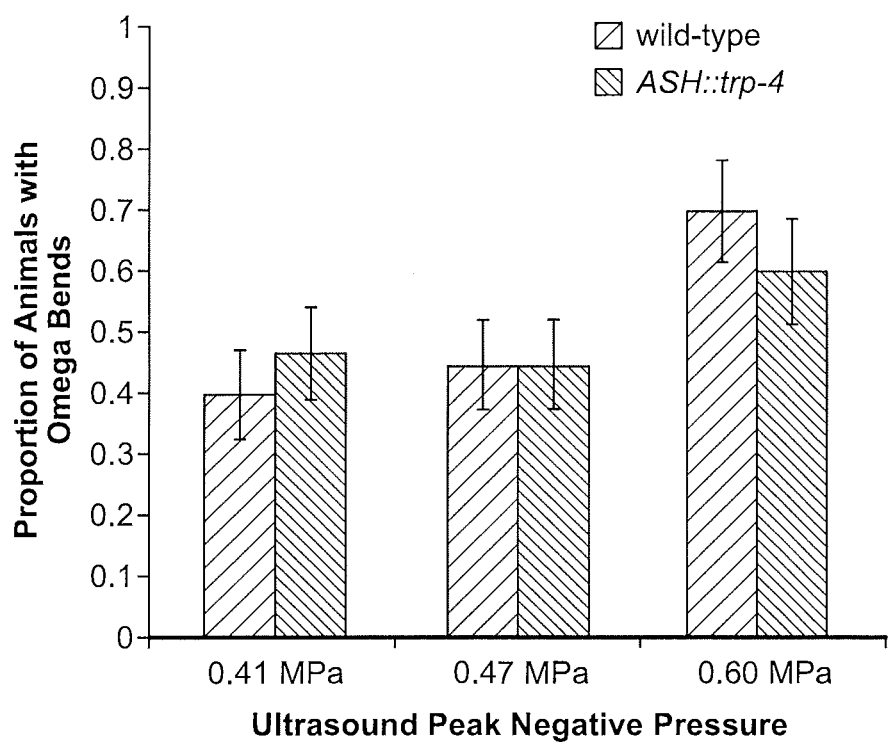
Figure 14E:
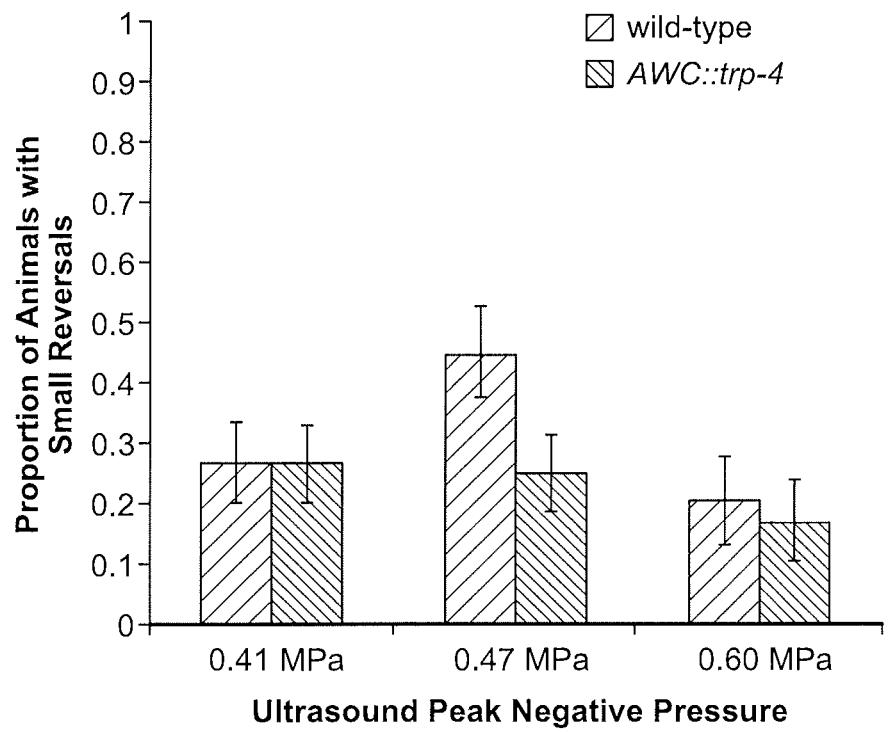
Figure 14F:
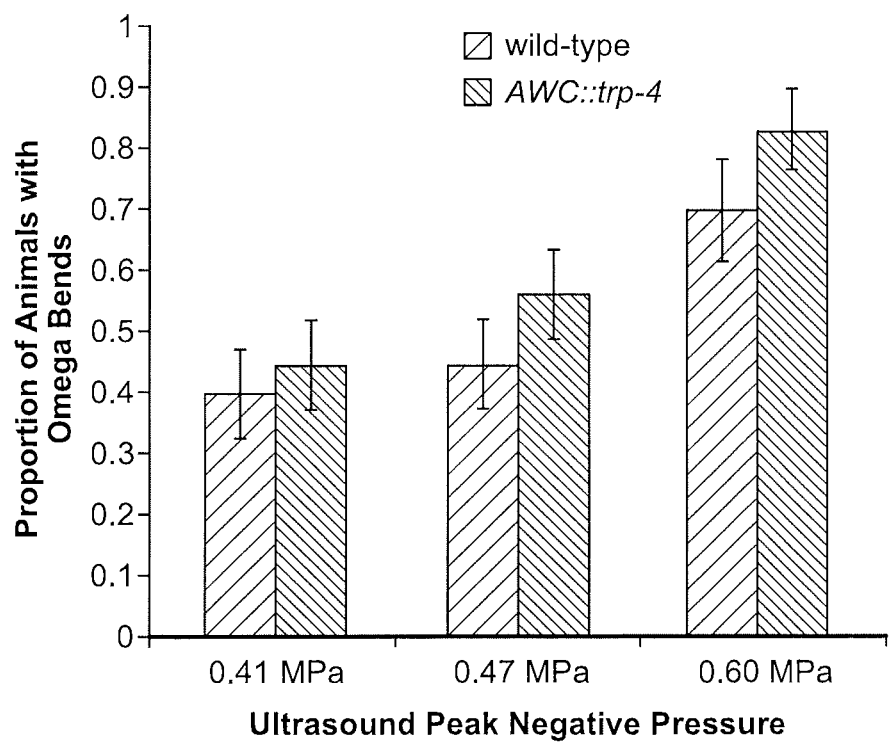
Figure 15G:
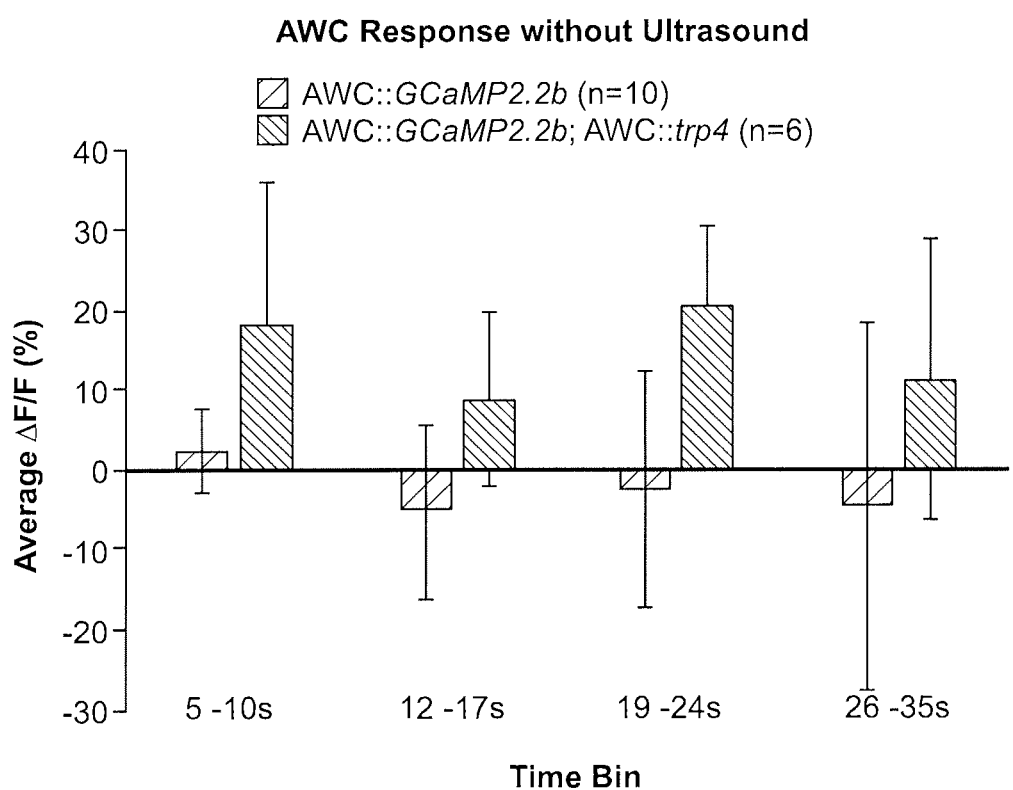

Example 2: Microbubbles Amplify the Mechanical Deformation of the Ultrasound Wave To amplify the ultrasound wave, Applicants included gas-filled microbubbles in Applicants' assay (FIG. 1C). Previous studies have shown that the majority of the ultrasound energy propagates through water and soft tissue as a longitudinal wave with alternating compression and rarefaction phases. These two phases create pressures that are alternately higher and lower than the ambient pressure level respectively. Applicants designed the microbubbles to respond to the mechanical deformations induced by an ultrasound pulse. Applicants filled the microbubbles with a stabilizing mixture of perfluorohexane and air that allows the compression and rarefaction phases of the ultrasound wave to shrink and expand the microbubbles from one half to four times their original diameters in a process known as stable cavitation. This occurs at the driving frequency of the underlying ultrasound pulse. Applicants found that animals showed a dramatic response to ultrasound when surrounded by microbubbles (FIGS. 1D and 1F). When the ultrasound wave was focused on the head of a worm, the animal immediately initiated a backward movement (termed "reversal") followed by a high-angled turn (labeled "omega bend") (FIGS. 1D and 13). These behaviors were scored as previously described (FIG. 13) (J. M. Gray, J. J. Hill, and C. I. Bargmann, *Proc Natl Acad Sci USA* 102 (9), 3184 (2005)) and quantified as shown (FIGS. 1E and 1F). The animal's behavioral responses were correlated with the intensity of the ultrasound wave (FIG. 1F) and the size of the microbubbles (FIG. 14). Applicants suggest that microbubbles (1-3 µm in diameter, mixed size) are likely to resonate with the 2.25 MHz ultrasound pulse causing large mechanical fluctuations around the animal and in turn, reversal behavior. To probe how microbubbles transduce the ultrasound wave and modify animal behavior Applicants analyzed microbubbles labeled with fluorescent DiO (FIG. 1C). Applicants found that microbubbles are evenly distributed around the animal and upon ultrasound stimulation some are destroyed, while others fuse and yet others move (FIGS. 4A-4C). These results suggest that these fluctuations in microbubbles around the animal are sufficient to initiate reversal behavior. Ultrasound waves have been previously shown to cause an increase in temperature in the focal zone (C. H. Farny, R. G. Holt, and R. A. Roy, *Biomedical Engineering, IEEE Transactions on* 57 (1), 175 (2010)). Using this dataset, Applicants estimate that the low-intensity ultrasound pulse (2.25 MHz) might cause a temperature increase of 0.04° C. on the agar surface, a stimulus that animals including *C. elegans* are unlikely to detect (I. Mori, H. Sasakura, and A. Kuhara, *Curr Opin Neurobiol* 17 (6), 712 (2007); D. A. Clark, C. V. Gabel, H. Gabel et al., *J*

Neurosci 27 (23), 6083 (2007)). Taken together, these results suggest that mechanical distortions around the worm transduce the ultrasound stimulus and initiate behavioral changes.

Example 3: TRP-4 Stretch Sensitive Ion Channels Sensitize Neurons to Ultrasound

Figure 2A:
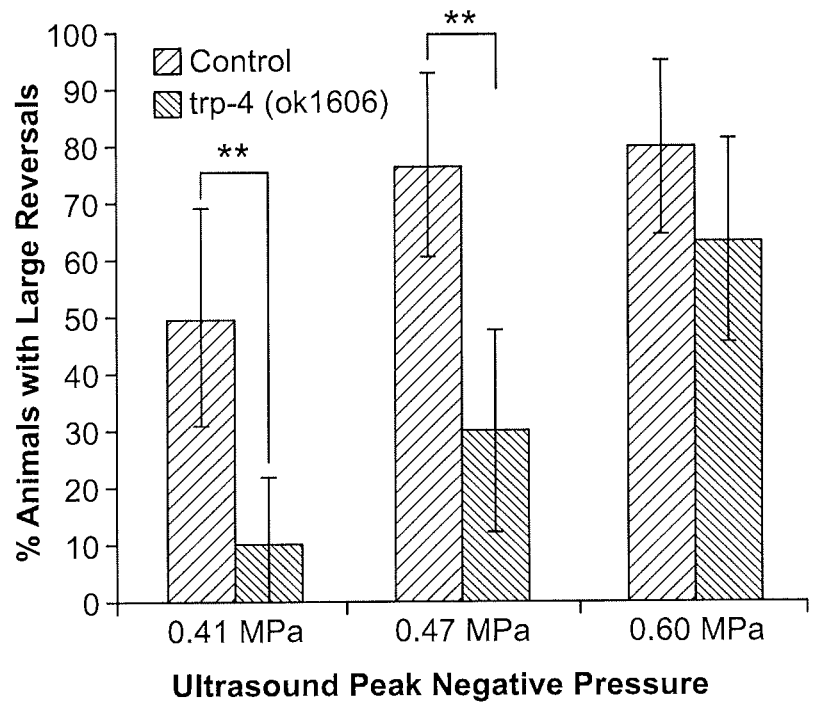
FIG. 2A, FIG. 2B, FIG. 2C, FIG. 2D, FIG. 2E, and FIG. 2F: TRP-4 expression activates ASH and AWC neurons.

Applicants hypothesized that ultrasound is a mechanical stimulus that require specific mechanotransduction channels to transduce the signals in individual neurons. Applicants tested the ability of TRP-4, a pore forming cation-selective mechanotransduction channel (L. Kang, J. Gao, W. R. Schafer et al., Neuron 67 (3), 381 (2010); W. Li, Z. Feng, P. W. Sternberg et al., Nature 440 (7084), 684 (2006)), to transduce this ultrasound induced mechanical stimulus. This channel is specifically expressed in a few C. elegans neurons, the four CEPs (CEPDL, CEPDR, CEPVL and CEPVR) and the two ADE (ADEL and ADER) dopaminergic neurons and the DVA and DVC interneurons (L. Kang, J. Gao, W. R. Schafer et al., Neuron 67 (3), 381 (2010); W. Li, Z. Feng, P. W. Sternberg et al., Nature 440 (7084), 684 (2006)). TRP-4 is both necessary and sufficient to generate mechanoreceptor currents in CEP neurons. Applicants found that animals missing TRP-4 have reduced responses to specific intensities (0.41 and 0.47 MPa peak negative pressure) of ultrasound stimulation, which suggests that this channel is required to generate reversals (FIG. 2A). In contrast, trp-4 mutants do not show any significant change in their omega bend behaviors upon ultrasound stimulation (FIGS. 5A-5F). At higher intensities, trp-4 mutants have similar responses compared to wildtype, which suggests that there is an alternate pathway that detects ultrasound at these intensities. Collectively, these results suggest that TRP-4 might be activated in response to ultrasound with peak negative pressure levels less than 0.5 MPa and modifies neurons involved in generating small and large reversals.

Figure 2B:
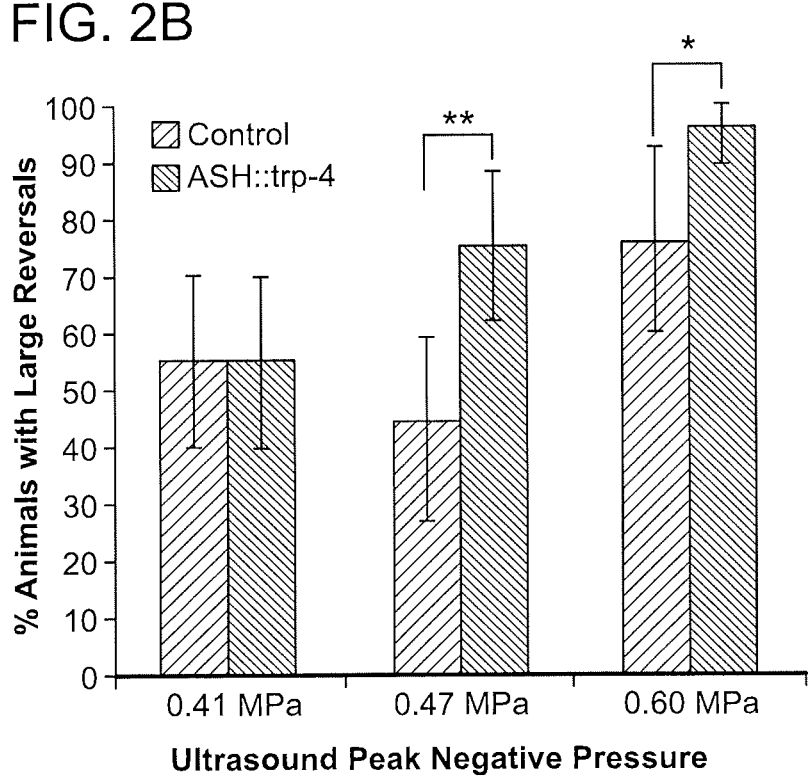
Figure 2C:
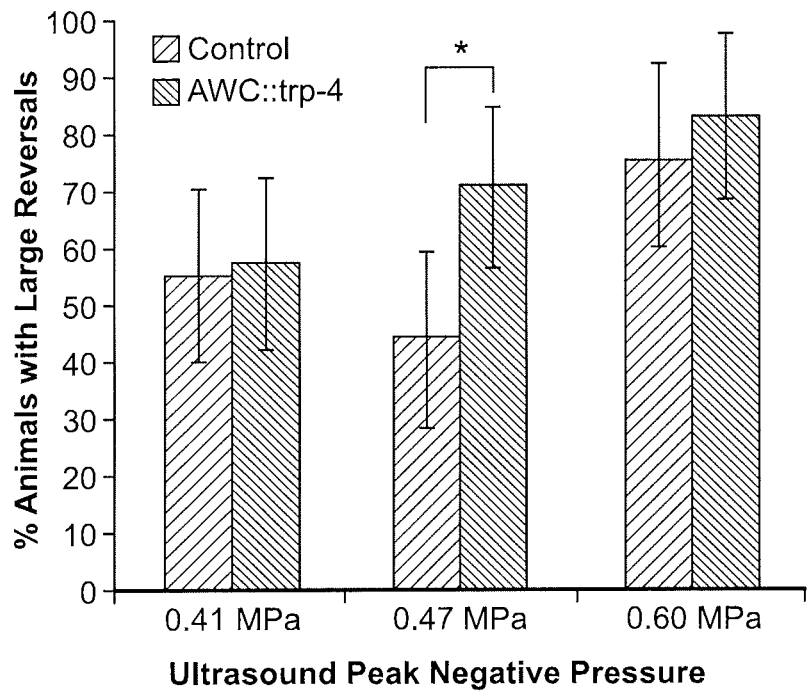
Figure 2D:
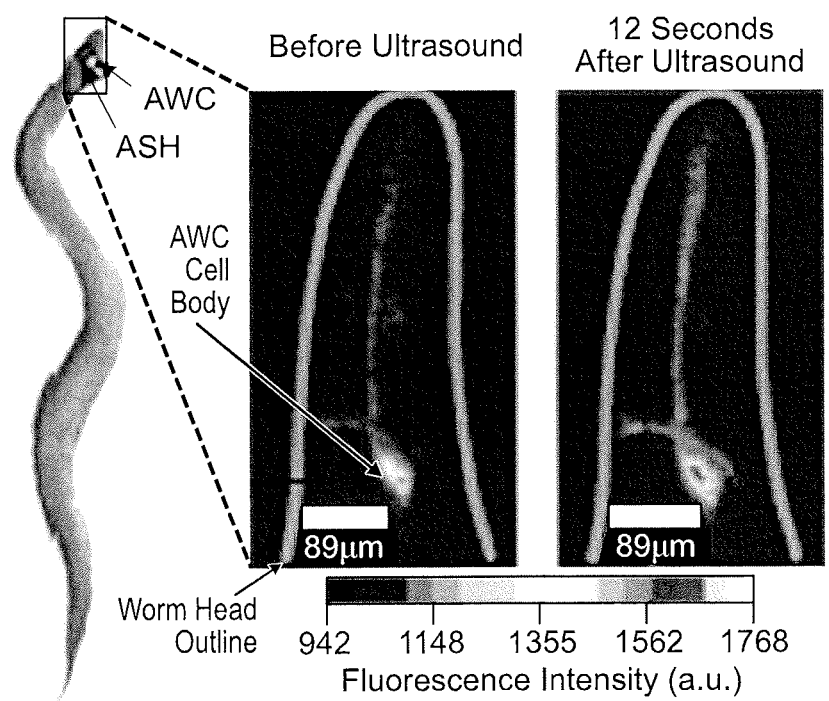
Figure 2E:
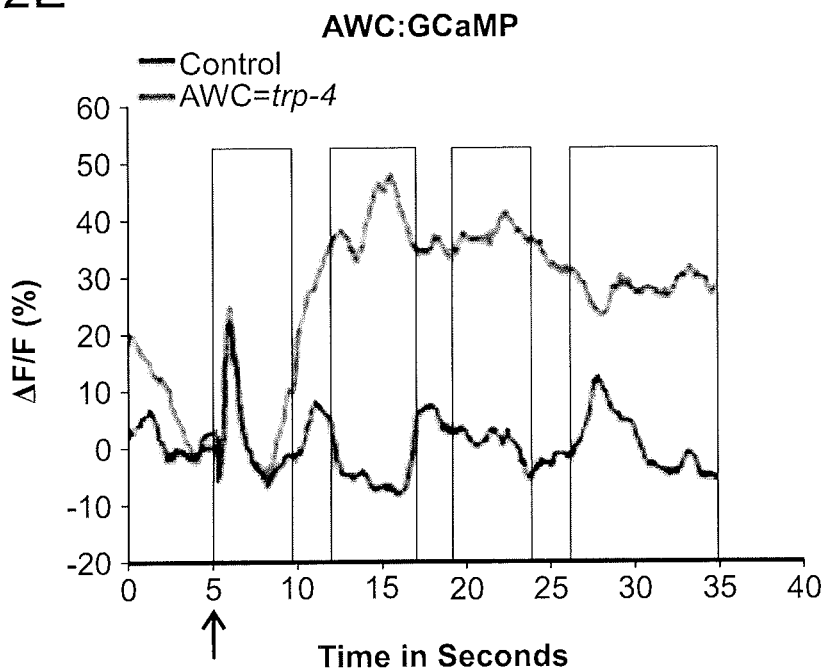
Figure 2F:
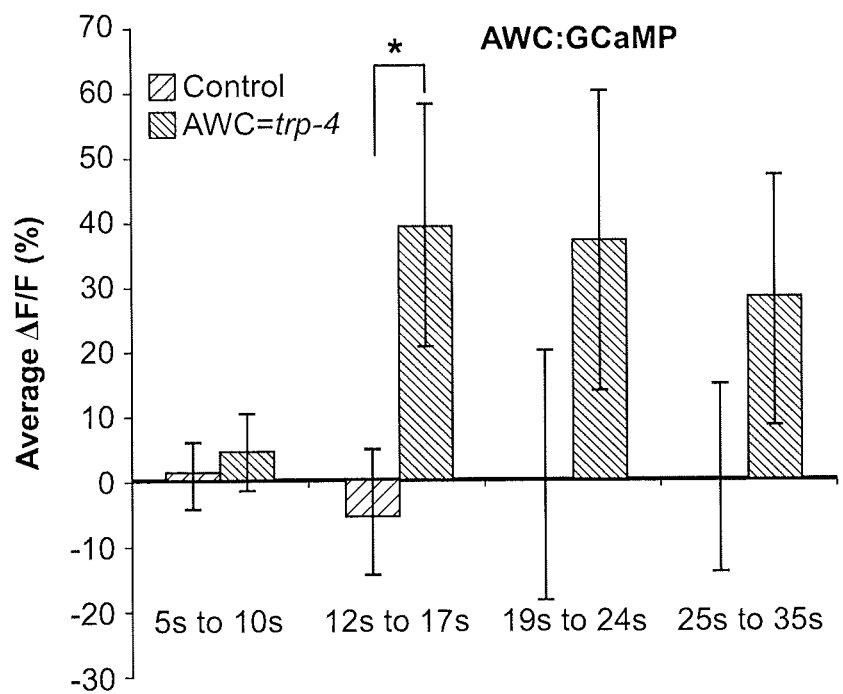

To test whether ultrasound sensitivity could be conferred to additional neurons, Applicants analyzed the behavior of transgenic animals misexpressing TRP-4 in specific chemosensory neurons. Applicants initially misexpressed this channel in ASH, a well-studied polymodal nociceptive neuron (M. A. Hilliard, C. Bergamasco, S. Arbucci et al., Embo J 23 (5), 1101 (2004)), whose activation leads to reversals and omega bends (Z. V. Guo, A. C. Hart, and S. Ramanathan, Nat Methods 6 (12), 891 (2009)). Consistently, Applicants found that ASH expression of TRP-4 generated a significant increase in reversals at ultrasound intensity with a peak negative pressure of 0.47 MPa (FIG. 2B). Moreover, Applicants found that these ASH::trp-4 transgenics do not show any change in their omega bend responses (FIG. 5), confirming that this channel specifically modifies the reversal neural circuit. Next, Applicants tested the effects of TRP-4 misexpression on function and behavior of the AWC sensory neuron. Previous results have implied that AWC activation is correlated with an increase in the animal's ability to generate reversals (S. H. Chalasani, N. Chronis, M. Tsunozaki et al., Nature 450 (7166), 63 (2007)). Applicants found that animals misexpressing TRP-4 in AWC neurons also initiated significantly more large reversals at the same ultrasound intensity of 0.47 MPa peak negative pressures, but not omega bends (FIGS. 2C and 5). To test whether ultrasound could directly stimulate AWC neurons, Applicants recorded the activity of these neurons in animals expressing the calcium indicator, GCaMP3 (L. Tian, S. A. Hires, T. Mao et al., Nat Methods 6 (12), 875 (2009)). Consistent with Applicants' behavioral data, Applicants found that ultrasound stimulation activated AWC neurons (FIGS. 2D-2F). Also, Applicants find that AWC responses are significantly reduced in the absence of microbubbles, which suggests that the ultrasound signals need to be amplified before they can modify neuronal functions (FIGS. 6A-6D). Consistent with the behavior data, Applicants observe that AWC neurons expressing TRP-4 show a significant increase in their activity a few seconds (t=12 to t=17 seconds) after the ultrasound stimulus (FIG. 2F). Both wild-type AWC neurons and those misexpressing TRP-4 showed a response lasting about 2-3 seconds immediately upon exposure to a single ultrasound pulse in the presence of microbubbles. However, Applicants also observed that AWC neurons misexpressing TRP-4 show a significant increase in their activity starting at 7 seconds after ultrasound exposure (t=12 seconds in FIG. 5F) and lasting for at least 5 seconds, which is not observed in wild-type neurons. This sustained increase in AWC calcium levels likely represents the activity of TRP-4, which could potentiate calcium entry into the neuron via other calcium channels. Interestingly, large reversals take approximately 10-20 seconds to complete, a time window where Applicants also observe sustained AWC calcium activity in the AWC:: trp-4 transgenics. The sustained AWC calcium activity observed in these AWC::trp-4 transgenics is likely correlated with the increased frequency of large reversals generated by these animals after ultrasound stimulation. Taken together, these results show that TRP-4 channels are sensitive to low-pressure ultrasound, and ectopic expression of these channels in sensory neurons causes correlated changes in neuronal activity and behavior.

Figure 16A:
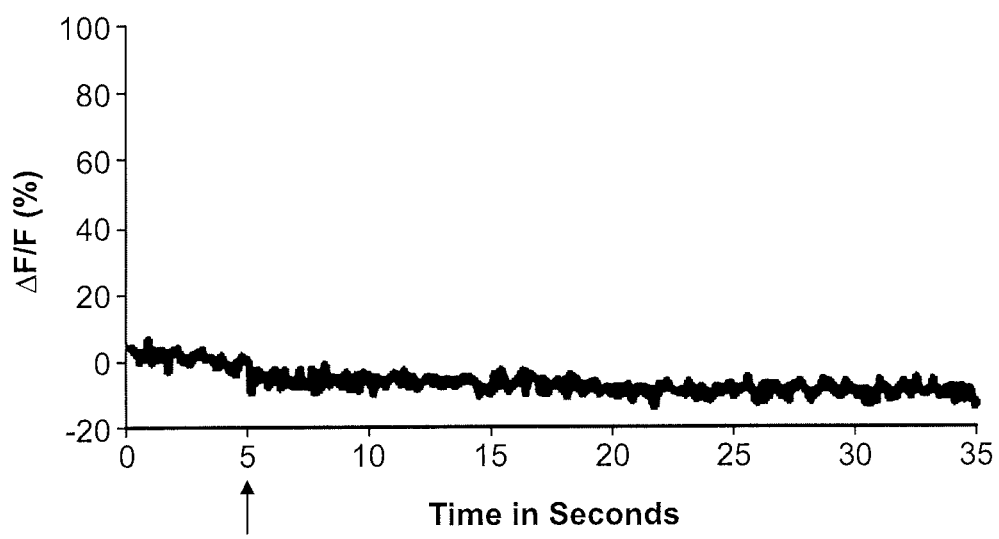
FIG. 16A and FIG. 16B provide two graphs showing that FLP neurons do not respond to ultrasound.
Figure 16B:
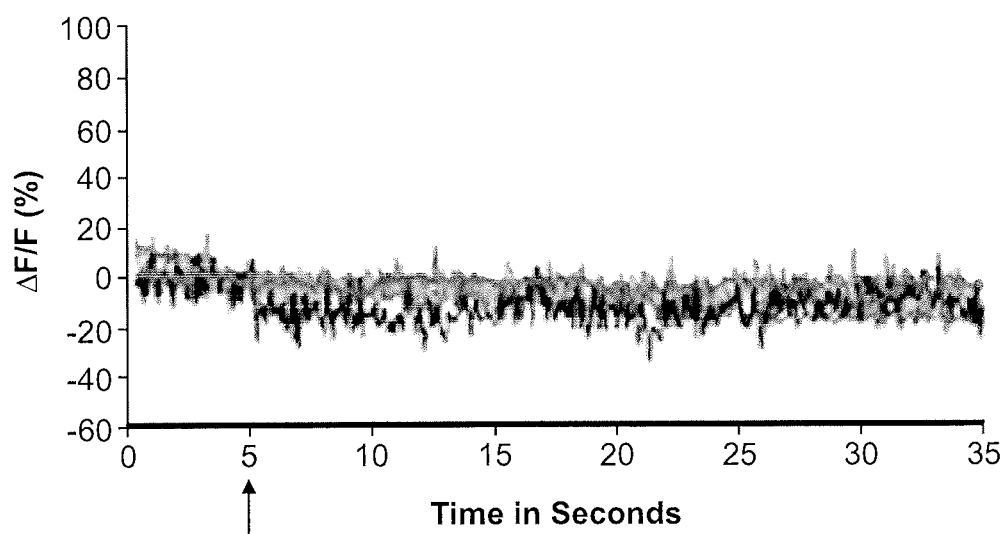
Figure 17A:
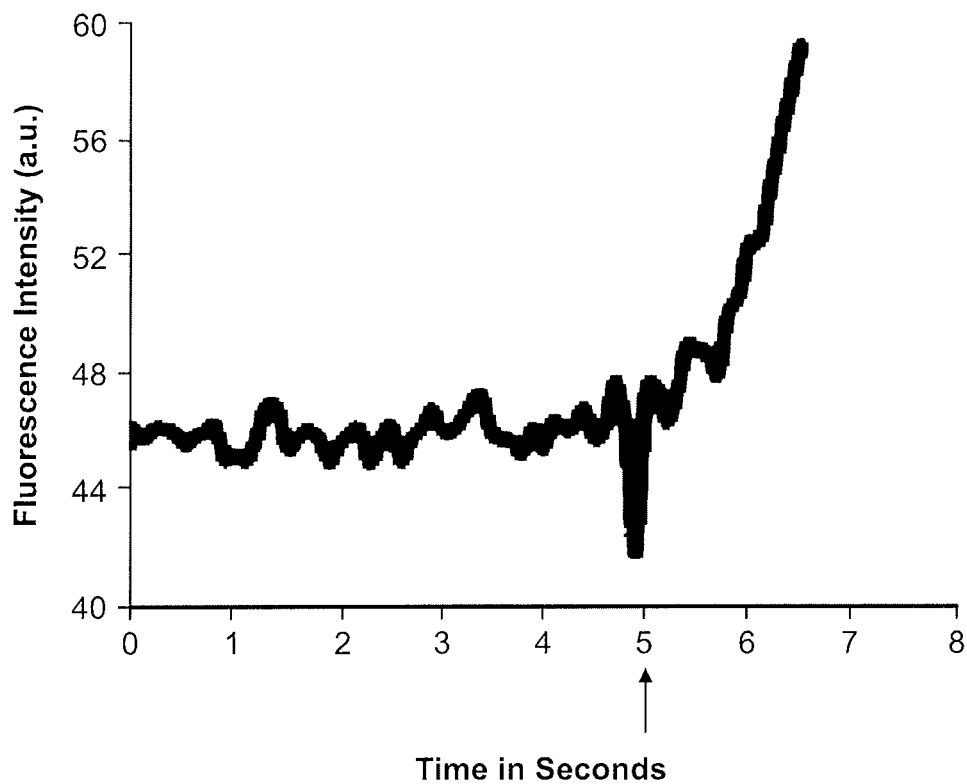
FIG. 17A, FIG. 17B, FIG. 17C, and FIG. 17D provide four panels showing that PVD responses depend on worm movement.
Figure 17B:
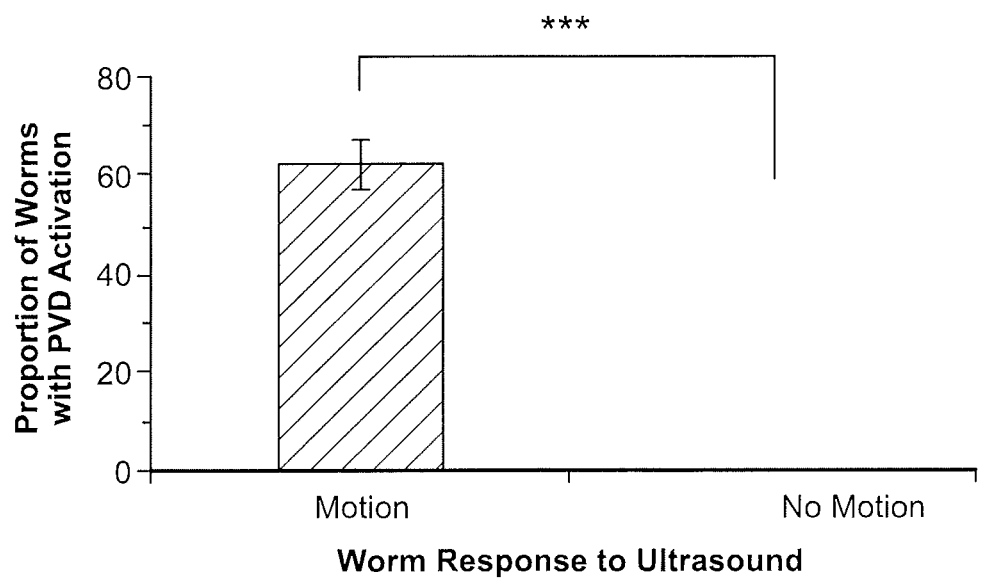
Figure 17C:
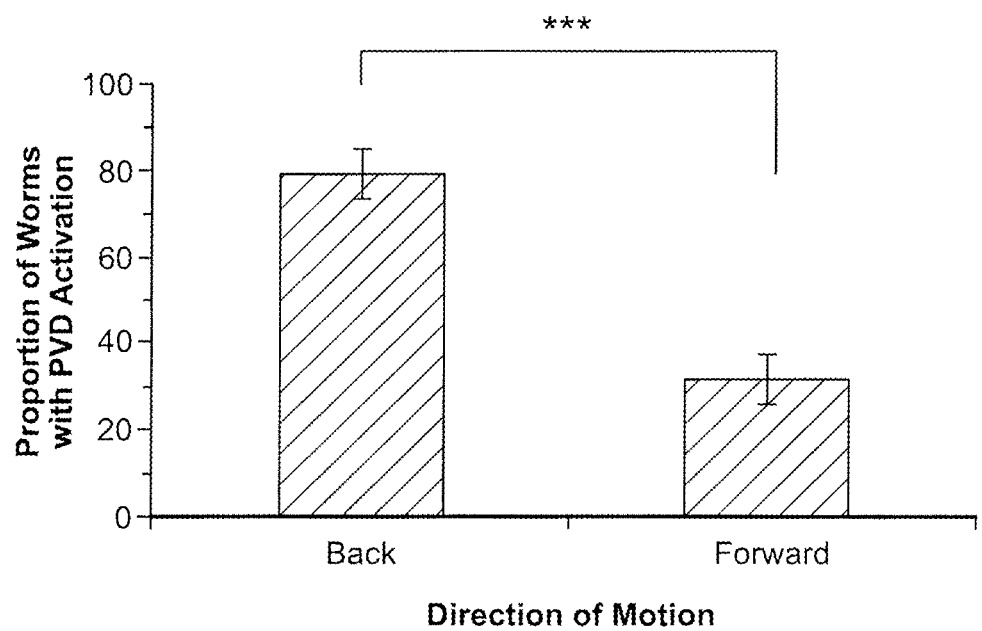
Figure 17D:
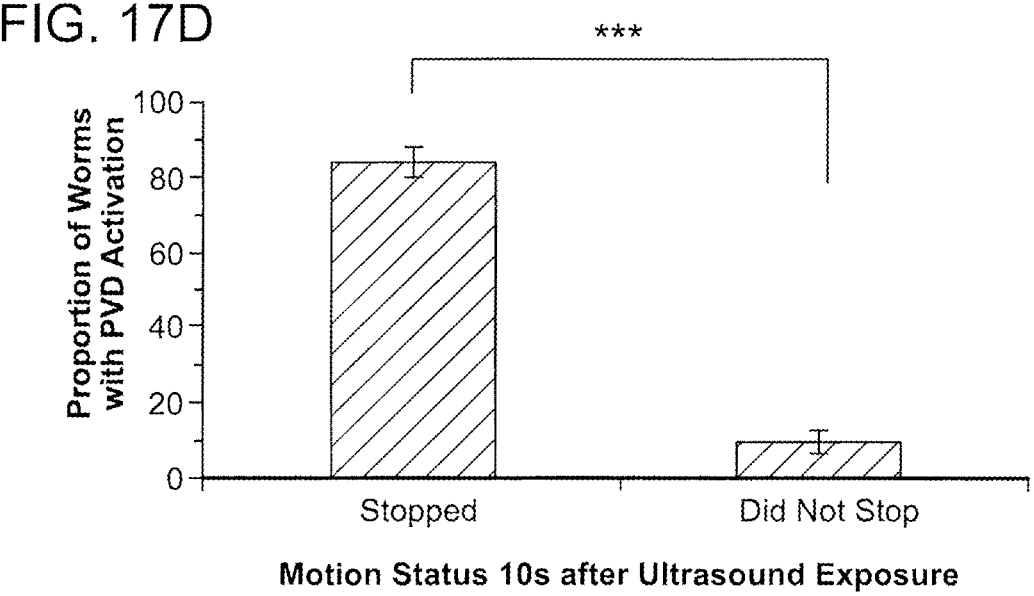

Interestingly, FLP neurons do not respond to ultrasound (FIG. 16). Microbubbles are present in all FLP recordings.

Figure 3A:
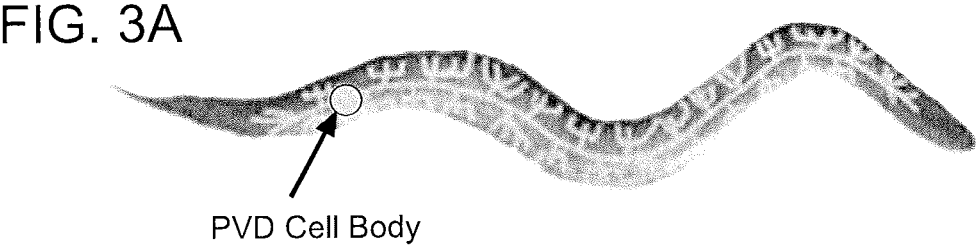
FIG. 3A, FIG. 3B, FIG. 3C, FIG. 3D, FIG. 3E, and FIG. 3F: PVD neurons inhibit reversals.
Figure 3B:
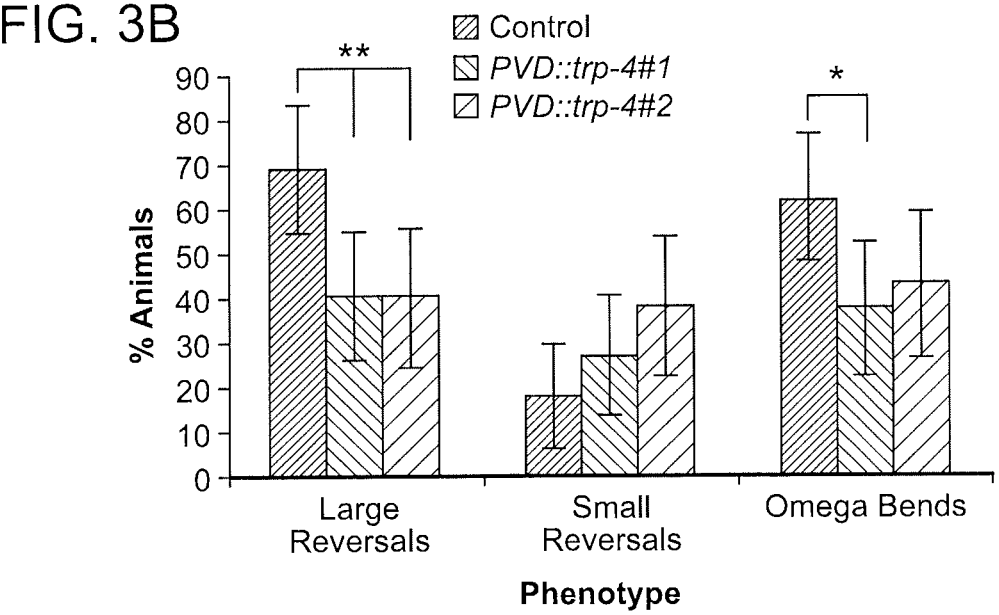
Figure 3C:
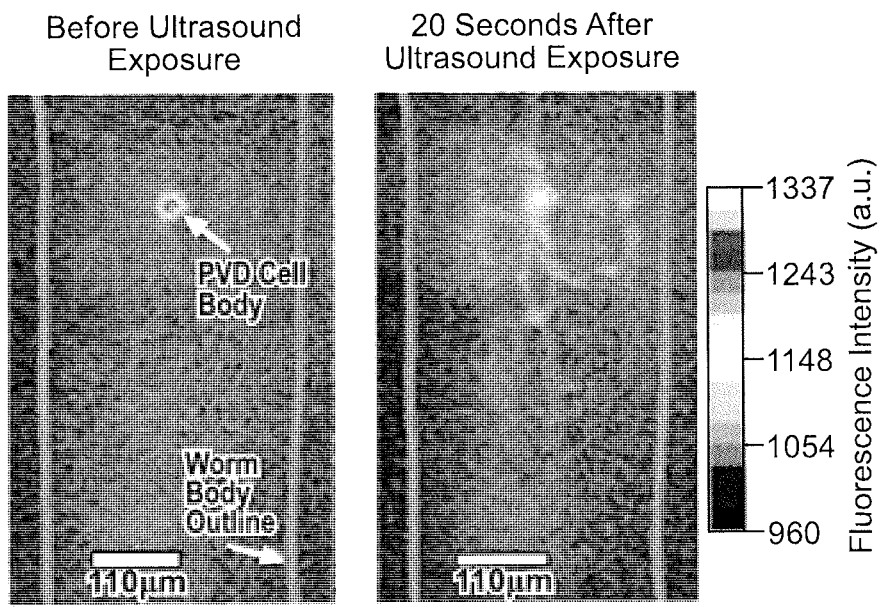
Figure 3D:
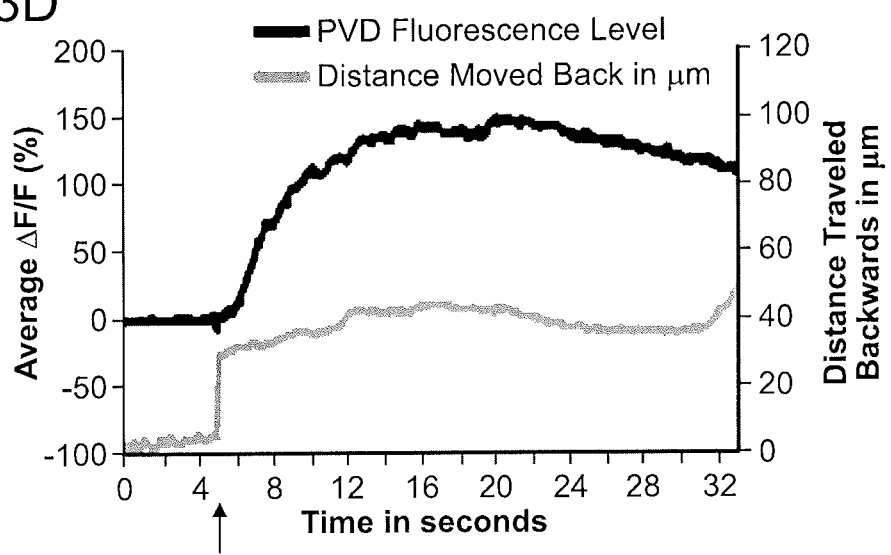
Figure 7A:
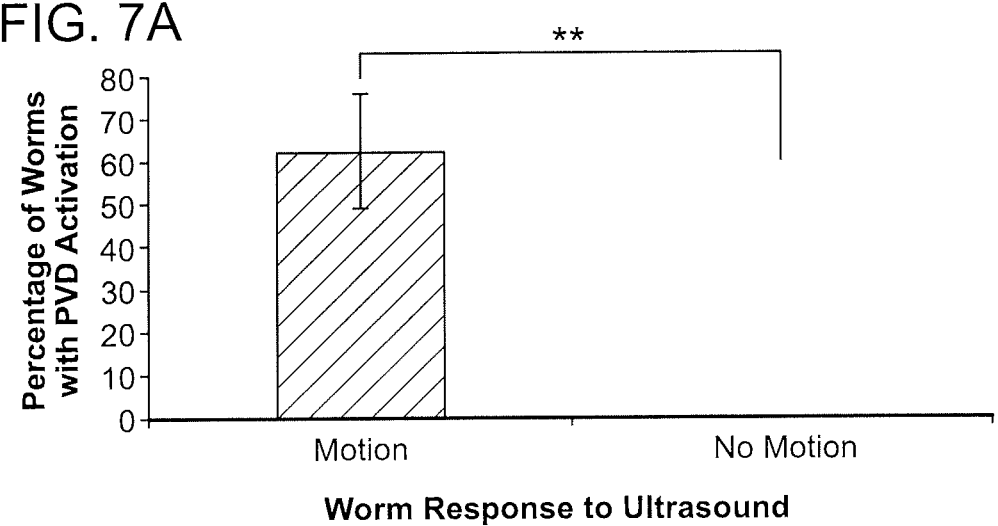
FIG. 7A, FIG. 7B, and FIG. 7C: PVD activity depends on worm movement. PVD activity is strongly correlated with movement (n=89) as shown in FIG. 7A, in the backward direction (Backward n=25, forward n=16) as shown in FIG. 7B and when animals stop or slow down (stop or slow down n=22, not stopping or slowing down n=19) as shown in FIG. 7C. Averages and s.e.m are shown with ** indicating p<0.001 by Fisher' exact t-test.
Figure 7B:
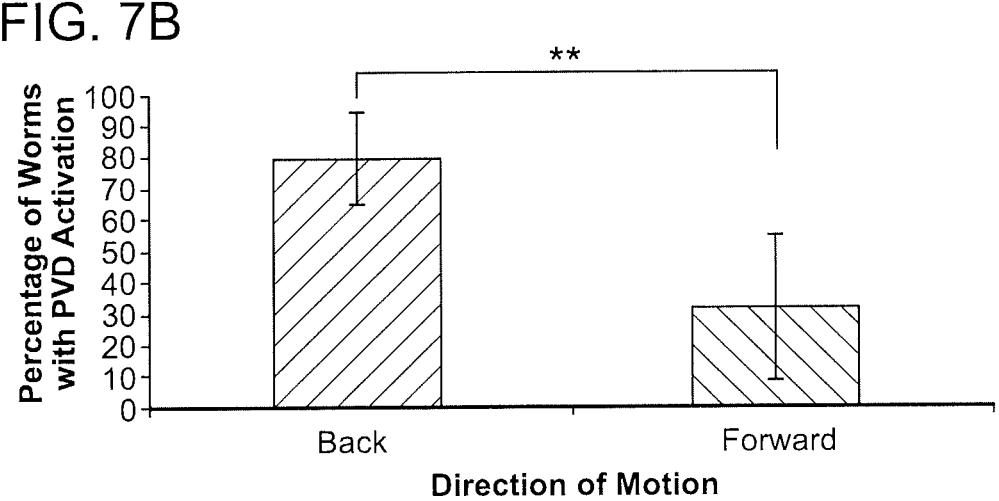
Figure 7C:
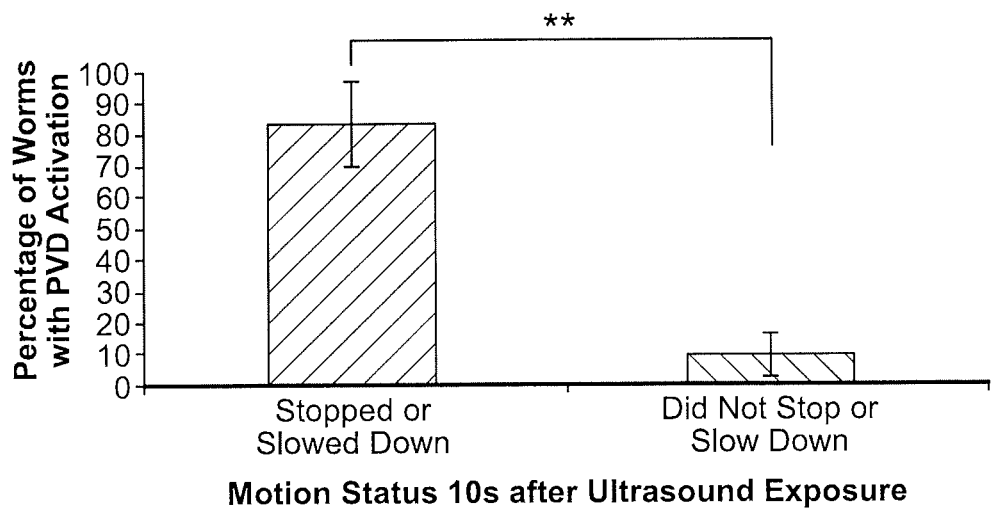

Example 4: Newly Identified Roles for PVD Sensory and AIY Interneurons in Generating Behavior in the Presence of Microbubbles To test Applicants' approach of analyzing neuronal function by misexpressing TRP-4, Applicants probed the functions of poorly understood PVD neurons (FIG. 3A). PVD neurons have extensive dendritic processes that are regularly spaced and non-overlapping and cover most of the animal, excluding the head and the neck (A. Albeg, C. J. Smith, M. Chatzigeorgiou et al., Mol Cell Neurosci 46 (1), 308 (2011)). Applicants find that expressing TRP-4 in PVD neurons leads to a significant decrease in their reversal responses upon ultrasound stimulation (FIG. 3B). Applicants hypothesize that PVD neurons suppress reversals and misexpressing TRP-4 channels activates these neurons upon ultrasound stimulation, which in turn suppresses reversals. To test Applicants' hypothesis Applicants monitored PVD neuron activity in response to ultrasound stimulation. Applicants find that PVD neurons are more likely to be activated when the animal is moving backward than when moving forward (FIGS. 7A-7C). Also, Applicants find a strong correlation between PVD activity and animal movement. In particular, Applicants find that PVD neurons reach their maximum response when the animal has stopped reversing (FIGS. 3C and 3D). These results suggest that expressing TRP-4 in PVD neurons activates them upon ultrasound stimulation and causes premature suppression of backward movement leading to fewer reversals. See also FIG. 17.

Figure 3E:
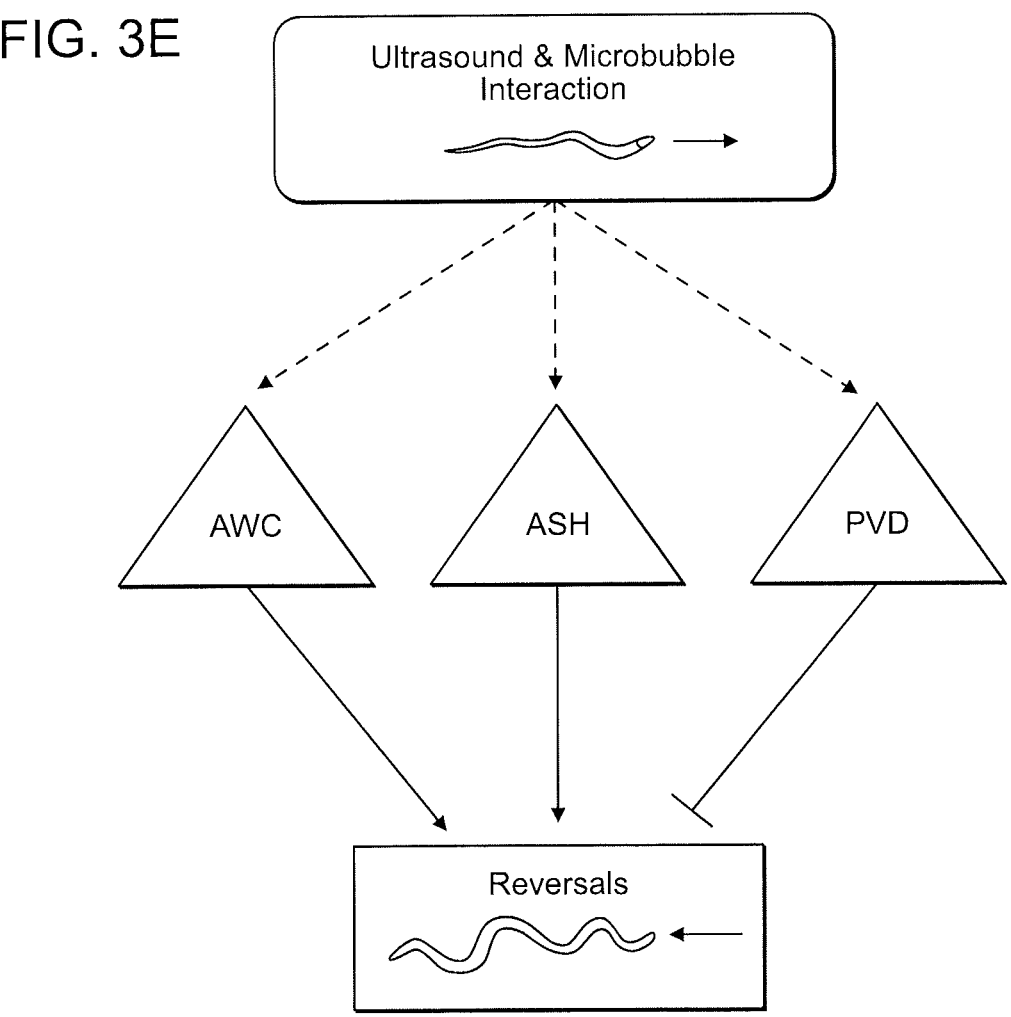
Figure 3F:
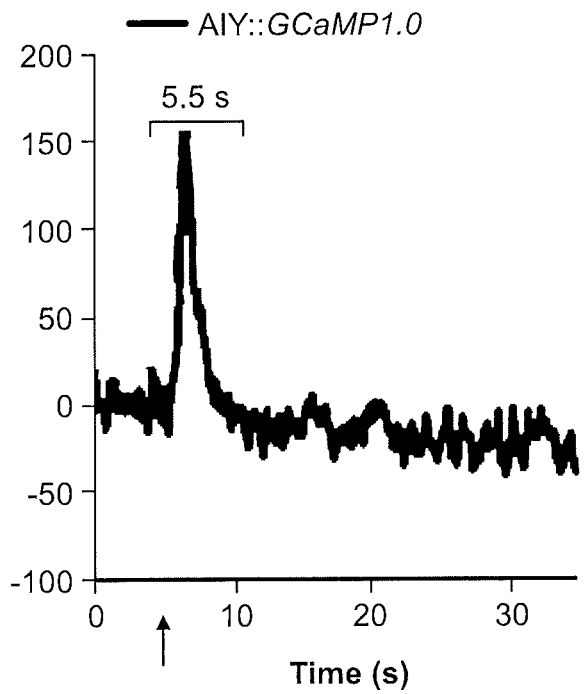
Figure 3F:
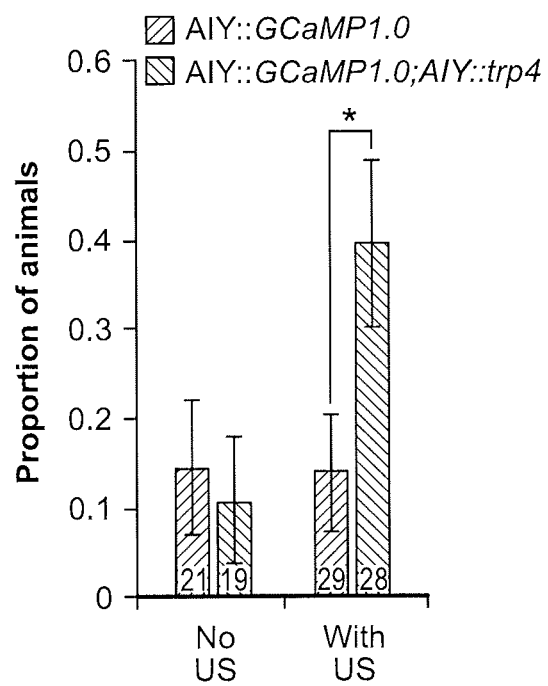

Applicants' studies show that C. elegans neural circuits can be probed by combining ultrasound stimulation with microbubbles that amplify the mechanical deformations. Specifically, Applicants find that upon activation ASH and AWC sensory neurons increase in reversals, while activating PVD neurons suppresses reversals (FIG. 3E). Interestingly, Applicants identify that persistent AWC neural activity might be required to drive reversal behavior providing a correlation between a distinct AWC neuronal activity pattern and whole animal behavior. Also, Applicants define a novel role for PVD neurons in suppressing reversal behavior. Taken together, these results and other studies (D. Tobin, D. Madsen, A. Kahn-Kirby et al., Neuron 35 (2), 307 (2002)) show that TRP channels can be used to manipulate neuronal functions and thus provide insight into how neural circuits transform environmental changes into behavior.

Figure 18A:
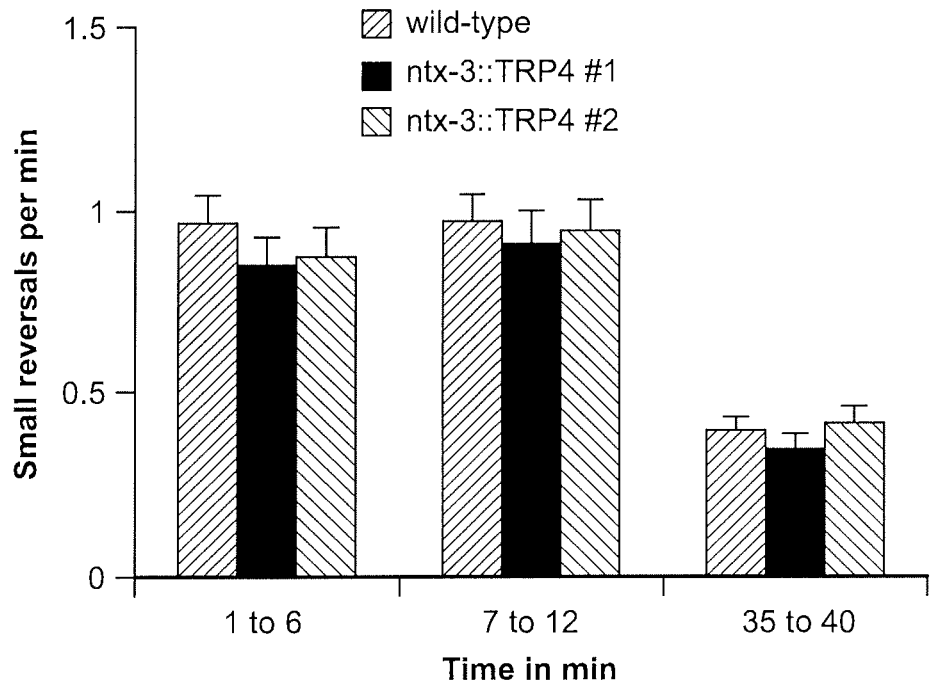
FIG. 18A, FIG. 18B, and FIG. 18C show that AIY transgenic worms have normal local search. Animals were moved from food to a food-free plate and their reversals and omega bends were quantified. The two AIY::trp-4 transgenics executed normal number of small reversals as shown in FIG. 18A, large reversals as shown in FIG. 18B and omega bends as shown in FIG. 18C.
Figure 18B:
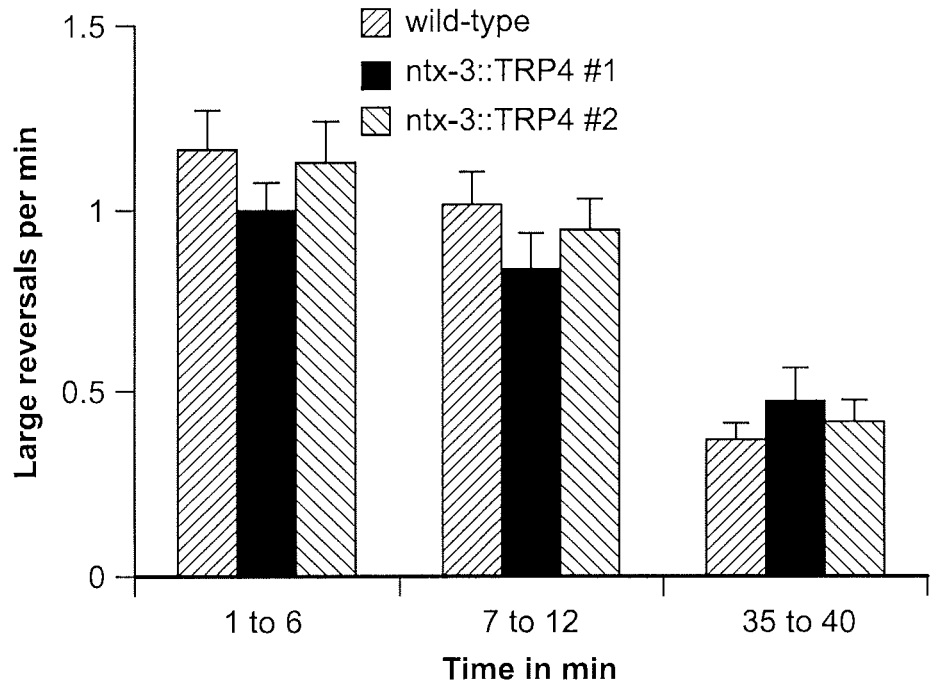
Figure 18C:
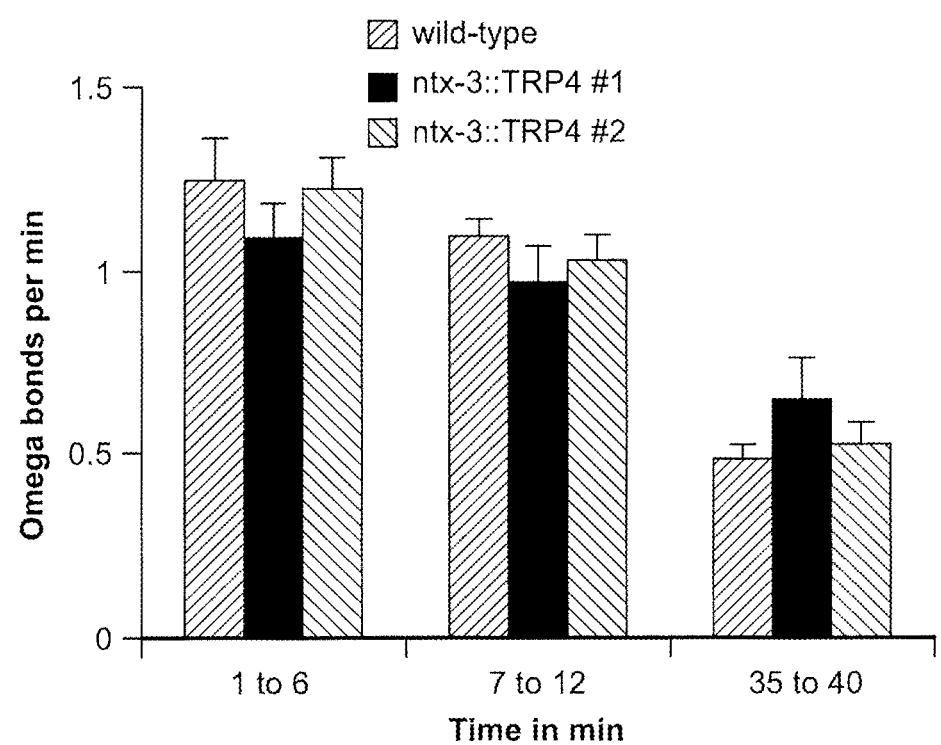

Applicants then tested whether this approach can manipulate the function of an interneuron, whose processes do not contact the external cuticle of the animal. Applicants misexpressed TRP-4 in AIY interneurons, which are at least 25 µm from the cuticle, and analyzed the behavior of these animals upon ultrasound stimulation. Optogenetic studies have previously shown that activating AIY interneurons reduces turns. In contrast, Applicants find that AIY::trp-4 transgenics are significantly more likely to initiate high-angled omega bends upon ultrasound stimulation (two independent transgenics). It is possible that expressing TRP-4 in AIY neurons has altered that neuron's function, leading to increased turns. However, animals with genetically altered AIY function have been shown to have increased turns in a local search assay. Applicants found that these AIY::trp-4 transgenics did not show any defects in local search (FIG. 18) confirming that the AIY neurons were not altered in these animals. These data suggest that AIY can initiate different behaviors based on type of stimulation, ultrasound or light.

Figure 11A:
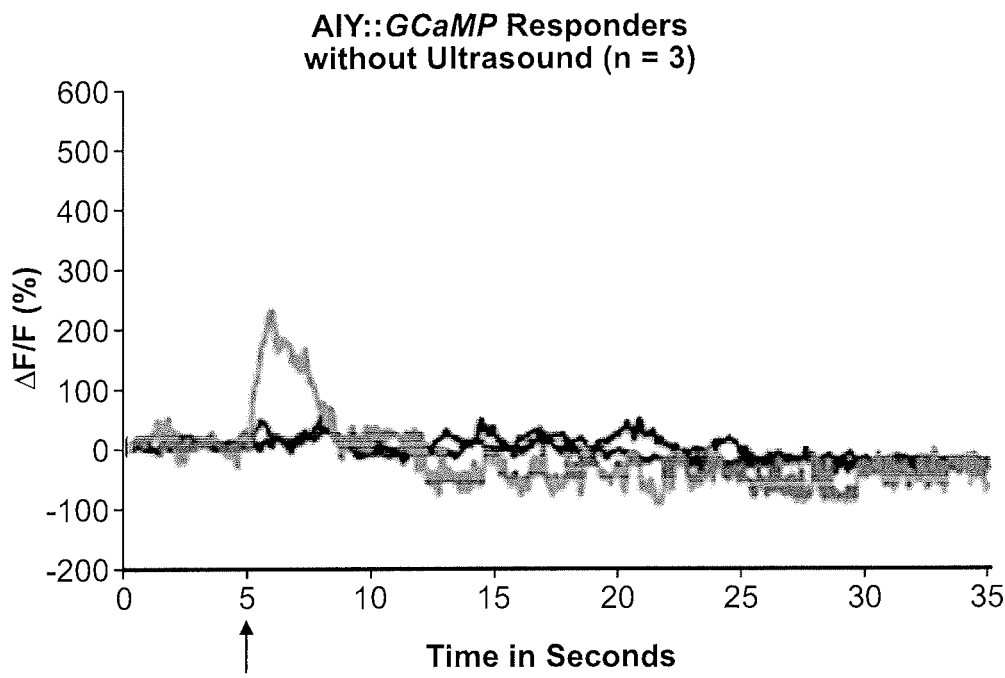
FIGS. 11A-11H showing AIY responses to ultrasound in FIGS. 11A-11D. Ratio of change in fluorescence in the AIY neurite without as shown in FIGS. 11A and 11B and with ultrasound as shown in FIGS. 11C and 11D. Neurons that responded in a 5.5 second window around t=5 seconds are shown in FIGS. 11A and 11C and those that did not are shown in FIGS. 11B and 11D. Ultrasound stimulus was presented at t=5 seconds in FIGS. 11C and 11D.
Figure 11B:
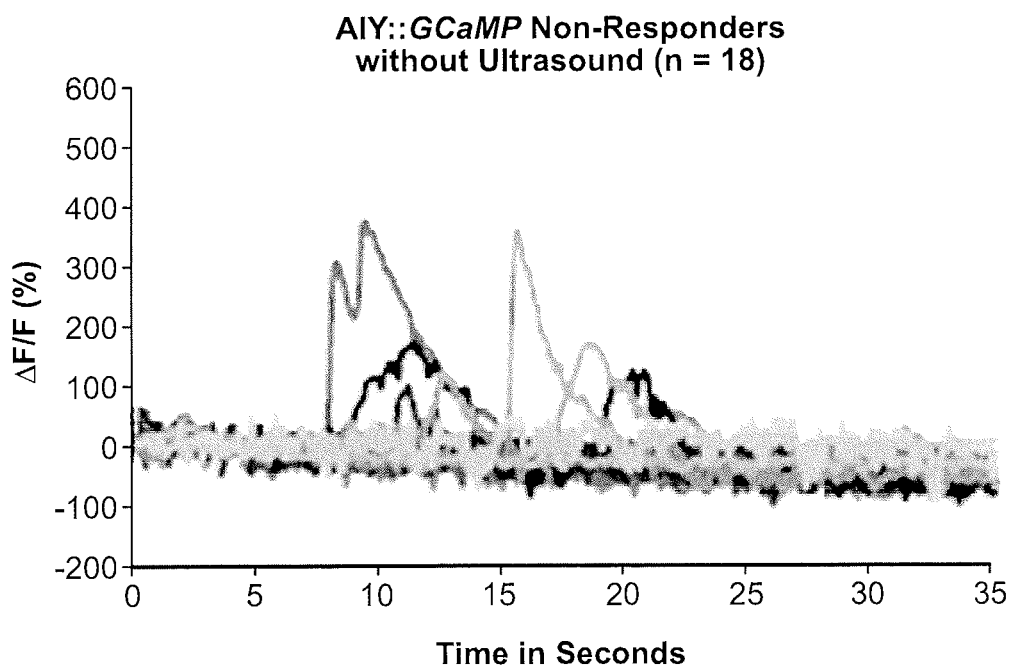
Figure 11C:
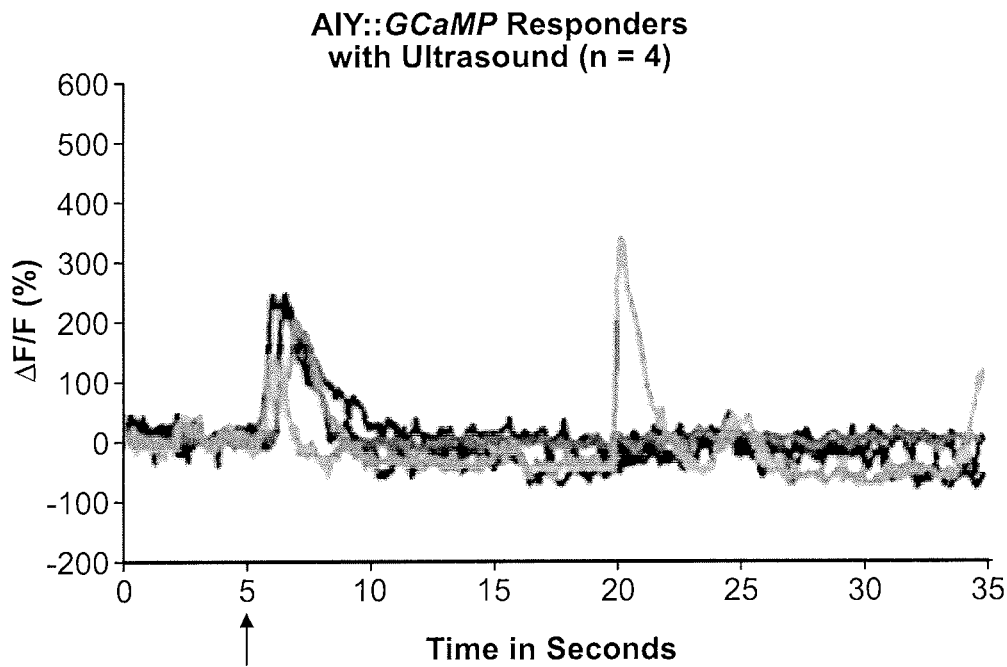
Figure 11D:
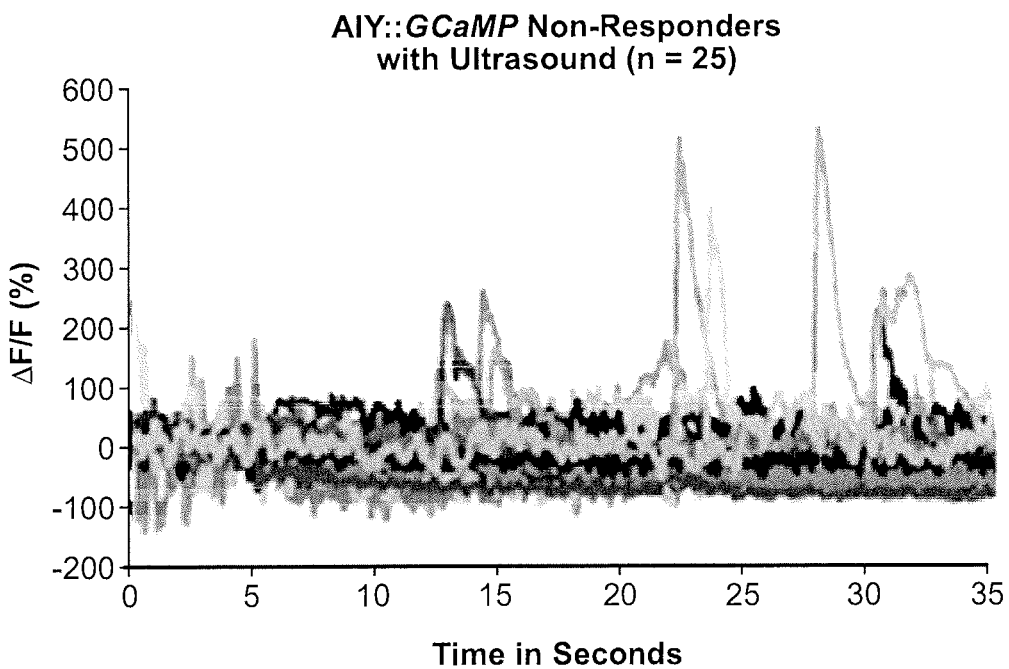
Figure 11E:
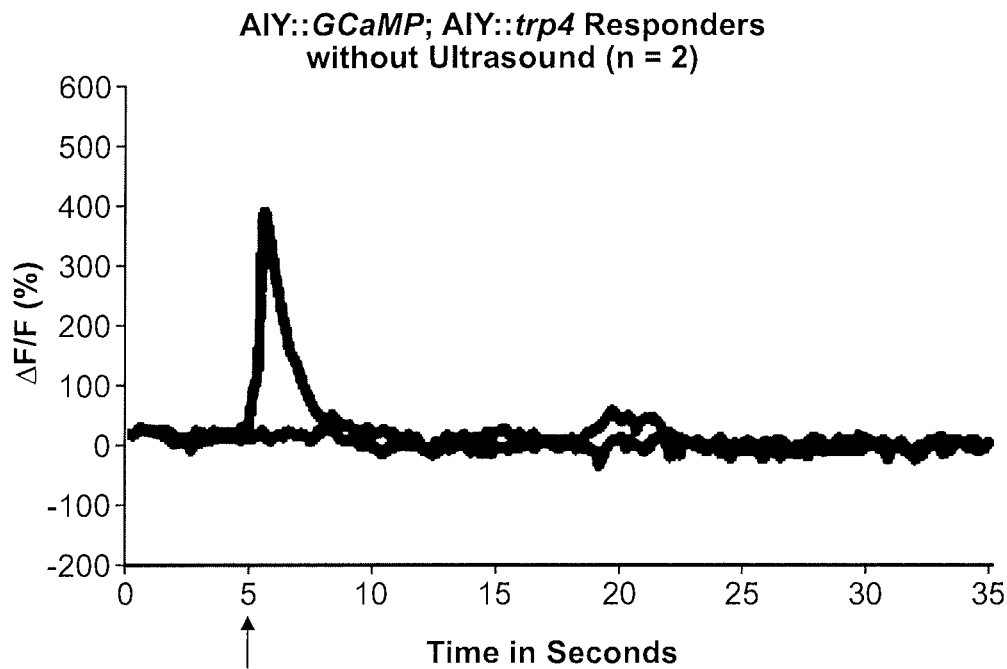
Figure 11F:
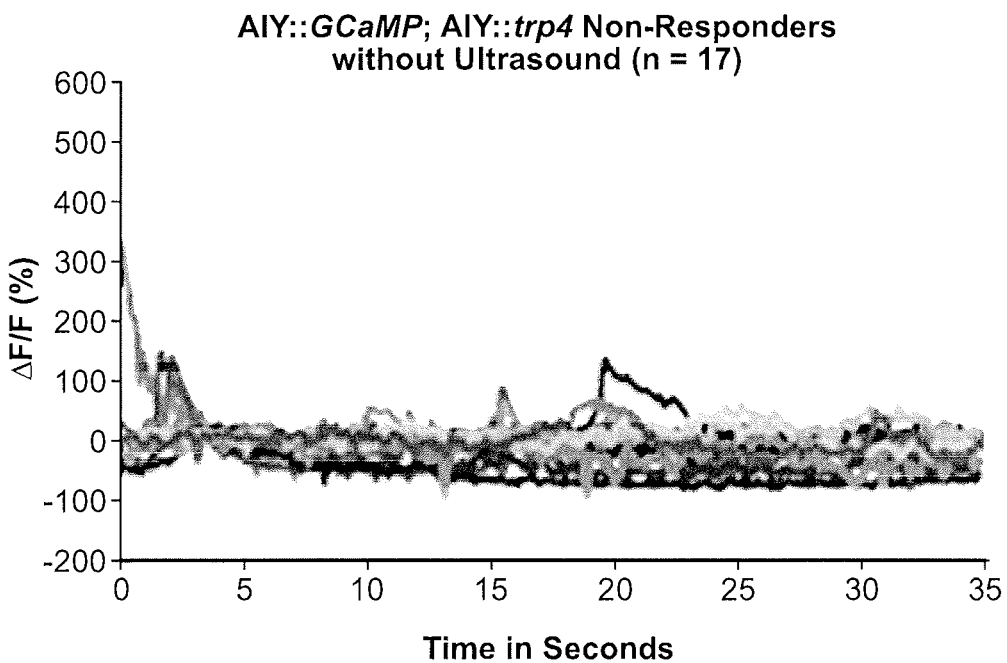
Figure 11G:
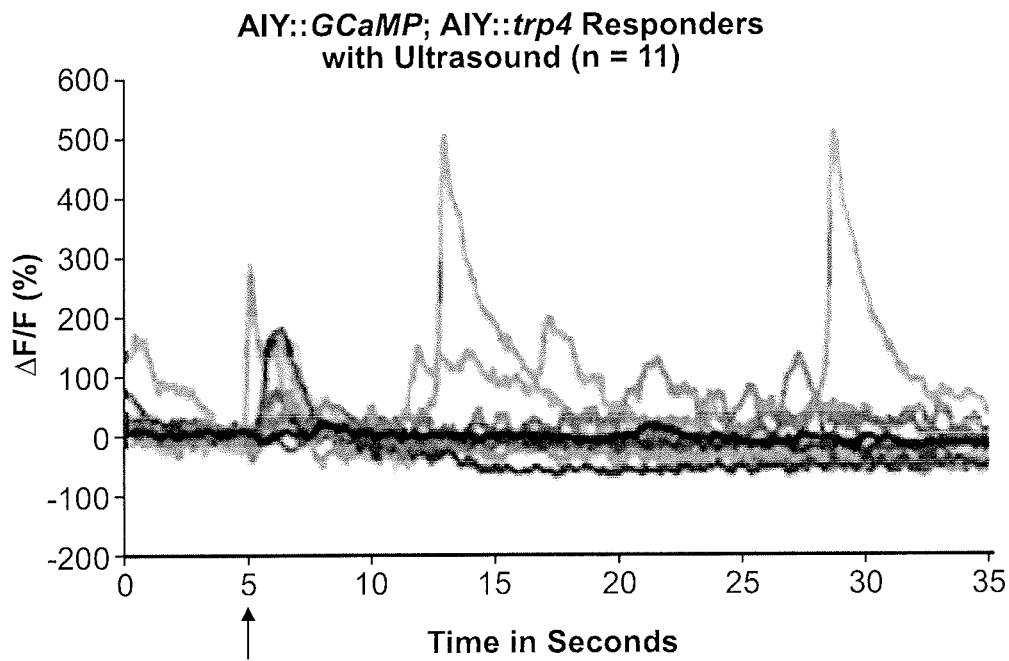
Figure 11H:
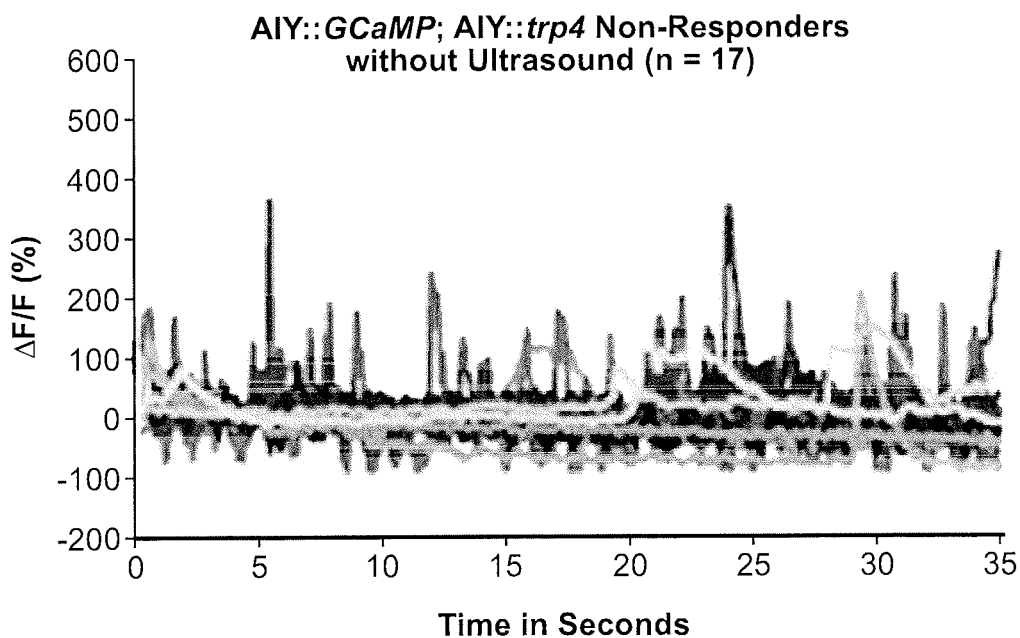

To confirm whether ultrasound stimulus is activating AIY interneurons, we used calcium imaging. AIY neural activity is typically measured from a bulb in the AIY neurite. Consistent with previous observation, Applicants found that AIY is a noisy neuron with a number of transients during recordings (FIG. 11). Applicants collected from a number of AIY recordings from wild-type animals and defined the relevant transient. Applicants counted all neurons that responded within a 5.5 second after the ultrasound pulse as responders. Using this criteria, AIY neurons in wild-type animals did not show a significant response to ultrasound stimulus (4/29) (FIGS. 11A and 11B). In contrast, Applicants observed a significant number of AIY neurons in AIY::trp-4 transgenics (11/28 animals) had a positive response (FIGS. 11E and 11F). In contrast, Applicants suggest that increased proportion of AIY responders in the AIY::trp-4 transgenics suggests that ultrasound stimulus activates AIY interneurons. These results show that mechanical deformations from the ultrasound-microbubble interaction can penetrate at least 25 µm into the worm and influence the function of AIY interneurons. Moreover, Applicants find that misexpressing TRP-4 can influence both reversal and omega bend neural circuitry, suggesting that the sonogenetic approach is broadly applicable for manipulating circuit activity. Further, these results show that AIY interneurons likely have at least three activity states with one suppressing turns, one promoting forward turns (as revealed by optogenetic stimulation) and one increasing omega turns (as revealed by ultrasound stimulation). These studies validate the approach of using sonogenetics to reveal novel roles for both PVD and AIY neurons in modifying turn behavior.

These studies show that C. elegans neural circuits can be probed by combining low-pressure ultrasound stimulation with microbubbles that amplify the mechanical deformations. Specifically, Applicants found that C. elegans are insensitive to low-pressure ultrasound but respond when surrounded by microbubbles. Applicants found that animals missing the TRP-4 mechanosensitive ion channel have significantly reduced sensitivity to the ultrasound-microbubble stimulation, indicating that mechanosensitive ion channels play an important role in the mechanism of ultrasound stimulation. Applicants also found that misexpressing the TRP-4 mechanosensitive ion channel in specific neurons modifies their neural activity upon ultrasound stimulation, resulting in altered animal behaviors. Specifically, misexpressing TRP-4 in ASH and AWC sensory neurons results in an increase in large reversals, while activating PVD neurons suppresses this behavior. Applicants also defined novel roles for PVD neurons in suppressing reversal behavior and AIY neurons in stimulating omega bend behavior.

These novel methods provide new insights into the neural activity patterns that drive whole-animal behavior. Persistent AWC neural activity might drive reversal behavior, providing a correlation between a distinct AWC neuronal activity pattern and whole-animal behavior. Ultrasound stimulation may activate neurons with different kinetics than what has been seen using optogenetics. For example, activating AIY interneurons using light leads to an increase in forward turns, while using low-pressure ultrasound increases omega bend frequency. These studies indicate an alternative role for AIY in promoting omega bends. The stimulation of AIY interneurons demonstrates that this ultrasound technique can also be applied to deep internal neurons that do not contact the skin of the worm. Taken together, these results and other studies show that TRP channels can be used to manipulate neuronal functions and thus provide insight into how neural circuits transform environmental changes into precise behaviors.

In order to target smaller groups of neurons, the resolution of the ultrasound focal zone can be made smaller than the 1 mm diameter. Frequencies above 2.25 MHz can produce sub-millimeter focal zone spot sizes. Higher frequency ultrasound waves with their smaller focal zones are better suited to targets that are closer to the body surface as these waves do not penetrate tissues as well. One of the advantages of ultrasound is that small focal zones can be maintained noninvasively even in deep brain tissue. Outside the focal zone the peak negative pressures are significantly lower and are unlikely to result in neuron activation. This was seen on the agar plates where only worms that were in the focal zone responded to the ultrasound and nearby worms that were outside the focal zone did not. Another advantage of ultrasound is that this focal zone can be moved arbitrarily within the tissue to simulate different regions without any invasive procedures. With an electronically steerable ultrasound beam, multiple different targets can be noninvasively manipulated either simultaneously or in rapid successio. Moreover, the genetic targeting of the stretch sensitive ion channels to individual neurons allows for targeting well below the resolution of the ultrasound focal zone.

The use of ultrasound as a non-invasive neuronal activator can be broadly applied to decode neural circuits in larger vertebrate brains with opaque skin and intact skulls. Ultrasound waves with peak negative pressures of <1 MPa have been shown to penetrate through skull and brain tissue with very little impedance or tissue damage. These results show that low-pressure ultrasound (with peak negative pressures 0.4-0.6 MPa) specifically activates neurons expressing the TRP-4 channel. Moreover, TRP-4 channels do not have mammalian homologs, therefore, it is unlikely that expressing these channels in the mammalian brain would produce deleterious effects. This suggests that neurons in diverse model organisms misexpressing this channel can be activated by ultrasound stimulation, allowing scientists to probe their functions in influencing animal behavior. Additionally, other mechanosensitive channels can be explored that may be more sensitive to mechanic deformations than TRP-4. Of particular interest are the bacterial MscL and MscS channels that have different sensitivities to membrane stretch and are selective for different ions. Moreover, TRP-4 and other channels may be mutated in and around the pore region in order to change their ion selectivity as well as their sensitivity to mechanical stretch to broaden the utility of this method.

Furthermore, if low-pressure ultrasound stimulation by itself does not activate TRP-4 expressing neurons, the mechanical signals can be amplified by gas-filled microbubbles. Perfluorohexane microbubbles are well-established for use as ultrasound contrast agents in vivo and can be administered intravenously to circulate throughout the vertebrate body including the brain. They can remain active for up to 60 minutes providing a time window where they could be used safely to amplify the ultrasound stimulus and manipulate neural activity. Microbubbles have been shown to undergo inertial cavitation when exposed to ultrasound with peak negative pressure of 0.58 MPa and higher. Using ultrasound pressure levels lower than this will prevent damage to the brain from the microbubble-ultrasound interaction. Moreover, Applicants used a third of the number of microbubbles that has been previously used to successfully image the mouse brain showing that the required microbubble dose would not be prohibitive for in vivo administration. These experiments show that in the presence of microbubbles the low pressure ultrasound stimulated the deep MY interneurons expressing TRP-4. This result enables Applicants to estimate the distances at which the mechanical deformations from the ultrasound-microbubble interaction can effectively penetrate into brain tissue from the vasculature. The C. elegans cuticle is 0.5 µm thick and the AIY interneurons are 25 µm from the cuticle, indicating that the mechanical deformations traveled at least 25.5 µm into the worm. In contrast, the mammalian blood-brain barrier is 0.2 µm thick and the average distance of a neuron from a capillary is less than 20 µm. These distances are well within the range of the sonogenetic approach. With the data presented in this paper, the invention provides a novel, non-invasive approach to activate genetically targeted neurons using low-pressure ultrasound stimulation The results described herein above were carried out using the following materials and methods.

Behavioral Assay

Figure 9:
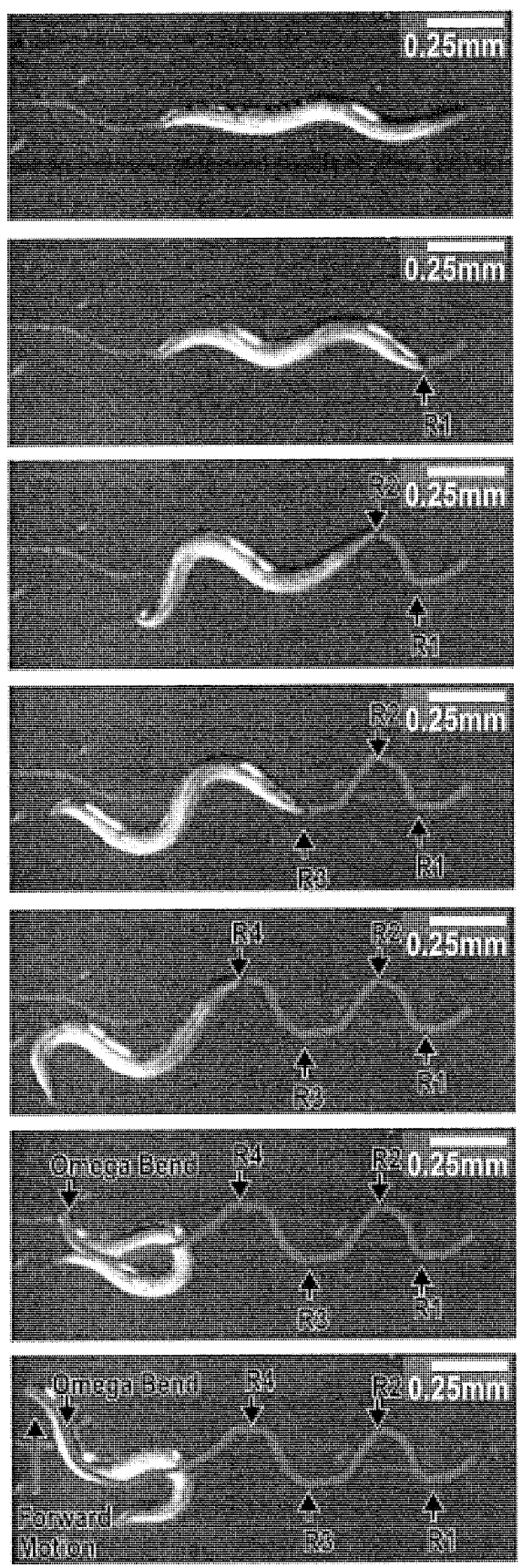
FIG. 9: Behavioral responses to ultrasound.

Well-fed young adults were placed on an empty NGM agar plate and corralled into a small area using a filter paper soaked in copper solution (200 mM). A solution (15 µl) of microbubbles at a density of $3.8 \times 10^7$/ml was added to the plate with worms. The worms were allowed to crawl around for 10 minutes before being stimulated by ultrasound. An animal was moved into the fixed ultrasound focal zone and stimulated with one pulse and the resulting reversal and omega bend response is recorded. Reversals with fewer than two head bends were identified as small, while those with more than two were counted as large. High-angled turns that lead to a significant change in the direction of an animal's movement were identified as omega bends (FIG. 9) (J. M. Gray, J. J. Hill, and C. I. Bargmann, Proc Natl Acad Sci USA 102 (9), 3184 (2005)). Data was analyzed using SPSS software v22 (IBM, NY).

Imaging

Transgenic animals expressing GCaMP in specific neurons were corralled into a small area by filter paper soaked in copper solution (as described above). The acetylcholine agonist and paralytic, tetramisole (J. A. Lewis, C. H. Wu, J. H. Levine et al., Neuroscience 5 (6), 967 (1980)), was used at 1.3 mM to paralyze the animals to facilitate recording neural activity. These animals were surrounded by a solution of microbubbles and stimulated using ultrasound intensities as described. Fluorescence was recorded at 10 frames/second using an EMCCD camera (Photometrics, Quant-EM) and resulting movies were analyzed using Metamorph software (Molecular Devices) as described (S. H. Chalasani, N. Chronis, M. Tsunozaki et al., Nature 450 (7166), 63 (2007)). Briefly, a fluorescence baseline was calculated using a 3-second window from t=1 to t=4 seconds. The ratio of change in fluorescence to baseline fluorescence was plotted in all graphs using custom MATLAB scripts (S. H. Chalasani, N. Chronis, M. Tsunozaki et al., Nature 450 (7166), 63 (2007)). For imaging PVD neurons, the concentration of the paralytic was reduced to 1 mM, which allowed these animals greater movement. Their motion along with the corresponding fluorescent intensity changes was captured and analyzed using Metamorph software.

Microbubble Synthesis

Figure 10A:
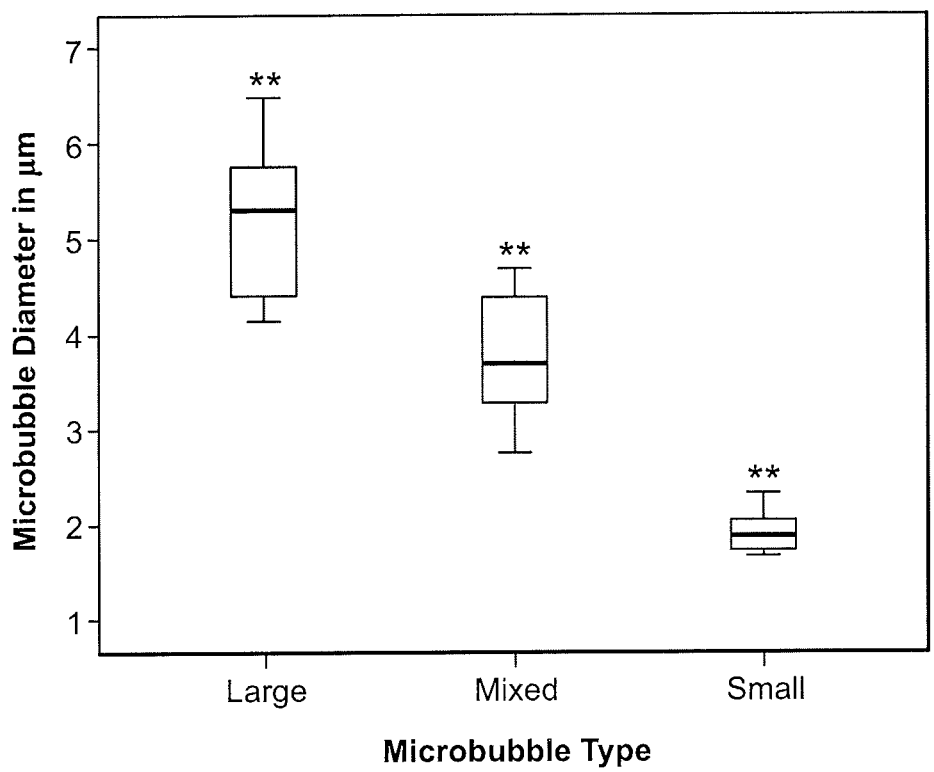
FIG. 10A, FIG. 10B, FIG. 10C, and FIG. 10D: Microbubbles transduce ultrasound stimuli.
Figure 10B:
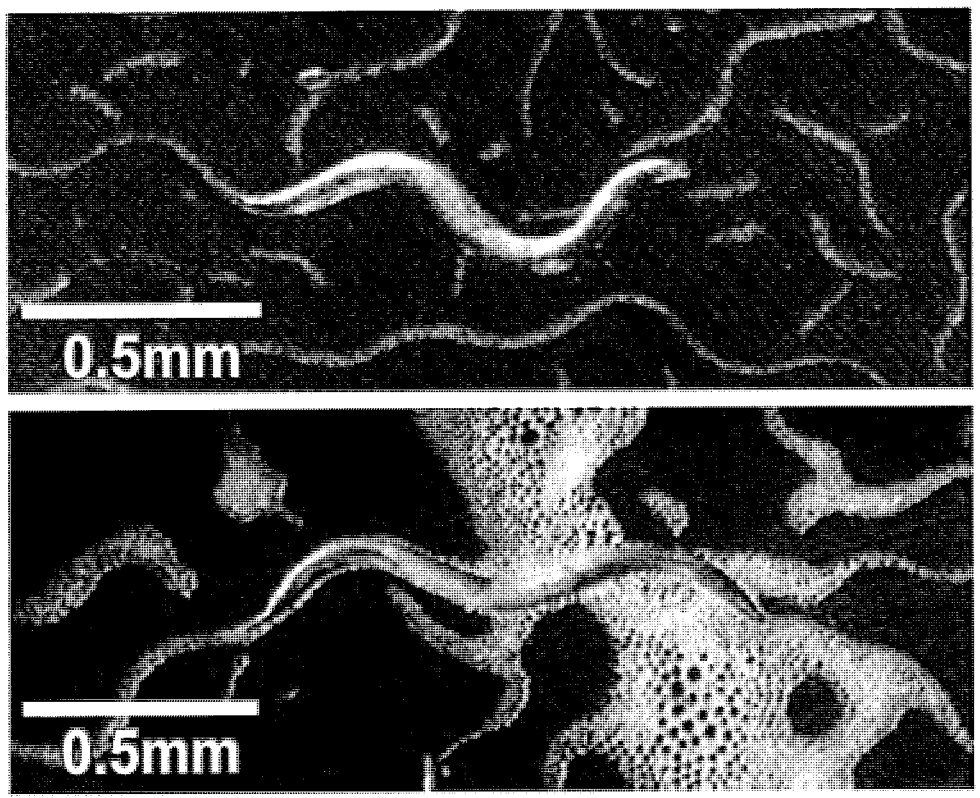
Figure 10C:
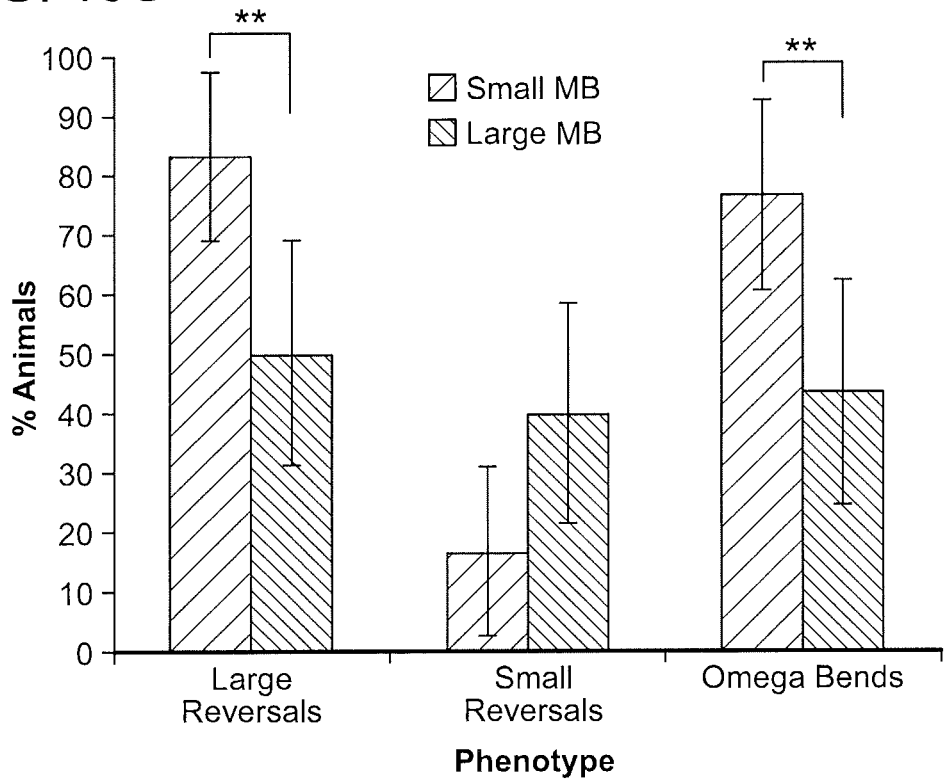
Figure 10D:
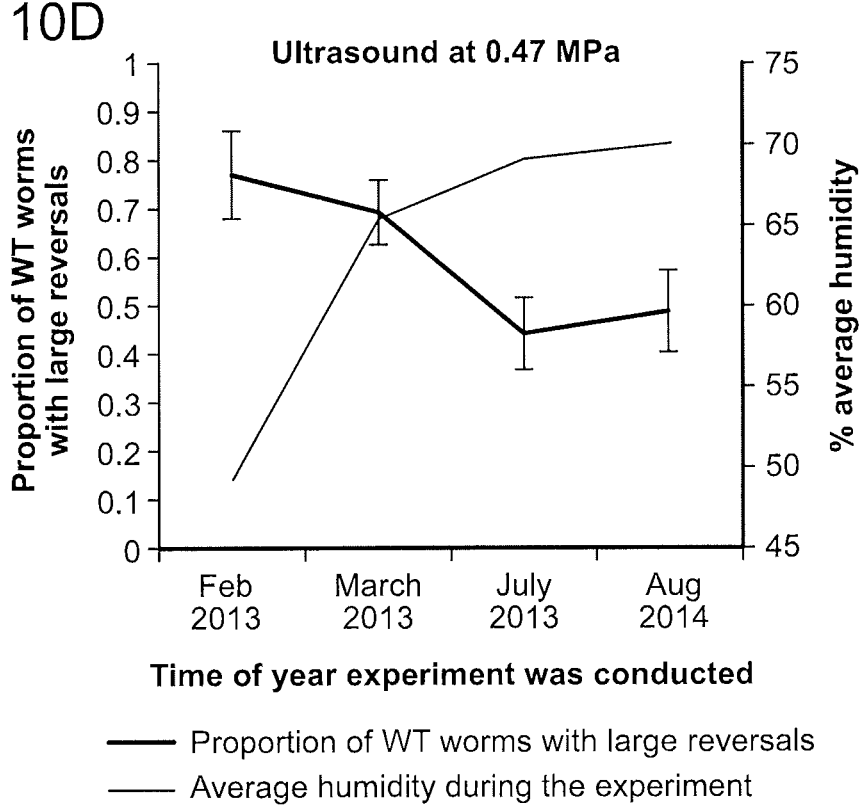

Microbubbles were made using a probe sonication technique as described (C. E. Schutt, S. D. Ibsen, M. J. Benchimol et al., Small (2014)). The stabilizing lipid monolayer consisted of distearoyl phosphatidylcholine (DSPC, Avanti Polar Lipids Inc., Alabaster, Ala.), distearoyl phosphatidylethanolamine-methyl polyethylene glycol (mPEG-DSPE 5k, Layson Bio Inc., Arab, Ala.) and DiO (Biotium Inc., CA) in 85:13:2 molar ratio. The gas core of the microbubble consisted of perfluorohexane (Sigma-Aldrich, St. Louis, Mo.) and air mixture designed to attain stability under atmospheric pressure. Microbubbles were fractionated based on size by their settling time (FIGS. 10A-10C). Applicants chose a mixed size of microbubbles to maintain uniformity across all the experiments. The microbubbles were shown to be stable on agar plates sealed with parafilm for up to 24 hours.

Molecular Biology and Transgenic Animals

All C. elegans strains were grown under standard conditions as described (S. Brenner, Genetics 77 (1), 71 (1974)). Cell-selective expression of TRP-4 was achieved by driving the full-length cDNA under odr-3 (AWC), sra-6 (ASH) and des-2 (PVD and FLP) promoters. Germline transformations were obtained using the methods previously described (C. C. Mello, J. M. Kramer, D. Stinchcomb et al., Embo J 10 (12), 3959 (1991)). Complete information for all strains is listed in Table 1.

Temperature Estimation

Ultrasound stimulation in combination with microbubbles has been previously shown to cause temperature changes in the surrounding media (D. Razansky, P. D. Einziger, and D. R. Adam, IEEE Trans Ultrason Ferroelectr Freq Control 53 (1), 137 (2006)). The authors experimentally found a temperature increase of 14.11° C./sec using a continuous 1.1 MHz ultrasound pulse with a peak negative pressure of 2.8 MPa (D. Razansky, P. D. Einziger, and D. R. Adam, IEEE Trans Ultrason Ferroelectr Freq Control 53 (1), 137 (2006)). In Applicants' assays, Applicants used pulses of 10 ms and a maximum peak ultrasound pressure at 0.8 MPa. Applicants assumed a linear relationship between energy deposition and peak ultrasound pressure and calculated the temperature increase around the worms on the agar surface to be 0.04° C.

Ultrasound and Microscopy Setup

A schematic of the ultrasound and microscopy setup is shown in FIG. 1A and previously described (S. Ibsen, M.

Benchimol, and S. Esener, *Ultrasonics* 53 (1), 178 (2013)). 10 ms, 2.25 MHz sine wave ultrasound pulse was generated with a submersible 2.25 MHz transducer (V305-Su, Panametrics, Waltham, Mass.) using a waterproof connector cable (BCU-58-6W, Panametrics, Waltham, Mass.). The resulting sound field was quantified using a needle hydrophone (HNP-0400, Onda Corporation, Sunnyvale, Calif.). An arbitrary waveform generator (PCI5412, National Instruments, Austin, Tex.) controlled by a custom designed program (LabVIEW 8.2, National Instruments, Austin, Tex.) was used to create the desired ultrasound pulse. The peak negative pressure of the ultrasound pulse was adjusted from 0 to 0.9 MPa using a 300 W amplifier (VTC2057574, Vox Technologies, Richardson, Tex.). Ultrasound attenuation though the plastic and agar was found to be minimal.

White light illumination was achieved by reflecting light from an external light source up at the petri dish using a mirror mounted at 45°. Behavior was captured using a high-speed camera (FASTCAM, Photron, San Diego, Calif.). Fluorescent images were collected using a Nikon 1-FL EPI-fluorescence attachment on the same setup as described. GCaMP imaging was performed using a 40× objective and the images were captured using a Quanti-EM 512C camera (Photometrics, Tucson, Ariz.).

The petri dish was held at the air-water interface with a three-prong clamp mounted to an XYZ micromanipulator stage allowing the dish to be scanned in the XY plane, while maintaining a constant Z distance between the objective and ultrasound transducer. This alignment positioned the agar surface in the focal zone of the ultrasound wave.

TABLE 1

Table showing list of all strains and their genotypes

| Strain | Genotype | Description |
| --- | --- | --- |
| N2 | wild-type | WT |
| VC1141 | trp-4(ok1605) | trp-4 mutant |
| IV133 | ueEx71 [sra-6::trp-4, elt-2::gfp] | ASH expression of trp-4 in wildtype background |
| IV157 | ueEx85 [odr-3::trp-4, elt-2::gfp] | AWC expression of trp-4 in wildtype background |
| CX10536 | kyEx2595 [str-2::GCaMP2.2b, unc-122::gfp] | AWC imaging line in wildtype background |
| IV344 | ueEx219 [odr-3::trp-4, unc-122::rfp], kyEx2595 [str-2::GCaMP2.2b, unc-122::gfp] | AWC imaging line with trp-4 expressed in AWC |
| IV242 | ueEx150 [des-2::trp-4; elt-2::gfp #3] | PVD expression of trp-4 in wildtype background |
| IV243 | ueEx151 [des-2::trp-4; elt-2::gfp #4] | PVD expression of trp-4 in wildtype background |
| IV219 | ueEx134 [des-2::GCaMP3, unc-122::rfp] | PVD and FLP imaging line in wildtype background |
| IV494 | ueEx307 [ttx-3::trp-4; elt-2::gfp #3] | AIY expression of trp-4 in wildtype background |
| IV495 | ueEx308 [ttx-3::trp-4; elt-2::gfp #4] | AIY expression of trp-4 in wildtype background |
| CX8554 | kyEx1489 [ttx-3::GCaMP1.0, unc-122::gfp] | AIY imaging line in wildtype background |
| IV646 | kyEx1489[ttx-3::GCaMP1.0, unc-122::gfp]; ueEx440[ttx-3::trp-4, unc-122::rfp] | AIY imaging line with trp-4 expressed in AIY |

What is claimed is:

1. A method of rendering a cell responsive to mechanical deformation or stretch caused by ultrasound, the method comprising:
   transducing a cell to express an exogenous, non-mammalian TRP-4 polypeptide,
   contacting the cell with ultrasound; and
   inducing cation influx in the TRP-4-expressing cell and an alteration in cell activity and/or function following said contact with ultrasound, thereby rendering the cell responsive to mechanical deformation or stretch caused by ultrasound.

2. The method of claim 1, wherein said TRP-4 polypeptide comprises the amino acid sequence of SEQ ID NO: 1.

3. The method of claim 1, wherein the cell is transduced using a vector comprising a polynucleotide sequence encoding the exogenous, non-mammalian TRP-4 polypeptide or using a recombinant nucleic acid molecule encoding the exogenous, non-mammalian TRP-4 polypeptide.

4. A method of inducing cation influx in a cell and sensitizing the cell to mechanical deformation or stretch caused by ultrasound, the method comprising:
   transducing a cell to express an exogenous, non-mammalian mechanotransduction TRP-4 polypeptide;
   applying ultrasound to the cell; and
   inducing cation influx in the TRP-4-expressing cell and an alteration in cell activity and/or function following said application of ultrasound, thereby sensitizing the cell to said mechanical deformation or stretch caused by ultrasound.

5. The method of claim 4, wherein said cell is a mammalian cell.

6. The method of claim 4, wherein said cell is a bacterial cell.

7. The method of claim 4, wherein said TRP-4 polypeptide is encoded by a polynucleotide codon-optimized for expression in the cell.

8. The method of claim 4, wherein the cell is a muscle cell, a cardiac muscle cell, a neuron, a motor neuron, a sensory neuron, an interneuron, or an insulin secreting cell.

9. The method of claim 4, wherein said ultrasound has a frequency of about 0.8 MHz to about 4 MHz.

10. The method of claim 4, wherein said ultrasound has a focal zone of about 1 cubic millimeter to about 1 cubic centimeter.

11. The method of claim 4, said method further comprising contacting the cell with a microbubble prior to applying ultrasound.

12. The method of claim 4, wherein said cell is in vitro or in vivo.

13. The method of claim 4, wherein the cell is transduced using a vector comprising a polynucleotide sequence encoding the exogenous, non-mammalian TRP-4 polypeptide or using a recombinant nucleic acid molecule encoding the exogenous, non-mammalian TRP-4 polypeptide.

14. A method of treating a disease or disorder in a subject in need thereof, said method comprising:
   (i) transducing into a cell of a subject a heterologous nucleic acid molecule encoding a exogenous, non-mammalian mechanotransduction TRP-4 polypeptide, which is expressed in the cell;
(ii) applying ultrasound to the cell; and
(iii) inducing cation influx in the TRP-4-expressing cell and an alteration in cell activity and/or function following said application of ultrasound, thereby treating the disease or disorder in said subject.

15. The method of claim 14, wherein said disease is a neurological disease selected from the group consisting of Parkinson Disease, depression, obsessive-compulsive disorder, chronic pain, epilepsy or cervical spinal cord injury.

16. The method of claim 14, wherein said disorder is muscle weakness.

17. A method of activating or modifying cell activity or function, the method comprising:
transducing a cell to express an exogenous, non-mammalian mechanotransduction TRP-4 polypeptide;
applying focused ultrasound to the TRP-4 polypeptide-expressing cell;
inducing cation influx in the TRP-4-expressing cell and an alteration in cell activity and/or function following said application of ultrasound, thereby activating or modifying cell activity or function.

18. The method of claim 17, wherein the cell is a mammalian cell.

19. The method of claim 17, wherein the cell is a muscle cell, cardiac muscle cell, neuron, motor neuron, sensory neuron, interneuron, or insulin secreting cell.

20. The method of claim 17, wherein said ultrasound has a frequency of about 0.8 MHz to about 4 MHz.

21. The method of claim 17, wherein said ultrasound has a focal zone of about 1 cubic millimeter to about 1 cubic centimeter.

22. The method of claim 17, wherein the cell is transduced using a vector comprising a polynucleotide sequence encoding the exogenous, non-mammalian TRP-4 polypeptide or using a recombinant nucleic acid molecule encoding the exogenous, non-mammalian TRP-4 polypeptide.

23. A method of sensitizing a neuron to mechanical deformation or stretch caused by ultrasound and activating and/or modifying activity or function of the neuron, the method comprising:
transducing a neuron to express an exogenous, non-mammalian mechanosensitive TRP-4 polypeptide;
applying ultrasound to the TRP-4 polypeptide-expressing neuron; and
inducing cation influx in the TRP-4-expressing neuron and an alteration in neuron activity and/or function following said application of ultrasound, thereby sensitizing the neuron to mechanical deformation or stretch caused by ultrasound and activating and/or modifying neuron activity or function.

24. The method of claim 23, wherein the ultrasound is applied at a peak negative pressure level of less than about 0.5 MPa.

25. The method of claim 23, wherein the neuron is a motor neuron, a sensory neuron, or an interneuron.

26. The method of claim 23, wherein the neuron is transduced using a vector comprising a polynucleotide sequence encoding the exogenous, non-mammalian TRP-4 polypeptide or using a recombinant nucleic acid molecule encoding the exogenous, non-mammalian TRP-4 polypeptide.

27. A method of inducing cation influx in a cell and sensitizing the cell to mechanical deformation or stretch caused by ultrasound, the method comprising:
transducing a cell to express an exogenous, non-mammalian mechanotransduction TRP-N polypeptide;
applying ultrasound to the cell; and
inducing cation influx in the TRP-N-expressing cell and an alteration in cell activity and/or function following said application of ultrasound, thereby inducing cation influx into the cell and sensitizing the cell to mechanical deformation or stretch caused by ultrasound.

28. The method of claim 27, wherein the exogenous, non-mammalian, mechanotransduction TRP-N polypeptide is TRP-4.

29. The method of claim 28, wherein said TRP-4 polypeptide comprises the amino acid sequence of SEQ ID NO: 1.

30. The method of claim 27, wherein the cell is a mammalian cell.

31. The method of claim 27, wherein the cell is in vitro or in vivo.

32. The method of claim 27, wherein the cell is a muscle cell, cardiac muscle cell, neuron, motor neuron, sensory neuron, interneuron, or insulin secreting cell.

33. The method of claim 27, wherein said ultrasound has a frequency of about 0.8 MHz to about 4 MHz.

34. The method of claim 27, wherein said ultrasound has a focal zone of about 1 cubic millimeter to about 1 cubic centimeter.

35. The method of claim 27, wherein the cell is transduced using a vector comprising a polynucleotide sequence encoding the exogenous, non-mammalian TRP-N polypeptide or using a recombinant nucleic acid molecule encoding the exogenous, non-mammalian TRP-N polypeptide.

* * * * *